United States Patent
Kaur et al.

(10) Patent No.: US 12,042,478 B2
(45) Date of Patent: Jul. 23, 2024

(54) (R)-2-[(2H-1,3-BENZODIOXOL-5-YL) METHYL]PYRROLIDINE AND PROCESSES FOR PREPARATION, COMPOSITIONS AND USES THEREOF

(71) Applicant: Pharmala Biotech Inc., Vancouver (CA)

(72) Inventors: Harpreet Kaur, Colwood (CA); Tao Xin, Woodbridge (CA)

(73) Assignee: PHARMALA BIOTECH, Vancouver (CA)

( * ) Notice: Subject to any disclaimer, the term of this patent is extended or adjusted under 35 U.S.C. 154(b) by 0 days.

(21) Appl. No.: 18/380,423

(22) Filed: Oct. 16, 2023

(65) Prior Publication Data
US 2024/0051947 A1    Feb. 15, 2024

Related U.S. Application Data

(63) Continuation of application No. PCT/CA2023/051019, filed on Jul. 28, 2023.
(Continued)

(51) Int. Cl.
*A61K 31/335* (2006.01)
*A61K 31/4025* (2006.01)
(Continued)

(52) U.S. Cl.
CPC ........ *A61K 31/335* (2013.01); *A61K 31/4025* (2013.01); *A61P 25/00* (2018.01); *C07D 405/10* (2013.01); *C07B 2200/07* (2013.01)

(58) Field of Classification Search
CPC ................ C07D 405/10; A61K 31/335; A61K 31/4025; A61P 25/00
See application file for complete search history.

(56) References Cited

PUBLICATIONS

Dolby et al, J Org Med Chem 1972, vol. 37 (23), pp. 3691-3695. (Year: 1972).*
(Continued)

*Primary Examiner* — Craig D Ricci
*Assistant Examiner* — Janet L Coppins
(74) *Attorney, Agent, or Firm* — Bereskin & Parr LLP/S.E.N.C.R.L., s.r.l.; Sandra Marone

(57) ABSTRACT

The present application includes an enantiomerically pure compound of Formula (R)-I or a salt and/or solvate thereof.

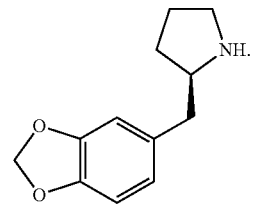

(R)-I

Also included are compositions of the enantiomerically pure compound of Formula (R)-I as well as methods of using the compound of Formula (R)-I or composition thereof for treating, for example, disease, disorder or condition that benefits from psychotherapy.

The present application also includes a composition comprising a non-racemic mixture a compound of Formula (R)-I, or a salt and/or solvate thereof, and (S)-I, or a salt and/or solvate thereof:

(Continued)

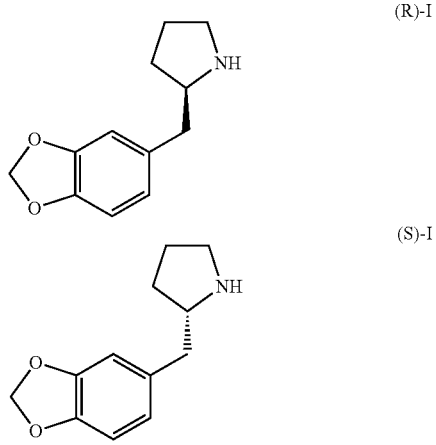

(R)-I (S)-I wherein (R)-I, or a salt and/or solvate thereof, is present in the composition in a greater amount by enantiomeric equivalents, relative to (S)-I, or a salt and/or solvate thereof and uses thereof.

Further included are process preparing a compound of Formula (R)-I or (S)-I.

6 Claims, 23 Drawing Sheets

Related U.S. Application Data

(60) Provisional application No. 63/392,948, filed on Jul. 28, 2022.

(51) Int. Cl.
*A61P 25/00* (2006.01)
*C07D 405/10* (2006.01)

(56) References Cited

PUBLICATIONS

International Search Report and Written Opinion dated Aug. 31, 2023 in respect of PCT/CA2023/051019.
Dolby et al., "Studies of the Synthesis of Cephalotaxine. I", Journal of Organic Chemistry, 1972, vol. 37, Issue 23, pp. 3691-3693.
Williams et al., "Discovery and Optimisation of 1-acyl-2-benzylpyrrolidines as potent dual orexin receptor antagonists", MedChemComm, 2015, vol. 6, Issue 6, pp. 1054-1064.
Baumann et al., "Effects of Dose and Route of Administration on Pharmacokinetics of (±)-3,4-Methylenedioxymethamphetamine in the Rat", Drug Metabolism and Disposition, vol. 37, No. 11, 2009, pp. 2163-2170.
Schwaninger et al., "Stereoselective urinary MDMA (ecstasy) and metabolites excretion kinetics following controlled MDMA administration to humans", Biochemical Pharmacology 83 (2012) pp. 131-138.
Quintana et al., "The promise and pitfalls of intranasally administering psychopharmacological agents for the treatment of psychiatric disorders", Molecular Psychiatry (2016) 21, pp. 29-38.
Wang et al., "Structural insight into the serotonin (5-HT) receptor family by molecular docking, molecular dynamics simulation and systems pharmacology analysis", Acta Pharmacologica Sinica (2019) 40, pp. 1138-1156.
Halgren et al., "Glide: A New Approach for Rapid, Accurate Docking and Scoring. 2. Enrichment Factors in Database Screening", J. Med. Chem. 2004, 47, pp. 1750-1759.
McClure-Begley TD and Roth BL. The promises and perils of psychedelic pharmacology for psychiatry. Nat Rev Drug Discov. 2022;1-11.

\* cited by examiner

A

B

(R)-2-[(2H-1,3-BENZODIOXOL-5-YL)METHYL]PYRROLIDINE AND PROCESSES FOR PREPARATION, COMPOSITIONS AND USES THEREOF

RELATED APPLICATIONS

The present application is a continuation of International Application No. PCT/CA2023/051019 filed Jul. 28, 2023, which claims the benefit of priority of U.S. provisional patent application No. 63/392,948 filed on Jul. 28, 2022, the contents of both of which are incorporated herein by reference in their entirety.

FIELD

The present application relates to enantiomerically pure (R)-2-[(2H-1,3-benzodioxol-5-yl)methyl]pyrrolidine or a salt and/or solvate thereof, and to compositions and uses thereof. The present application also relates to compositions comprising non-racemic mixtures of 2-[(2H-1,3-benzodioxol-5-yl)methyl]pyrrolidine and to methods of using these compositions in therapeutic treatments, for example, for treating a psychiatric disorder. The present application also relates to processes for preparing 2-[(2H-1,3-benzodioxol-5-yl)methyl]pyrrolidine.

BACKGROUND 3,4-Methylenedioxymethamphetamine (MDMA), commonly known as ecstasy (E) or molly, is a psychoactive drug first developed in 1912 by Merck. MDMA is often used recreationally today. However, an initial use of MDMA was as an adjunct to psychotherapy. More recently, MDMA has been studied in various clinical trials, for example, investigating MDMA-assisted psychotherapy for posttraumatic stress disorder (PTSD), anxiety related to advanced-stage illness, and social anxiety in autistic adults. MDMA has now been granted Breakthrough Therapy Designation for the treatment of PTSD by the United States Food and Drug Administration (FDA).

MDMA is generally available and consumed as a racemate. The racemate of MDMA is also known to have potential for adverse effects such as hyperthermia and neurotoxicity. However, studies have shown qualitative differences in the effects of the isomers of MDMA. Evidence suggests that the R isomer of MDMA may provide an improved therapeutic index by maintaining some of the therapeutic effects of MDMA racemate with a reduced side effect profile (Pitts et al. Psychopharmacology 235, 377-392, 2018 and Curry et al. Neuropharmacology. 2018 January; 128: 196-206).

Analogues of MDMA are known, for example, N-methyl-1,3-benzodioxolylbutanamine (MBDB) commonly known as Eden or Methyl-J, is an analogue of MDMA which has an ethyl group instead of a methyl group attached to the alpha carbon next to the amine. Like MDMA, MBDB is also classified as an entactogen. MBDB is also generally available and consumed as a racemate.

Processes for the synthesis of a cyclic analogue of MDMA, 2-[(2H-1,3-benzodioxol-5-yl)methyl]pyrrolidine and its S enantiomer, have been disclosed in Williams et al., Med. Chem. Commun., 2015, 6, 1054 and Dolby L. J. et al, J. Org. Chem., 37 (23), 1972 p 3691.

There is a need for further development of analogues of MDMA and also further investigations to determine the therapeutic potential of the enantiomers of MDMA and analogues thereof.

SUMMARY

The Applicant investigates analogues of MDMA, namely (R)-2-[(2H-1,3-benzodioxol-5-yl)methyl]pyrrolidine and provides enantiomerically pure (R)-2-[(2H-1,3-benzodioxol-5-yl)methyl]pyrrolidine and, processes for preparation, compositions and uses thereof.

The Applicant further investigates compositions comprising non-racemic mixtures of the enantiomers of 2-[(2H-1,3-benzodioxol-5-yl)methyl]pyrrolidine which comprise a greater amount of the R enantiomer to develop a composition comprising a sufficient amount of the R enantiomer to achieve an improved toxicological profile compared to racemic mixture of 2-[(2H-1,3-benzodioxol-5-yl)methyl]pyrrolidine such as decreased cardiotoxicity. The Applicant develops a composition comprising an optimum range for the ratio of the two enantiomers of 2-[(2h-1,3-benzodioxol-5-yl)methyl]pyrrolidine, to provide the desired efficacy yet minimize the undesirable effects.

In the present application, the Applicant also describes therapeutic new uses for the enantiomerically pure (R)-2-[(2H-1,3-benzodioxol-5-yl)methyl]pyrrolidine and compositions thereof, and for the compositions comprising non-racemic mixtures of the enantiomers of 2-[(2H-1,3-benzodioxol-5-yl)methyl]pyrrolidine, including as therapy for autism-spectrum disorders, clinical depression in palliative patients and substance use disorder (e.g., opioid use disorder).

Therefore, the present application comprises an enantiomerically pure compound of Formula (R)-I or a salt and/or solvate thereof

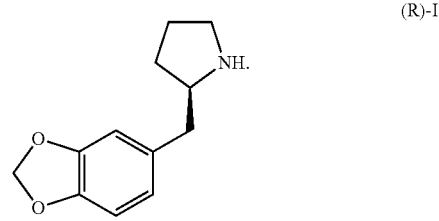 [SMILES: c1cc2c(cc1C[C@H]1CCCN1)OCO2]

(R)-I

The application further includes a composition comprising an enantiomerically pure compound of Formula (R)-I or a salt and/or solvate thereof and a carrier.

The present application also includes a method of treating a disease, disorder or condition treatable by activation of a serotonin receptor comprising administering an enantiomerically pure compound of Formula (R)-I or a pharmaceutically acceptable salt and/or solvate thereof to a subject in need thereof.

The present application further includes a composition comprising a non-racemic mixture a compound of Formula (R)-1, or a salt and/or solvate thereof, and (S)-1, or a salt and/or solvate thereof:

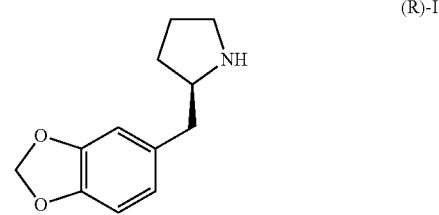 [SMILES: c1cc2c(cc1C[C@H]1CCCN1)OCO2]

(R)-I

-continued

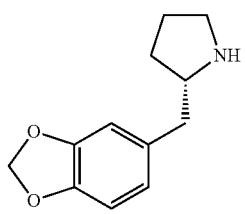
(S)-I wherein the compound of Formula (R)-1, or a salt and/or solvate thereof, is present in the composition in a greater amount by enantiomeric equivalents, relative to (S)-1, or a salt and/or solvate thereof.

The present application includes a method for activating a serotonin receptor in a cell, either in a biological sample or in a patient, comprising administering comprises administering the composition comprising the non-racemic mixture a compound of Formula (R)-1, or a salt and/or solvate thereof, and (S)-1, or a salt and/or solvate thereof to a subject in need thereof.

The present application also includes a method of treating a disease, disorder or condition treatable by activation of serotonin receptor comprising administering the non-racemic mixture a compound of Formula (R)-1, or a salt and/or solvate thereof, and (S)-1, or a salt and/or solvate thereof to a subject in need thereof.

In some embodiments, the disease, disorder or condition that is treated by activation of a serotonin receptor is a disease, disorder or condition that benefits from treatment with racemic MDMA, a disease, disorder or condition that benefits from treatment with racemic MBDB, any disease, disorder or condition that benefits from psychotherapy and any disease, disorder or condition that benefits from treatment with L-3,4-dihydroxyphenylalanine (L-DOPA) such as Parkinson's Disease.

The present application includes a process for preparing a compound of Formula (R)-I or (S)-I:

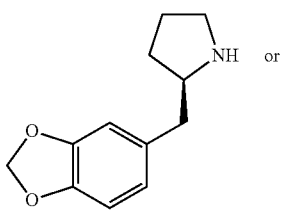
(R)-I or

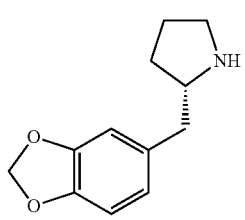
(S)-I the process comprising:
reacting a compound of Formula (R)-A or (S)-A

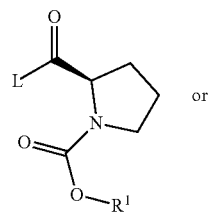
(R)-A or

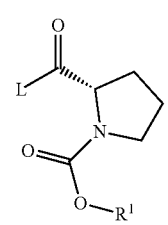
(S)-A wherein L is selected from halo and $C(O)OR^2$,
$R^1$ is an unsubstituted or substituted benzyl group; and
$R^2$ is $C_{1-6}$alkyl, or
$R^2$ is

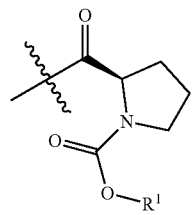

in the compound of Formula (R)-A or $R^2$ is

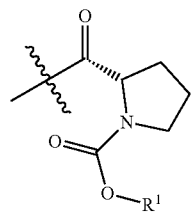

in the compound of Formula (S)-A,
with a compound of Formula B

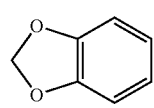

in the presence of a Lewis acid to provide a compound of Formula (R)-C and (S)-C, respectively; and

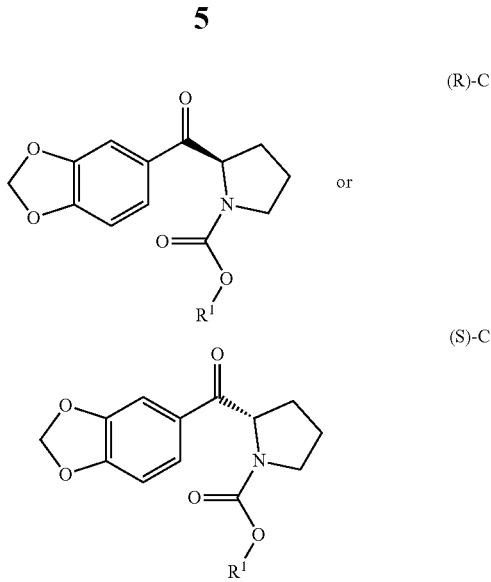

wherein R¹ is an unsubstituted or substituted benzyl group converting the compound of Formula (R)-C and (S)-C to the compound of Formula (R)-I or (S)-I, respectively.

Other features and advantages of the present application will become apparent from the following detailed description. It should be understood, however, that the detailed description and the specific examples, while indicating embodiments of the application, are given by way of illustration only and the scope of the claims should not be limited by these embodiments but should be given the broadest interpretation consistent with the description as a whole.

BRIEF DESCRIPTION OF THE DRAWINGS

The present application will be described in greater detail with reference to the attached drawings and Tables in which.

DETAILED DESCRIPTION

I. Definitions

Figure 1:
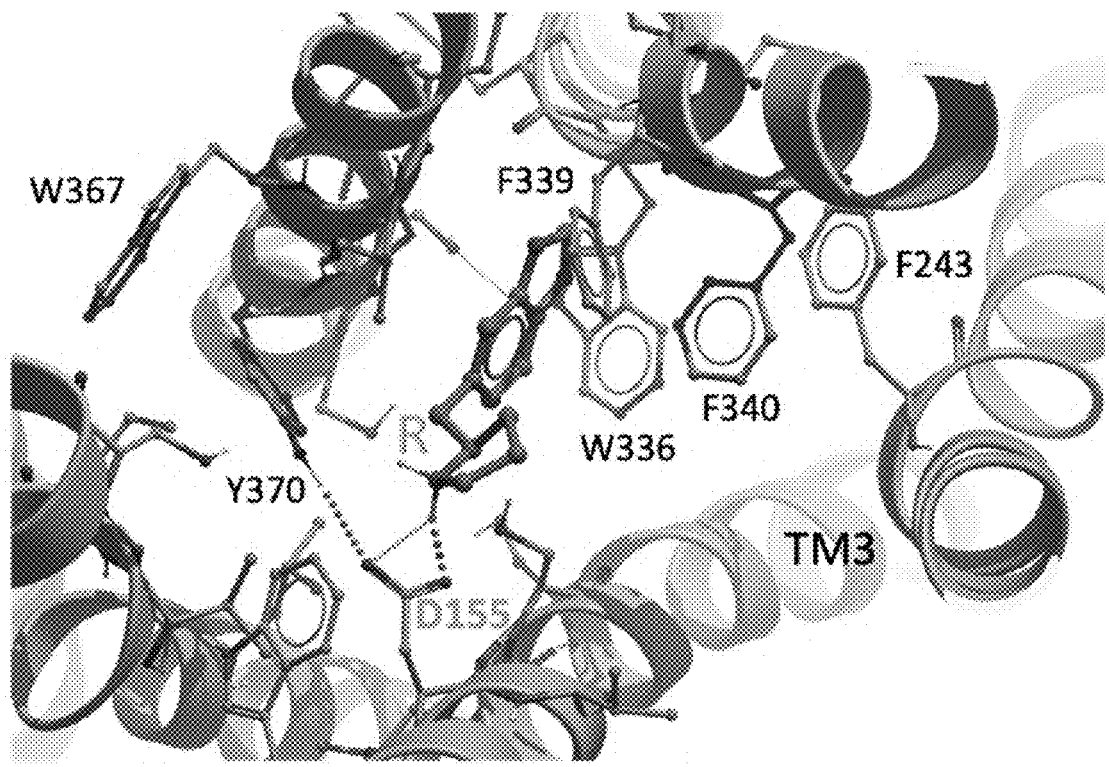
FIG. 1 are pictures showing the results of docking studies with the compound of Formula (R)-I (top panel) and the compound of Formula (S)-I (bottom panel) with the 5-HT$_{2A}$ receptor using Glide® using 6WHA cryoEM structure of 5-HT$_{2A}$, resolved at 3.4 A.
Figure 1:
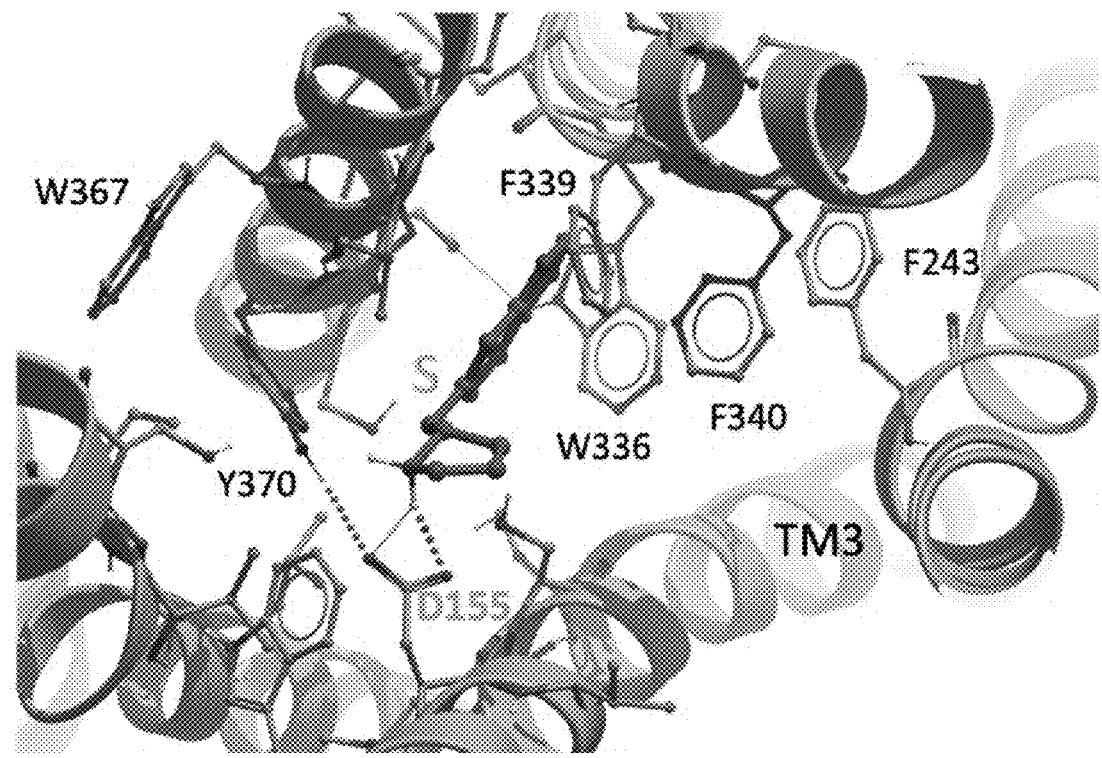

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

The term "compound of the application" or "compound of the present application" and the like as used herein refers to an enantiomerically pure compound of Formula (R)-I, including pharmaceutically acceptable salts or solvates thereof.

The term "composition of the application" as used herein refers to any composition comprising an enantiomerically pure compound of Formula (R)-I and/or a salt and/or solvate thereof as described herein and/or a salt and/or solvate thereof and any compositions comprising non-racemic mixture of compounds of Formula (R)-I and (S)-I, and/or a salt and/or solvate thereof as described herein.

The term "non-racemic" as used herein in reference to a mixture comprising two enantiomeric compounds means that the mixture comprises the two enantiomeric compounds a ratio of other than 1:1.

The term "racemic" as used herein in reference to a mixture comprising two enantiomeric compounds means that the mixture comprises the two enantiomeric compounds in a ratio of 1:1 or in equal amounts.

The term "consisting" and its derivatives, as used herein, are intended to be closed terms that specify the presence of the stated features, elements, components, groups, integers, and/or steps, but exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end-result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise.

In embodiments comprising an "additional" or "second" component, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The term "subject" as used herein includes all members of the animal kingdom including mammals, and suitably refers to humans. Thus, the methods of the present application are applicable to both human therapy and veterinary applications.

The term "compound of Formula (R/S)-I" as used herein refers to a compound having the chemical name (R/S)-2-[(2H-1,3-benzodioxol-5-yl)methyl]pyrrolidine or (R/S)-2-(benzo[d][1,3]dioxol-5-ylmethyl)pyrrolidine and having the chemical structure:

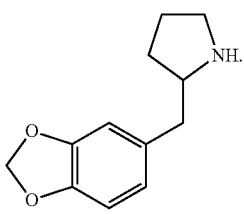

The term "compound of Formula (R)-I" as used herein refers to a compound having the chemical name (R)-2-[(2H-1,3-benzodioxol-5-yl)methyl]pyrrolidine or (R)-2-(benzo[d][1,3]dioxol-5-ylmethyl)pyrrolidine and having the chemical structure:

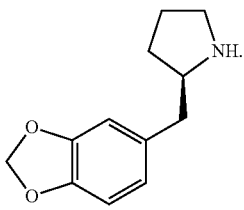 [SMILES: c1cc2c(cc1C[C@H]1CCCN1)OCO2]

The term "compound of Formula (S)-I" as used herein refers to a compound having the chemical name (S)-2-[(2H-1,3-benzodioxol-5-yl)methyl]pyrrolidine or (S)-2-(benzo[d][1,3]dioxol-5-ylmethyl)pyrrolidine, and having the chemical structure:

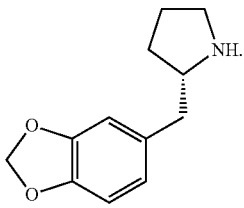 [SMILES: c1cc2c(cc1C[C@@H]1CCCN1)OCO2]

The term "MDMA" or "racemic MDMA" as used herein refers to a compound having the chemical name: 1-(1,3-benzodioxol-5-yl)-N-methylpropan-2-amine, or the chemical name 3,4-Methylenedioxymethamphetamine, and having the chemical structure:

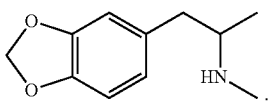

The term "MBDB" as used herein refers to a compound having the chemical name: 1-(1,3-benzodioxol-5-yl)-N-methylbutan-2-amine or N-methyl-1,3-benzodioxolylbutanamine, and having the chemical formula:

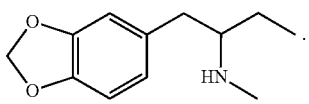

The term "reducing agent" as used herein means any compound or combination of compounds that reduces a desired functional group. A reducing agent results in the overall addition of electrons, or in the case of organic chemistry, hydrogen atoms to the functional group.

The term "inert solvent" as used herein means a solvent that does not interfere with or otherwise inhibit a reaction. Accordingly, the identity of the inert solvent will vary depending on the reaction being performed. The selection of inert solvent is within the skill of a person in the art.

The term "solvent" includes both a single solvent and a mixture comprising two or more solvents.

The term "protecting group" or "PG" and the like as used herein refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, $3^{rd}$ Edition, 1999 and in Kocienski, P. Protecting Groups, 3rd Edition, 2003, Georg Thieme Verlag (The Americas).

The term "enantiomerically pure" are used herein means one enantiomer of a compound that is largely free of the opposite enantiomer of the compound.

The term "largely" as used herein in reference an enantiomerically pure compound should be construed as meaning that the enantiomerically pure compound comprises less than 1% of the opposite enantiomer of the compound.

The term "enantiomeric excess" or "ee" is the absolute difference between the mole fraction of each enantiomer for a racemic compound.

The term "pharmaceutical composition" as used herein refers to a composition of matter for pharmaceutical use.

The term "for pharmaceutical use" means compatible with the treatment of subjects.

The term "pharmaceutically acceptable" means compatible with the treatment of subjects.

The term "pharmaceutically acceptable salt" means an acid addition salt which is suitable for, or compatible with the treatment of subjects.

An acid addition salt suitable for, or compatible with, the treatment of subjects is any non-toxic organic or inorganic acid addition salt of any basic compound.

The term "solvate" as used herein means a compound, or a salt of a compound, wherein molecules of a suitable solvent are incorporated in the crystal lattice. A suitable solvent is physiologically tolerable at the dosage administered.

The term "administered" as used herein means administration of a composition of the application or of a compound of Formula (R)-I or a pharmaceutically acceptable salt and/or solvate thereof, to a cell either in cell culture or in a subject.

The terms "to treat", "treating" and "treatment" as used herein and as is well understood in the art, means an approach for obtaining beneficial or desired results, including clinical results. Examples of beneficial or desired clinical results with respect to any disease, disorder or condition, include, but are not limited to diminishment of extent, stabilized (i.e., not worsening) state, preventing spread, delay or slowing of progression, amelioration or palliation of the state, and remission (whether partial or total), whether detectable or undetectable. "To treat", "treating" and "treatment" can also mean prolonging survival as compared to expected survival if not receiving treatment.

"Palliating" a disease, disorder or condition means that the extent and/or undesirable clinical manifestations of a disease, disorder or condition are lessened and/or time course of the progression is slowed or lengthened, as compared to not treating the disease, disorder or condition.

The term "prevention" or "prophylaxis", or synonym thereto, as used herein refers to a reduction in the risk or probability of a patient becoming afflicted with a disease, disorder or condition or manifesting a symptom associated with a disease, disorder or condition.

The term "treating a disease, disorder or condition treatable by activation of a serotonin receptor" as used herein means that the disease, disorder or condition to be treated is affected by, modulated by and/or has some biological basis, either direct or indirect, that includes serotonergic activity, in particular increases in serotonergic activity. These diseases respond favourably when serotonergic activity associated with the disease, disorder or condition is agonized by one or more of the compounds or compositions of the application.

The term "activation" as used herein includes agonism, partial agonist and positive allosteric modulation of a serotonin receptor.

The terms "5-HT$_{2A}$" are used herein means the 5-HT$_{2A}$ HT$_{2A}$ receptor subtype of the 5-HT$_2$ serotonin receptor.

The term "therapeutic agent" as used herein refers to any drug or active agent that has a pharmacological effect when administered to a subject.

The term "ON-time" as used herein means the duration of the antiparkinsonian effect of L-DOPA.

When used, for example, with respect to the methods of treatment, uses, compositions and/or kits of the application, a subject, for example a subject "in need thereof" is a subject who has been diagnosed and/or has been treated for a disease, disorder or condition that is treatable by activation of a serotonin receptor, for example, 5-HT$_{2A}$.

The term "enantiomeric equivalents" as used herein refers to the molar amount of the base compound of each enantiomer, i.e., compound of Formula (R)-I and compound of Formula (S)-I, irrespective of whether the enantiomer is present as a salt and/or solvate. Therefore, the percent of enantiomeric equivalents of each of (R)-I and (S)-I is defined by the molar quantity of either (R)-I or (S)-I divided by the total molar quantity of both (R)-I and (S)-I. The amounts of any anion forming salts and/or solvate-forming solvents are excluded and do not count in determining the percent of enantiomeric equivalents of each of (R)-I and (S)-I.

II. Compound of the Application

The Applicant investigated analogues of MDMA, namely (R)-2-[(2H-1,3-benzodioxol-5-yl)methyl]pyrrolidine and provides enantiomerically pure (R)-2-[(2H-1,3-benzodioxol-5-yl)methyl]pyrrolidine and compositions and uses thereof.

The present application includes an enantiomerically pure compound of Formula (R)-I or a salt and/or solvate thereof

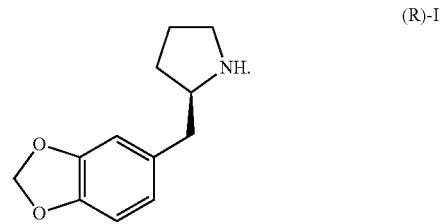 [SMILES: c1cc2c(cc1C[C@H]1CCCN1)OCO2]

(R)-I

In some embodiments, the enantiomerically pure compound of Formula (R)-I or a salt and/or solvate comprises about 99% or greater by weight of the compound of Formula (R)-I and about 1% or less by weight of the compound of Formula (S)-I or a salt and/or solvate thereof

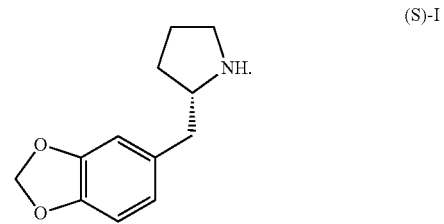 [SMILES: c1cc2c(cc1C[C@@H]1CCCN1)OCO2]

(S)-I

In some embodiments, the enantiomerically pure compound of Formula (R)-I or a salt and/or solvate thereof comprises greater than 99% by weight of the compound of Formula (R)-I or a salt and/or solvate thereof and less than 1% by weight of the compound of Formula (S)-I or a salt and/or solvate thereof. In some embodiments, the enantiomerically pure compound of Formula (R)-I or a salt and/or solvate thereof comprises 99.1%, 99.2%, 99.3%, 99.4%, 99.5%, 99.6%, 99.7%, 99.8%, 99.9%, 99.91%, 99.92%, 99.93%, 99.94%, 99.95%, 99.96%, 99.97%, 99.98%, 99.9% or 100% by weight of the compound of Formula (R)-I or a salt and/or solvate thereof and 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, or 0% respectively less by weight of the compound of Formula (S)-I or a salt and/or solvate thereof.

In some embodiments, the enantiomerically pure compound of Formula (R)-I or a salt and/or solvate thereof comprises an enantiomeric excess (ee) of 98% or more. In some embodiments, the enantiomerically pure compound of Formula (R)-I or a salt and/or solvate thereof comprises comprise an enantiomeric excess (ee) of 98% to 100%. In some embodiments, the enantiomerically pure compound of Formula (R)-I or a salt and/or solvate thereof comprises comprise an enantiomeric excess (ee) of 98%, 98.1%, 98.2%, 98.3% 98.4%, 98.5%, 98.6%, 98.7%, 98.8%, 98.9%, 98.9%, 99%, 99.1%, 99.2%, 99.3%, 99.4%, 99.5%, 99.7%, 99.8%, 99.9% or about 100%.

In some embodiments, the enantiomerically pure compound of Formula (R)-I is in free base form. In some embodiments, the enantiomerically pure compound of Formula (R)-I is in acid salt form or solvate thereof.

In an embodiment the pharmaceutically acceptable salt is an acid addition salt or a base addition salt. The selection of a suitable salt may be made by a person skilled in the art (see, for example, S. M. Berge, et al., "Pharmaceutical Salts," J. Pharm. Sci. 1977, 66, 1-19).

An acid addition salt suitable for, or compatible with, the treatment of subjects is any non-toxic organic or inorganic acid addition salt of any basic compound. Basic compounds that form an acid addition salt include, for example, compounds comprising an amine group. Illustrative inorganic acids which form suitable salts include hydrochloric, hydrobromic, sulfuric, nitric and phosphoric acids, as well as acidic metal salts such as sodium monohydrogen orthophosphate and potassium hydrogen sulfate. Illustrative organic acids which form suitable salts include mono-, di- and tricarboxylic acids. Illustrative of such organic acids are, for example, acetic, trifluoroacetic, propionic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, mandelic, salicylic, 2-phenoxybenzoic, p-toluenesulfonic acid and other sulfonic acids such as methanesulfonic acid, ethanesulfonic acid and 2-hydroxyethanesulfonic acid. In an embodiment, the mono- or di-acid salts are formed, and such salts exist in either a hydrated, solvated or substantially anhydrous form. In general, acid addition salts are more soluble in water and various hydrophilic organic solvents, and generally demonstrate higher melting points in comparison to their free base forms. The selection criteria for the appropriate salt will be known to one skilled in the art. Other non-pharmaceutically acceptable salts such as but not limited to oxalates may be used, for example in the isolation of compounds of the application for laboratory use, or for subsequent conversion to a pharmaceutically acceptable acid addition salt.

In some embodiments, the enantiomerically pure compound of Formula (R)-I or a salt and/or solvate thereof is an enantiomerically pure salt of the compound of Formula (R)-I or solvate thereof. Accordingly, the present application comprises an enantiomerically pure salt of a compound of Formula (R)-I or a solvate thereof. In some embodiments, the enantiomerically pure salt of the compound of Formula (R)-I is the HCl salt. Accordingly, in some embodiments, the present application comprises an enantiomerically pure HCl salt of a compound of Formula (R)-I or a solvate thereof.

In some embodiments, the enantiomerically pure compound of Formula (R)-I or salt thereof is provided as a solvate. Solvates of compounds of the application include, for example, those made with solvents that are pharmaceutically acceptable. Examples of such solvents include water (resulting solvate is called a hydrate) and ethanol and the like. Suitable solvents are physiologically tolerable at the dosage administered.

The compound of the present application may further exist in varying polymorphic forms or an amorphous form and it is contemplated that any polymorphic or amorphic forms, or mixtures thereof, which form are included within the scope of the present application.

In some embodiments, the enantiomerically pure compound of Formula (R)-I or a salt and/or solvate thereof is crystalline. In some embodiments, the enantiomerically pure crystalline compound of Formula (R)-I is an enantiomerically pure crystalline salt of the compound of Formula (R)-I or solvate thereof. In some embodiments, the enantiomerically pure crystalline salt of the compound of Formula (R)-I is the enantiomerically pure crystalline HCl salt of the compound of Formula (R)-I or solvate thereof.

In some embodiments, the enantiomerically pure compound of Formula (R)-I or a salt and/or solvate thereof is amorphous.

In some embodiments, the enantiomeric excess of an enantiomer is determined using a variety of analytical techniques known in the art, including NMR spectroscopy, chiral column chromatography, or optical polarimetry. In some embodiments, the enantiomeric excess of an enantiomer is determined using a polarimeter using methods known in the art.

III. Compositions of the Application (i) Compositions of Enantiomerically Pure Compound of Formula (R)-I or a Salt and/or Solvate Thereof The enantiomerically pure compound of Formula (R)-I or a salt and/or solvate thereof is suitably formulated in a conventional manner into compositions using one or more carriers. Accordingly, the present application also includes a composition comprising an enantiomerically pure compound of Formula (R)-I or a salt and/or solvate thereof and a carrier

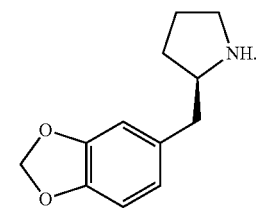 [SMILES: c1cc2c(cc1C[C@H]1CCCN1)OCO2]

The enantiomerically pure compound of Formula (R)-I or a salt and/or solvate thereof is suitably formulated into pharmaceutical compositions for administration to subjects in a biologically compatible form suitable for administration in vivo. Accordingly, the present application further includes a pharmaceutical composition comprising an enantiomerically pure compound of Formula (R)-I or a pharmaceutically acceptable salt and/or solvate thereof and a pharmaceutically acceptable carrier. In embodiments of the application the pharmaceutical compositions are used in the treatment of any of the diseases, disorders or conditions described herein.

In some embodiments of the application the pharmaceutical compositions comprising an enantiomerically pure compound of Formula (R)-I or a pharmaceutically acceptable salt and/or solvate thereof are used in the treatment of any of the diseases, disorders or conditions described herein.

(ii) Compositions of Non-Racemic Mixtures of a Compound of Formula (R)-I and (S)-I of the Application The present application further includes a composition comprising a non-racemic mixture a compound of Formula (R)-I, or a salt and/or solvate thereof, and (S)-I, or a salt and/or solvate thereof:

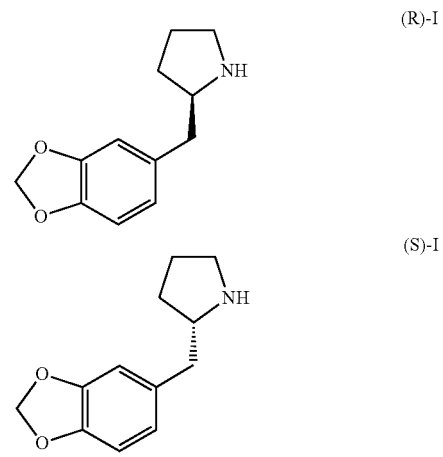

wherein the compound of Formula (R)-I, or a salt and/or solvate thereof, is present in the composition in a greater amount by enantiomeric equivalents, relative to (S)-I, or a salt and/or solvate thereof.

In some embodiments, the composition comprises greater than 50% by enantiomeric equivalents of the compound of Formula (R)-I, or a salt and/or solvate thereof.

In some embodiments, the composition comprises 51% to 99% by enantiomeric equivalents of the compound of Formula (R)-I, or a salt and/or solvate thereof, and 1% to about 49% by enantiomeric equivalents of the compound of Formula (S)-I, or a salt and/or solvate thereof. In some embodiments, the composition comprises 55% to 99%, about 60% to 99%, about 65% to 99%, about 70% to 99%, about 75% to 99%, about 80% to 99%, about 85% to 99%, about 90% to 99%, by enantiomeric equivalents of the compound of Formula (R)-I, or a salt and/or solvate thereof, and 1% to 45%, 1% to about 40%, 1% to about 35%, 1% to about 30%, 1% to about 25%, 1% to about 20%, 1% to about 15%, or 1% to about 10%, respectively by enantiomeric equivalents of the compound of Formula (S)-I, or a salt and/or solvate thereof.

In some embodiments, the composition comprises 51% to 99% by enantiomeric equivalents of the compound of Formula (R)-I, or a salt and/or solvate thereof, and 1% to 49% by enantiomeric equivalents of the compound of Formula (S)-I, or a salt and/or solvate thereof.

In some embodiments, the composition comprises about 60% to 99% by enantiomeric equivalents of the compound of Formula (R)-I, or a salt and/or solvate thereof, and about 1% to about 40% by enantiomeric equivalents of the compound of Formula (S)-I, or a salt and/or solvate thereof.

In some embodiments, the composition comprises about 60% to about 69.9% by enantiomeric equivalents of the compound of Formula (R)-I, or a salt and/or solvate thereof, and about 30.1% to about 40% by enantiomeric equivalents of the compound of Formula (S)-I, or a salt and/or solvate thereof.

In some embodiments, the composition comprises about 70% to 99% by enantiomeric equivalents of the compound of Formula (R)-I, or a salt and/or solvate thereof, and about 1% to about 30% by enantiomeric equivalents of the compound of Formula (S)-I, or a salt and/or solvate thereof.

In some embodiments, the composition comprises about 70% to about 79.9% by enantiomeric equivalents of the compound of Formula (R)-I, or a salt and/or solvate thereof, and about 20.1% to about 30% by enantiomeric equivalents of the compound of Formula (S)-I, or a salt and/or solvate thereof.

In some embodiments, the composition comprises about 70% to about 75% by enantiomeric equivalents of the compound of Formula (R)-I, or a salt and/or solvate thereof, and 25% to about 30% by enantiomeric equivalents of the compound of Formula (S)-I, or a salt and/or solvate thereof.

In some embodiments, the composition comprises about 75% to about 79.9% by enantiomeric equivalents of the compound of Formula (R)-I, or a salt and/or solvate thereof, and about 20.1% to about 25% by enantiomeric equivalents of the compound of Formula (S)-I, or a salt and/or solvate thereof.

In some embodiments, the composition comprises about 75% to about 85% by enantiomeric equivalents of the compound of Formula (R)-I, or a salt and/or solvate thereof, and about 15% to about 25% by enantiomeric equivalents of the compound of Formula (S)-I, or a salt and/or solvate thereof.

In some embodiments, the composition comprises about 80% to about 89.9% by enantiomeric equivalents of the compound of Formula (R)-I, or a salt and/or solvate thereof, and about 10.1% to about 20% by enantiomeric equivalents of the compound of Formula (S)-I or a salt and/or solvate thereof.

In some embodiments, the composition comprises about 80% to about 85% by enantiomeric equivalents of the Formula (R)-I, or a salt and/or solvate thereof, and about 15% to about 20% by enantiomeric equivalents of the Formula (S)-I, or a salt and/or solvate thereof.

In some embodiments, the composition comprises about 80% by enantiomeric equivalents of the Formula (R)-I, or a salt and/or solvate thereof, and about 20% by enantiomeric equivalents of the Formula (S)-I, or a salt and/or solvate thereof.

In some embodiments, the composition comprises about 85% to about 89.9% by enantiomeric equivalents of the compound of Formula (R)-I, or a salt and/or solvate thereof, and about 10.1% to about 15% by enantiomeric equivalents of the compound of Formula (S)-I, or a salt and/or solvate thereof.

In some embodiments, the composition comprises about 90% to 99% by enantiomeric equivalents of the compound of Formula (R)-I, or a salt and/or solvate thereof, and 1% to about 10% by enantiomeric equivalents of the compound of Formula (S)-I, or a salt and/or solvate thereof.

In some embodiments, the composition comprises about 90% to 95% by enantiomeric equivalents of the Formula (R)-I, or a salt and/or solvate thereof, and 5% to about 10% by enantiomeric equivalents the compound of Formula (S)-I, or a salt and/or solvate thereof.

In some embodiments, the composition comprises 95% to 99% by enantiomeric equivalents of the Formula (R)-I, or a salt and/or solvate thereof, and 1% to 5% by enantiomeric equivalents of the compound of Formula (S)-I, or a salt and/or solvate thereof.

In some embodiments, the compounds of Formula (R)-I and (S)-I or a salt and/or solvate thereof in the composition comprising a non-racemic mixture a compound of Formula (R)-I, or a salt and/or solvate thereof, and (S)-I, or a salt and/or solvate thereof of the application are both in free base form. In some embodiments, the compounds of Formula (R)-I and (S)-I a salt and/or solvate thereof are both in acid salt form or solvates thereof.

In some embodiments, the enantiomeric excess of an enantiomer is determined using a variety of analytical techniques known in the art, including NMR spectroscopy, chiral column chromatography, or optical polarimetry. In some embodiments, the enantiomeric excess of an enantiomer is determined using optical rotation using a polarimeter using methods known in the art.

(iii) Compositions of the Application

In some embodiments the compounds of Formula (R)-I and/or (S)-I including the enantiomerically pure compound of Formula (R)-I are provided as salts. The selection of a suitable salt may be made by a person skilled in the art. Acids that are generally considered suitable for the formation of pharmaceutically acceptable salts from basic pharmaceutical compounds are discussed, for example, by P. Stahl et al, Camille G. (eds.) and Handbook of Pharmaceutical Salts. Properties, Selection and Use. (2002) Zurich: Wiley VCH; S. Berge et al, Journal of Pharmaceutical Sciences 1977 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website).

In some embodiments, the acid addition salt suitable for, or compatible with, the treatment of subjects is any non-toxic organic or inorganic acid addition salt. Illustrative inorganic acids which form suitable salts include hydrochloric, hydrobromic, sulfuric, nitric and phosphoric acids, as well as acidic metal salts such as sodium monohydrogen orthophosphate and potassium hydrogen sulfate. Illustrative organic acids which form suitable salts include mono-, di- and tricarboxylic acids. Illustrative of such organic acids are, for example, acetic, trifluoroacetic, propionic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, mandelic, salicylic, 2-phenoxybenzoic, p-toluenesulfonic acid and other sulfonic acids such as methanesulfonic acid, ethanesulfonic acid and 2-hydroxyethanesulfonic acid. In some embodiments, exemplary acid addition salts also include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. In some embodiments, the salts exist in either a hydrated, solvated or substantially anhydrous form. In general, acid addition salts are more soluble in water and various hydrophilic organic solvents and generally demonstrate higher melting points in comparison to their free base forms.

Salts of compounds of compound of Formula (R)-I or (S)-I including the enantiomerically pure compound of Formula (R)-I may be formed by methods known to those of ordinary skill in the art, for example, by reacting (R)-I or (S)-I including the enantiomerically pure compound of Formula (R)-I with an amount of acid, such as an equivalent amount, in a medium such as one in which the salt precipitates or in aqueous medium followed by lyophilization.

In some embodiments the compounds of Formula (R)-I and/or (S)-I including the enantiomerically pure compound of Formula (R)-I are provided solvates. The solvates include, for example, those made with solvents that are pharmaceutically acceptable. Examples of such solvents include water (resulting solvate is called a hydrate) and ethanol and the like. Suitable solvents are physiologically tolerable at the dosage administered.

In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

The compounds of Formula (R)-I and (S)-I including the enantiomerically pure compound of Formula (R)-I, or a pharmaceutically acceptable salt and/or solvate thereof, may further exist in varying polymorphic and amorphic forms and it is contemplated that any polymorphic or amorphous form, or mixtures thereof, which form are included within the scope of the present application. In some embodiments of the application the pharmaceutical compositions of the application are used in the treatment of any of the diseases, disorders or conditions described herein.

The compounds of Formula (R)-I and (S)-I including the enantiomerically pure compound of Formula (R)-I and/or pharmaceutical acceptable salts and/or solvates thereof are suitably formulated into pharmaceutical compositions for administration to subjects in a biologically compatible form suitable for administration in vivo. Accordingly, in an embodiment, the compositions of the application are pharmaceutical compositions and further comprise one or more pharmaceutically acceptable carriers.

The pharmaceutical compositions of the application are administered to a subject in a variety of forms depending on the selected route of administration, as will be understood by those skilled in the art. For example, the compositions of the application are administered by oral, inhalation, parenteral, buccal, sublingual, nasal, rectal, vaginal, patch, pump, minipump, topical or transdermal administration and the pharmaceutical compositions formulated accordingly. In some embodiments, administration is by means of a pump for periodic or continuous delivery. Conventional procedures and ingredients for the selection and preparation of suitable compositions are described, for example, in Remington's Pharmaceutical Sciences (2000-20th edition) and in The United States Pharmacopeia: The National Formulary (USP 24 NF19) published in 1999.

Parenteral administration includes systemic delivery routes other than the gastrointestinal (GI) tract, and includes, for example intravenous, intra-arterial, intraperitoneal, subcutaneous, intramuscular, transepithelial, nasal, intrapulmonary (for example, by use of an aerosol), intrathecal, rectal and topical (including the use of a patch or other transdermal delivery device) modes of administration. Parenteral administration may be by continuous infusion over a selected period of time.

In some embodiments, a composition of the application is orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the composition may be incorporated with excipient and used in the form of ingestible tablets, buccal tablets, troches, capsules, caplets, pellets, granules, lozenges, chewing gum, powders, syrups, elixirs, wafers, aqueous solutions or suspensions, and the like. In the case of tablets, carriers that are used include lactose, corn starch, sodium citrate and salts of phosphoric acid. Pharmaceutically acceptable excipients include binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets are coated by methods well known in the art. In the case of tablets, capsules, caplets, pellets or granules for oral administration, pH sensitive enteric coatings, such as Eudragits™ designed to control the release of active ingredients are optionally used. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. Timed-release compositions can be formulated, e.g., in liposomes or those wherein the compositions are protected with differentially degradable coatings, such as by microencapsulation, multiple coatings, etc. Liposome delivery systems include, for example, small unilamellar vesicles, large unilamellar vesicles and multilamellar vesicles. Liposomes can be formed from a variety of phospholipids, such as cholesterol, stearylamine or phosphatidylcholines. For oral administration in a capsule form, useful carriers or diluents include lactose and dried corn starch.

In some embodiments, liquid preparations for oral administration take the form of, for example, solutions, syrups or suspensions, or they are suitably presented as a dry product for re-constitution with water or other suitable vehicle(s) before use. When aqueous suspensions and/or emulsions are administered orally, the compositions of the application are suitably suspended or dissolved in an oily phase that is combined with emulsifying and/or suspending agents. If desired, certain sweetening and/or flavoring and/or coloring agents are added. In some embodiments, such liquid preparations for oral administration are prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid). Useful diluents include lactose and high molecular weight polyethylene glycols.

In some embodiments, the compositions of the application are formulated as solid or semi-solid compositions. In some embodiments, the compositions of the application are formulated as tablets, buccal tablets, troches, capsules, caplets, pellets, granules, lozenges, chewing gum, powders, syrups, elixirs, wafers, aqueous solutions or suspensions. In some embodiments, the compositions of the application are formulated as tablets or capsules. In some embodiments, the compositions of the application are formulated as tablets.

It is also possible to freeze-dry the compositions of the application and use the lyophilizates obtained, for example, for the preparation of products for injection.

In some embodiments, the compositions of the application are administered parenterally. For example, solutions of the compositions of the application are prepared in water suitably mixed with a surfactant such as hydroxypropylcellulose. In some embodiments, dispersions are prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. For parenteral administration, sterile solutions of the compositions of the application are usually prepared, and the pH's of the solutions are suitably adjusted and buffered. For intravenous use, the total concentration of solutes should be controlled to render the preparation isotonic. For ocular administration, ointments or droppable liquids are delivered, for example, by ocular delivery systems known to the art such as applicators or eye droppers. In some embodiments, such formulations include mucomimetics such as hyaluronic acid, chondroitin sulfate, hydroxypropyl methylcellulose or polyvinyl alcohol, preservatives such as sorbic acid, EDTA or benzyl chromium chloride, and the usual quantities of diluents or carriers. For pulmonary administration, diluents or carriers will be selected to be appropriate to allow the formation of an aerosol.

In some embodiments, the compositions of the application are formulated for parenteral administration by injection, including using conventional catheterization techniques or infusion. Compositions for injection are, for example, presented in unit dosage form, e.g., in ampoules or in multi-dose containers, with an added preservative. In some embodiments, the compositions are formulated as sterile suspensions, solutions or emulsions in oily or aqueous vehicles, and contain formulating agents such as suspending, stabilizing and/or dispersing agents. In all cases, the form must be sterile and must be fluid to the extent that easy syringability exists. Alternatively, the compositions of the application are suitably in a sterile powder form for reconstitution with a suitable vehicle, e.g., sterile pyrogen-free water, before use.

In some embodiments, the compositions of the application are for intranasal administration.

Therefore, in some embodiments, the present application also includes an intranasal composition comprising an enantiomerically pure compound of Formula (R)-I or a salt and/or solvate thereof and a carrier. In some embodiments, the present application further includes an intranasal pharmaceutical composition comprising an enantiomerically pure compound of Formula (R)-I or a pharmaceutically acceptable salt and/or solvate thereof and a pharmaceutically acceptable carrier.

In some embodiments, the present application further includes an intranasal composition comprising a non-racemic mixture a compound of Formula (R)-I, or a salt and/or solvate thereof, and (S)-I, or a salt and/or solvate thereof:
wherein the compound of Formula (R)-I, or a salt and/or solvate thereof, is present in the composition in a greater amount by enantiomeric equivalents, relative to (S)-I, or a salt and/or solvate thereof.

In some embodiments, the enantiomeric equivalents are as described under the "Compositions of non-racemic mixtures of a compound of Formula (R)-I and (S)-I of the application" section.

In embodiments of the application the intranasal compositions are used in the treatment of any of the diseases, disorders or conditions described herein.

In some embodiments, compositions for nasal administration are conveniently formulated as aerosols, drops, gels and powders. For intranasal administration or administration by inhalation, the compositions of the application are conveniently delivered in the form of a solution, dry powder formulation or suspension from a pump spray container that is squeezed or pumped by the subject or as an aerosol spray presentation from a pressurized container or a nebulizer. Aerosol compositions typically comprise a solution or fine suspension of the compositions of the application in a physiologically acceptable aqueous or non-aqueous solvent and are usually presented in single or multidose quantities in sterile form in a sealed container, which, for example, take the form of a cartridge or refill for use with an atomising device. Alternatively, the sealed container is a unitary dispensing device such as a single dose nasal inhaler or an aerosol dispenser fitted with a metering valve which is intended for disposal after use. Where the dosage form comprises an aerosol dispenser, it will contain a propellant which is, for example, a compressed gas such as compressed air or an organic propellant such as fluorochlorohydrocarbon. Suitable propellants include but are not limited to dichlorodifluoromethane, trichlorofluoromethane, dichlorotetrafluoroethane, heptafluoroalkanes, carbon dioxide or another suitable gas. In the case of a pressurized aerosol, the dosage unit is suitably determined by providing a valve to deliver a metered amount. In some embodiments, the pressurized container or nebulizer contains a solution or suspension of the compositions of the application. Capsules and cartridges (made, for example, from gelatin) for use in an inhaler or insufflator are, for example, formulated containing a powder mix of a composition of the application and a suitable powder base such as lactose or starch. The aerosol dosage forms can also take the form of a pump-atomizer.

In some embodiments, intranasal pharmaceutical composition is formulated as an aerosol for use with a pump-atomizer.

In some embodiments, the intranasal pharmaceutical composition is a powder. In some embodiments, the intranasal pharmaceutical composition is a dry powder. In some embodiment, the dry powder is formulated to be reconstituted with a suitable vehicle before use or administration. In some embodiments the suitable vehicle is sterile pyrogen-free water.

In some embodiments, the powder is formulated for use or administration with an inhaler or insufflator. Accordingly, in some embodiments, the dry powder is formulated for use or administration as a capsule and cartridge for use with an inhaler or insufflator.

In some embodiments, the dry powder further comprises a suitable powder base. In some embodiment, the suitable powder based comprise lactose or starch.

In some embodiments, the intranasal pharmaceutical composition further comprises water. Therefore, in some embodiments, the intranasal pharmaceutical composition further comprises water and is an aqueous intranasal pharmaceutical composition.

In some embodiments, the intranasal pharmaceutical composition is a solution, suspension or emulsion. In some embodiments, the intranasal pharmaceutical composition is a solution.

In some embodiments, the aqueous intranasal pharmaceutical composition is formulated for administration into nose in the form of drops. In some embodiments, the aqueous intranasal pharmaceutical composition is formulated for administration as a nasal spray. In some embodiments, the nasal spray is delivered in the form of a solution or suspension from a pump spray container that is squeezed or pumped by the patient or as an aerosol spray presentation from a pressurized container or a nebulizer. In some embodiments, the aqueous intranasal pharmaceutical composition is formulated as an aerosol for use with a pump-atomizer.

In some embodiments, the water is present in an amount of about 50% to about 75%, about 50% to about 70%, about 50% to about 65%, about 33% to about 75%, about 55% to about 70% or about 55% to about 65% by weight of the composition. In some embodiments, the water is present in an amount of about 50%, about 60%, about 65% or about 70% by weight of the composition. In some embodiments, the water is present in an amount of about 55% to about 65% by weight of the composition. In some embodiments, the water is about 60% by weight of the composition.

Compositions suitable for buccal or sublingual administration include tablets, lozenges, and pastilles, wherein the compositions of the application are formulated with a carrier such as sugar, acacia, tragacanth, or gelatin and glycerine. Compositions for rectal administration are conveniently in the form of suppositories containing a conventional suppository base such as cocoa butter.

In some embodiments, the compositions of the application are for sublingual administration.

Therefore, in some embodiments, the present application also includes a sublingual composition comprising an enantiomerically pure compound of Formula (R)-I or a salt and/or solvate thereof and a carrier. In some embodiments, the present application further includes a sublingual pharmaceutical composition comprising an enantiomerically pure compound of Formula (R)-I or a pharmaceutically acceptable salt and/or solvate thereof and a pharmaceutically acceptable carrier.

In some embodiments, the present application further includes a sublingual composition comprising a non-racemic mixture a compound of Formula (R)-I, or a salt and/or solvate thereof, and (S)-I, or a salt and/or solvate thereof:
  wherein the compound of Formula (R)-I, or a salt and/or solvate thereof, is present in the composition in a greater amount by enantiomeric equivalents, relative to (S)-I, or a salt and/or solvate thereof.

In some embodiments, the enantiomeric equivalents are as described under the "Compositions of non-racemic mixtures of a compound of Formula (R)-I and (S)-I of the application" section.

In some embodiments, the sublingual dosage form is a formulated as tablets, drops, strips, sprays, lozenges or effervescent tablets.

In embodiments of the application the sublingual compositions are used in the treatment of any of the diseases, disorders or conditions described herein.

In some embodiments, the intranasal and/or sublingual compositions provide a faster onset of activity, exhibit reduced neurotoxicity and/or exhibit reduced cardiotoxicity compared to an oral composition. In some embodiments, required dose of a compound of Formula (R)-I, or the dose of non-racemic combination of a compound of Formula (R)-I and a compound of Formula (S)-I in an intranasal and/or a sublingual compositions is lower compared to the dose of a compound of Formula (R)-I, or the dose of non-racemic combination of a compound of Formula (R)-I and a compound of Formula (S)-I oral composition to achieve an identical beneficial effect.

Suppository forms of the compositions of the application are useful for vaginal, urethral and rectal administrations. Such suppositories will generally be constructed of a mixture of substances that is solid at room temperature but melts at body temperature. The substances commonly used to create such vehicles include but are not limited to theobroma oil (also known as cocoa butter), glycerinated gelatin, other glycerides, hydrogenated vegetable oils, mixtures of polyethylene glycols of various molecular weights and fatty acid esters of polyethylene glycol. See, for example: Remington's Pharmaceutical Sciences, 16th Ed., Mack Publishing, Easton, P A, 1980, pp. 1530-1533 for further discussion of suppository dosage forms.

In some embodiments, the compositions of the application comprise about 40 mg to about 180 mg of the compound of Formulae (R)-I or both the compounds of Formulae (R)-I and (S)-I, and/or a salt and/or solvate thereof. In some embodiments, the compositions of the application comprise 40 mg, 60 mg, 75 mg, 80 mg, 100 mg, 120 mg or 125 mg of the compound of Formulae (R)-I or of both the compounds of Formulae (R)-I and (S)-I, and/or a salt and/or solvate thereof. In some embodiments, depending on the mode of administration, the compositions of the application are pharmaceutical compositions that comprise about 0.05 wt % to about 99 wt % or about 0.10 wt % to about 70 wt %, of the compound of Formulae (R)-I or of both the compounds of Formulae (R)-I and (S)-I, and/or a pharmaceutical acceptable salt and/or solvate thereof, and from about 1 wt % to about 99.95 wt % or about 30 wt % to about 99.90 wt % of one or more pharmaceutically acceptable carriers, all percentages by weight being based on the total composition.

In some embodiments, the enantiomerically pure compound of Formula (R)-I is and/or a salt and/or solvate thereof, or both the compounds of Formulae (R)-I and (S)-I, and/or a salt and/or solvate thereof, are present in the compositions in an effective amount, for example an effective amount to treat or prevent a disease, disorder or condition that is treatable by activation of a serotonin receptor, in particular 5-HT$_{2A}$.

In some embodiments the compositions of the application are pharmaceutical compositions comprising an additional therapeutic agent, and optionally one or more pharmaceutically acceptable carriers. In some embodiments, the additional therapeutic agent is known agent useful for treating a disease, disorder or condition that benefits from treatment with a racemic MDMA, and/or pharmaceutically acceptable salts and/or solvates thereof, or that benefits from treatment with psychotherapy in combination with a racemic MDMA, and/or pharmaceutically acceptable salts and/or solvates thereof.

IV. Methods and Uses of the Application (i) Methods and Uses of (R)-2-[(2H-1,3-benzodioxol-5-yl)methyl]pyrrolidine Three-dimensional models for all 5-hydroxytryptamine (5-HT) receptors subtypes have been built and validated based on the existing crystal structure data of 5-HT$_{1B}$/5-HT$_{2B}$/5-HT$_{2C}$ using homology modeling and residues that contribute to the selectivity of each receptor have been identified (Wang, Y-q et al. Acta Pharmacologica Sinica (2019) 40:1138-1156). Using such models, the Applicants have performed molecular docking studies using the (R) enantiomer of 2-[(2H-1,3-benzodioxol-5-yl)methyl]pyrrolidine (compound of Formula (R)-I). The Applicants have shown that the (R) enantiomer of 2-[(2H-1,3-benzodioxol-5-yl)methyl]pyrrolidine binds with less, and more balanced, affinity to the 5-hydroxytryptamine 2B receptor (5-HT$_{2B}$) and 5-hydroxytryptamine 2A receptor (5-HT$_{2A}$) compared to its opposite enantiomer, with the opposite enantiomer having higher affinity for the 5-hydroxytryptamine 2B receptor (5-HT$_{2B}$).

5-HT$_{2B}$ has been implicated in mediated toxicity associated with racemic MDMA such as cardiotoxicity for example, valvular heart disease (Setola V et al. Molecular Pharmacology, 63, 1223-1229, 2003, Huot et al. Journal of Neuroscience, 2011, 31 (19) 7190-7198). However, therapeutic activity involves binding to both 5-HT$_{2B}$ and 5-HT$_{2A}$. Therefore, a compound with a more balanced affinity between 5-HT$_{2B}$ and 5-HT$_{2A}$ would be advantageous.

Therefore, the (R) enantiomer of 2-[(2H-1,3-benzodioxol-5-yl)methyl]pyrrolidine is expected to have improved toxicological profile compared its racemate (i.e. the compound of Formula (R/S)-I) while maintaining the therapeutic effects of the racemate.

Indeed, the Applicant has performed studies in C57 mice, a general population mouse model and in BTBR mice, a mouse model of autism spectrum disorders, and has shown that in core temperature and locomotor activity studies in both C57 mice and BTBR mice, the (R) enantiomer of 2-[(2H-1,3-benzodioxol-5-yl)methyl]pyrrolidine (compound of Formula (R)-I), unlike MDMA, did not elicit a dose dependent increase in core body temperature in either mouse model. It is known that increasing body temperature, hyperthermia, results in cellular damage and neurotoxicity (Walter and Carraretto, Crit Care. 2016 Jul. 14; 20(1):199). Further, while compound of Formula (R)-I did exhibit a dose dependent hypothermic effect, no drop in core body temperature was seen at doses of about 5.6 mg/kg (R)-I in either mouse strain. In contrast, the (S) enantiomer of 2-[(2H-1,3-benzodioxol-5-yl)methyl]pyrrolidine (compound of Formula (S)-I) was found to elicit a significant drop in temperature at the lower dose of about 5.6 mg/kg. Therefore, the Applicant has shown that at doses of about 5.6 mg/kg (R)-I does not elicit a rise or drop in core body temperature in the test mice strains.

These studies have further shown neither of (R)-I or (S)-I elicited a significant dose dependent locomotor stimulant effect.

In cardiovascular toxicity studies, compound of Formula (R)-I was shown to have a significantly lower impact on cardiovascular effects as measured by systolic pressure, diastolic pressure and mean arterial pressure in both C57 and BTBR mouse models compared to compound of Formula (S)-I, MDMA and S-methamphetamine. This is consistent with predictive docking studies described above and also the further predictive IC$_{50}$ studies carried out by the Applicant, which indicated that (S)-I binds more strongly to the 5-HT$_{2B}$ receptor compared to (R)-I.

In social testing studies, (R)-I was shown to elicit similar pro-social responses compared to MDMA in both C57 and BRTB mouse models but at a lesser dose compared to MDMA suggesting that (R)-I is a more potent drug compared to MDMA in regard to pro-social response. Moreover, (R)-I was shown to demonstrate social preference without locomotor stimulant effects in both C57 and BRTB mouse models.

Accordingly, the Applicant has shown that (R)-I demonstrates social-preference comparable to MDMA but at lower doses, and advantageously with reduced adverse effects (as shown in core body temperature, locomotor activity and cardiovascular studies) especially at doses up to about 5.6 mg/kg in the mice strains tested.

The compound of Formula (R)-I is useful for treating diseases, disorders or conditions treatable by activating a serotonin receptor such as 5-HT$_{2A}$. Therefore, the compounds of the present application are useful as medicaments. Accordingly, the application also includes a compound of the application for use as a medicament.

Accordingly, the present application includes a method of treating a disease, disorder or condition treatable by activation of a serotonin receptor comprising administering an enantiomerically pure compound of Formula (R)-I or a pharmaceutically acceptable salt and/or solvate thereof to a subject in need thereof.

The present application also includes a use of an enantiomerically pure compound of Formula (R)-I or a pharmaceutically acceptable salt and/or solvate thereof for treatment of a disease, disorder or condition treatable by activation of a serotonin receptor as well as a use of an enantiomerically pure compound of Formula (R)-I or a pharmaceutically acceptable salt and/or solvate thereof for the preparation of a medicament for treatment of a disease, disorder or condition treatable by activation of a serotonin receptor. The application further includes an enantiomerically pure compound of Formula (R)-I or a pharmaceutically acceptable salt and/or solvate thereof of the application for use in treating a disease, disorder or condition treatable by activation of a serotonin receptor.

In some embodiments, the serotonin receptor is 5-HT$_{2A}$. Accordingly, the present application includes a method for activating a 5-hydroxytryptamine 2A receptor (5-HT$_{2A}$) in a cell, either in a biological sample or in a patient, comprising administering an enantiomerically pure compound of Formula (R)-I or a pharmaceutically acceptable salt and/or solvate thereof to the cell. The application also includes an enantiomerically pure compound of Formula (R)-I or a salt and/or solvate thereof for activating 5-HT$_{2A}$ in a cell as well as a use of an enantiomerically pure compound of Formula (R)-I or a pharmaceutically acceptable salt and/or solvate thereof for the preparation of a medicament for activating 5-HT$_{2A}$ in a cell. The application further includes an enantiomerically pure compound of Formula (R)-I or a pharmaceutically acceptable salt and/or solvate thereof for use in activating 5-HT$_{2A}$ in a cell.

The present application also includes a method of treating a disease, disorder or condition treatable by activation of 5-HT$_{2A}$ comprising administering an enantiomerically pure compound of Formula (R)-I or a pharmaceutically acceptable salt and/or solvate thereof to a subject in need thereof. The present application also includes a use of an enantiomerically pure compound of Formula (R)-I or a pharmaceutically acceptable salt and/or solvate thereof for treatment of a disease, disorder or condition treatable by activation of 5-HT$_{2A}$ as well as a use of an enantiomerically pure compound of Formula (R)-I or a pharmaceutically acceptable salt and/or solvate thereof for the preparation of a medicament for treatment of a disease, disorder or condition treatable by activation of 5-HT$_{2A}$. The application further includes an enantiomerically pure compound of Formula (R)-I or a salt and/or solvate thereof for use in treating a disease, disorder or condition treatable by activation of 5-HT$_{2A}$.

In some embodiments, treatment with the enantiomerically pure compound of Formula (R)-I or a pharmaceutically acceptable salt and/or solvate thereof comprises a reduced risk of adverse side effects compared to a treatment with racemic 2-[(2H-1,3-benzodioxol-5-yl)methyl]pyrrolidine (i.e. compound of Formula (R/S)-I) or a treatment with an enantiomerically pure compound of Formula (S)-I.

In some embodiments, treatment with the enantiomerically pure compound of Formula (R)-I or a pharmaceutically acceptable salt and/or solvate thereof comprises a reduced risk of adverse side effects compared to a treatment with racemic 2-[(2H-1,3-benzodioxol-5-yl)methyl]pyrrolidine (i.e. compound of Formula (R/S)-I).

In some embodiments, treatment with the enantiomerically pure compound of Formula (R)-I or a pharmaceutically acceptable salt and/or solvate thereof comprises a reduced risk of adverse side effects compared to a treatment with racemic 3,4-methylenedioxymethamphetamine (MDMA).

In some embodiments, the adverse side effects are selected from one or more of neurotoxicity, hyperthermia, hypothermia, cardiotoxicity and substance use disorder. In some embodiments, the adverse side effects are selected from one or more of neurotoxicity, hyperthermia, and substance use disorder. In some embodiments, the substance use disorder is drug abuse or drug dependence. In some embodiments, the substance use disorder is drug abuse of racemic MDMA. In some embodiments, the adverse side effects is neurotoxicity.

In some embodiments, the adverse side effects is hyperthermia or hypothermia. In some embodiments, the adverse side effect is hyperthermia. In some embodiments, the adverse side effect is hypothermia.

Reports have suggested that long term use of MDMA could lead to heart valve fibroplasia and disfunction, such as valvular heart disease (VHD) (Setola et al. Mol. Pharmacol. 63:1223-1229, 2003). Therefore, in some embodiments, the adverse side effect is cardiotoxicity. In some embodiments, the cardiotoxicity is heart valve fibroplasia and disfunction. In some embodiments, the cardiotoxicity is valvular heart disease. Therefore, in some embodiments, the adverse side effect is valvular heart disease. In some embodiments, the cardiotoxicity is tachycardia or tremor.

In some embodiments, the reduced risk of adverse side effects is by binding to the 5-hydroxytryptamine 2B receptor (5-HT$_{2B}$) with less affinity compared the 5-hydroxytryptamine 2A (5-HT$_{2A}$) receptor using the enantiomerically pure compound of Formula (R)-I or salt and/or solvate thereof compared to the compound of Formula (R/S)-I or salt and/or solvate thereof or compared to an enantiomerically pure compound of Formula (S)-I or salt and/or solvate thereof.

In some embodiments, the reduced risk of adverse side effects is by providing a more balanced binding between the 5-hydroxytryptamine 2B (5-HT$_{2B}$) receptor and the 5-hydroxytryptamine 2A (5-HT$_{2A}$) receptor using the enantiomerically pure compound of Formula (R)-I or salt and/or solvate thereof compared to the compound of Formula (R/S)-I or salt and/or solvate thereof or compared to an enantiomerically pure compound of Formula (S)-I or salt and/or solvate thereof.

In some embodiments, the disease, disorder or condition that is treatable by activation of a serotonin receptor is a disease, disorder or condition that benefits from treatment with racemic MDMA, or a pharmaceutically acceptable salt and/or solvate thereof.

In some embodiments, the disease, disorder or condition that is treatable by activation of a serotonin receptor is a disease, disorder or condition that benefits from treatment with racemic MBDB, or a pharmaceutically acceptable salt and/or solvate thereof.

In some embodiments, the disease, disorder or condition that is treatable by activation of a serotonin receptor is a disease, disorder or condition that benefits from treatment with racemic MDMA and the method comprises a reduced risk of adverse side effects compared to a treatment with racemic 3,4-methylenedioxymethamphetamine (MDMA).

In some embodiments, the disease, disorder or condition that is treatable by activation of a serotonin receptor are any disease, disorder or condition that benefits from psychotherapy, including but not limited to one or more of post-traumatic stress disorder (PTSD), social anxiety disorder, depression, alcohol addiction, and eating disorders.

In some embodiments, the enantiomerically pure compound of Formula (R)-I or a pharmaceutically acceptable salt and/or solvate thereof, is administered or used in combination with psychotherapy to treat the diseases, disorders or conditions. In some embodiments, the compound of Formula (R)-I, or a pharmaceutically acceptable salt and/or solvate thereof, improves the efficacy of psychotherapy. In some embodiment, psychotherapy is for psychiatric disorders.

In some embodiments, the disease, disorder or condition that is treatable by activation of a serotonin receptor, is one or more psychiatric disorders. In some embodiments, the one or more psychiatric disorders are selected from one or more of anxiety disorders, mood disorders, developmental disorders, substance use disorders and addictions, eating disorders, personality disorders and psychotic disorders. In some embodiments, the substance use disorder is drug abuse or drug dependence.

In some embodiments, the anxiety disorder is selected from one or more of obsessive-compulsive disorder (OCD), social anxiety disorder, phobias, panic disorder and post-traumatic stress disorder (PTSD). In some embodiments, the anxiety disorder is social anxiety disorder. In some embodiments, the anxiety disorder is PTSD.

In some embodiments, the mood disorder is selected from one or both of depression and bipolar disorder.

In some embodiments, the developmental disorder is selected from one or both of autism spectrum disorder (ASD) and Asperger syndrome.

In some embodiments, the substance use disorders and addictions are selected from one or more of alcoholism, drug abuse, drug dependence and compulsive gambling. In some embodiments, the drug dependence is opioid dependence. In some embodiments, the substance use disorder is opioid use disorder.

In some embodiments, the eating disorder is selected from anorexia and bulimia.

In some embodiments, the personality disorder is selected from borderline personality disorder and dependent personality disorder In some embodiments, the psychotic disorders are selected from schizophrenia and other disorders that cause detachment from reality.

In some embodiments, the one or more psychiatric disorders are selected from one or more of autism spectrum disorder (ASD), depression and drug dependence. In some embodiments, the depression is clinical depression, for example, in palliative care subjects.

In some embodiments, the one or more psychiatric disorders are selected from post-traumatic stress disorder (PTSD), eating disorder and alcoholism. In some embodiments, the one or more psychiatric disorders is post-traumatic stress disorder (PTSD).

In some embodiments, the one or more psychiatric disorders are selected from autism spectrum disorder (ASD), depression and drug dependence. In some embodiments, the depression is clinical depression, for example, in palliative care subjects. In some embodiments, the substance use disorder is opioid use disorder.

In some embodiments, the disease, disorder or condition treatable by activation of a serotonin receptor is an autism spectrum disorder.

In some embodiments, the autism spectrum disorder is selected from autism, Asperger's syndrome, childhood disintegrative disorder, Rett syndrome, and pervasive developmental disorder not otherwise specified.

In some embodiments, the enantiomerically pure compound of Formula (R)-I, or a pharmaceutically acceptable salt and/or solvate thereof, is administered before, during and/or after psychotherapy. In some embodiments, the enantiomerically pure compound of Formula (R)-I, or a pharmaceutically acceptable salt and/or solvate thereof, is administered during and/or after the psychotherapy.

In some embodiments, the psychotherapy is selected from behavior psychotherapy, exposure-based psychotherapy, cognitive psychotherapy, and psycho-dynamically oriented psychotherapy.

In some embodiments, the disease, disorder or condition that is treatable by activation of a serotonin receptor, is any disease, disorder or condition that benefits from treatment with L-3,4-dihydroxyphenylalanine (L-DOPA).

In some embodiments, the enantiomerically pure compound of Formula (R)-I or a pharmaceutically acceptable salt and/or solvate thereof, is administered or used in combination with L-DOPA to treat the disease, disorder or condition that benefits from treatment with L-DOPA. In some embodiments, the enantiomerically pure compound of Formula (R)-I or a pharmaceutically acceptable salt and/or solvate thereof improves the efficacy of L-DOPA. In some embodiments, the enantiomerically pure compound of Formula (R)-I or a pharmaceutically acceptable salt and/or solvate thereof is administered or used in combination with L-DOPA to improve the efficacy of L-DOPA.

In some embodiments, the disease, disorder or condition that benefits from treatment with L-DOPA is Parkinson's Disease.

The present application also includes a method for treating Parkinson's Disease comprising administering an enantiomerically pure of compound of Formula (R)-I or a pharmaceutically acceptable salt and/or solvate thereof to a subject in need thereof.

The present application further includes a use of an enantiomerically pure compound of Formula (R)-I, or a pharmaceutically acceptable salt and/or solvate thereof for treating Parkinson's Disease, a use of an enantiomerically pure compound of Formula (R)-I, or a pharmaceutically acceptable salt and/or solvate thereof for preparation of a medicament for treating Parkinson's Disease, as well as enantiomerically pure compound of Formula (R)-I or a pharmaceutically acceptable salt and/or solvate thereof for use to treat Parkinson's Disease.

In some embodiments, the enantiomerically pure compound of Formula (R)-1, or a pharmaceutically acceptable salt and/or solvate thereof is administered or used in combination with L-DOPA to treat Parkinson's Disease. In some embodiments, the enantiomerically pure compound of Formula (R)-I, or a pharmaceutically acceptable salt and/or solvate thereof improves the efficacy of L-DOPA for treating Parkinson's Disease. In some embodiments, the enantiomerically pure compound of Formula (R)-I, or a pharmaceutically acceptable salt and/or solvate thereof is administered or used in combination with L-DOPA to improve the efficacy of L-DOPA for treating Parkinson's Disease.

In some embodiments, the enantiomerically pure compound of Formula (R)-1, or a pharmaceutically acceptable salt and/or solvate thereof improves the efficacy of L-DOPA by decreasing L-DOPA-induced dyskinesia.

Therefore, in some embodiments, the disease, disorder or condition that benefits from treatment with a racemic MDMA or a pharmaceutically acceptable salt and/or solvate thereof is dyskinesia. In some embodiments, the dyskinesia is L-DOPA-induced dyskinesia.

In some embodiments, the enantiomerically pure compound of Formula (R)-1, or a pharmaceutically acceptable salt and/or solvate thereof improves the efficacy of L-DOPA by increasing the duration of antiparkinsonian benefits of L-DOPA (e.g. ON-time). In some embodiments, the enantiomerically pure compound of Formula (R)-I, or a pharmaceutically acceptable salt and/or solvate thereof improves the efficacy of L-DOPA by increasing the duration of anti-parkinsonian benefits of L-DOPA without disabling dyskinesia.

In some embodiments, the enantiomerically pure compound of Formula (R)-1, or a pharmaceutically acceptable salt and/or solvate thereof improves the efficacy of L-DOPA by decreasing L-DOPA-induced Parkinson disease psychosis.

Therefore, in some embodiments, the disease, disorder or condition that benefits from treatment with a racemic MDMA or a pharmaceutically acceptable salt and/or solvate thereof is L-DOPA-induced Parkinson disease psychosis.

By "decreasing L-DOPA-induced dyskinesia" or "decreasing L-DOPA-induced Parkinson disease psychosis" it is meant any diminishment of extent, stabilized (i.e., not worsening) state, delay or slowing of progression, amelioration or palliation, and remission (whether partial or total), whether detectable or undetectable of dyskinesia in the presence of the enantiomerically pure compound of Formula (R)-I, or a pharmaceutically acceptable salt and/or solvate thereof compared to otherwise identical conditions except in the absence of the enantiomerically pure compound of Formula (R)-I, or a pharmaceutically acceptable salt and/or solvate thereof.

By "increasing the duration of antiparkinsonian benefits of L-DOPA" it is meant any increase in the duration of antiparkinsonian benefits of L-DOPA compared to otherwise identical conditions except in the absence of the enantiomerically pure compound of Formula (R)-I, or a pharmaceutically acceptable salt and/or solvate thereof.

By "increasing the duration of antiparkinsonian benefits of L-DOPA without disabling dyskinesia" it is meant any increase in the duration of antiparkinsonian benefits of L-DOPA without disabling dyskinesia compared to otherwise identical conditions except in the absence of the enantiomerically pure compound of Formula (R)-I, or a pharmaceutically acceptable salt and/or solvate thereof.

It would be appreciated by a person skilled in the art that methods for the assessment of L-DOPA induced dyskinesia and/or psychosis are well known in the art, such as those found, for example, in Fox et al. 2006 Arch Neurol 63:1343-1344; Gomez-Ramirez et al. 2006, Mov Disord 21:839-846; Visanji et al. 2006, Mov Disord 21:1879-1891; Huot et al. Journal of Neuroscience, 2011, 31 (19) 7190-7198, and Fox et al. 2010 Can J Neurol Sci 37:86-95).

The Applicant has shown that the enantiomerically pure compound of Formula (R)-I, or a pharmaceutically acceptable salt and/or solvate thereof promotes pro-social behaviour in in vivo in both C57 mice (a general population mouse model) and BRTB mice (a mouse model of autism spectrum disorders). (R)-I was also shown to elicit the pro-social effect at a lesser dose compared to MDMA. It has further been shown that the enantiomerically pure compound of Formula (R)-I, or a pharmaceutically acceptable salt and/or solvate thereof does not influence locomotor activity in mice models in both C57 and BRTB mouse models. The Applicant has further shown that the enantiomerically pure compound of Formula (R)-I, or a pharmaceutically acceptable salt and/or solvate thereof does not elicit significant effects on core temperature. Further, the Applicant has shown that the enantiomerically pure compound of Formula (R)-I, or a pharmaceutically acceptable salt and/or solvate thereof has lower impact on cardiovascular events compared to compound of Formula (S)-I, (racemic) MDMA and methamphetamine.

Accordingly, the present application also includes a method of treating one or more signs or symptoms of a disease, disorder or condition that is treatable by activation of a serotonin receptor comprising administering an enantiomerically pure compound of Formula (R)-I, or a pharmaceutically acceptable salt and/or solvate thereof to a subject in need thereof.

The present application further includes a use of an enantiomerically pure compound of Formula (R)-I, or a pharmaceutically acceptable salt and/or solvate thereof for treating one or more signs or symptoms of a disease, disorder or condition that is treatable by activation of a serotonin receptor, use of an enantiomerically pure compound of Formula (R)-I, or a pharmaceutically acceptable salt and/or solvate thereof for preparation of a medicament for treating one or more signs or symptom of a disease, disorder or condition that is treatable by activation of a serotonin receptor, as well an enantiomerically pure compound of Formula (R)-I, or a pharmaceutically acceptable salt and/or solvate thereof for use to treat one or more signs or symptom of a disease, disorder or condition that is treatable by activation of a serotonin receptor.

In some embodiments, at least one sign or symptom of the disease, disorder or condition that is treatable by activation of a serotonin receptor is reduced following the administration of the enantiomerically pure compound of Formula (R)-I, or a pharmaceutically acceptable salt and/or solvate thereof.

Therefore, in some embodiments, the methods and uses provided herein reduce at least one sign or symptom of the disease, disorder or condition that is treatable by activation of a serotonin receptor. In some embodiments, the methods and uses provided herein reduce at least one sign or symptom of a disease, disorder or condition that is treatable by activation of a serotonin receptor by about 5% to about 100%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, or more, compared to treatment without the enantiomerically pure compound of Formula (R)-I, or a pharmaceutically acceptable salt and/or solvate thereof.

In some embodiments, the sign or symptom of the disease, disorder or condition that is treatable by activation of a serotonin receptor is reduced or eliminated in the subject within about 1 hour, about 2 hours, about 3 hours, about 6 hours, about 12 hours, about 24 hours, about 48 hours, about 3 days, about 1 week, about 2 weeks, about 3 weeks, about 4 weeks, about 5 weeks, about 6 weeks, about 7 weeks, about 8 weeks, or about 3 months following administration the enantiomerically pure compound of Formula (R)-I, or a pharmaceutically acceptable salt and/or solvate thereof.

In some embodiments, the sign or symptom of the disease, disorder or condition that is treatable by activation of a serotonin receptor is reduced or eliminated in the subject for a period of about 1 day, about 3 days, about 7 days, about 10 days, about 2 weeks, about 3 weeks, about 4 weeks, about 5 weeks, about 6 weeks, about 7 weeks, about 8 weeks, about 3 months, about 4 months, about 5 months, about 6 months, about 7 months, about 8 months, about 9 months, about 10 months, about 11 months, about 12 months, about 18 months, about 24 months, or about 48 months following administration of the enantiomerically pure compound of Formula (R)-I, or a pharmaceutically acceptable salt and/or solvate thereof.

By "reduce at least one sign or symptom of the disease, disorder or condition that is treatable by activation of a serotonin receptor" it is meant any decrease or reduction in the sign or symptom of the disease, disorder or condition compared to otherwise identical conditions except in the absence of the enantiomerically pure compound of Formula (R)-I, or a pharmaceutically acceptable salt and/or solvate thereof.

In some embodiments, the sign or symptom of the disease, disorder or condition that is treatable by activation of a serotonin receptor is neurotoxicity, hyperthermia, hypothermia, cardiotoxicity and substance use disorder.

In some embodiments, the disease, disorder or condition that is treatable by activation of a serotonin receptor is autism spectrum disorder, and the present application also includes a method of treating one or more signs or symptoms of an autism spectrum disorder comprising administering a therapeutically effective amount of the enantiomerically pure compound of Formula (R)-I, or a pharmaceutically acceptable salt and/or solvate thereof to a subject in need thereof.

The present application further includes a use of the enantiomerically pure compound of Formula (R)-I, or a pharmaceutically acceptable salt and/or solvate thereof for treating one or more signs or symptoms of an autism spectrum disorder, a use of the enantiomerically pure compound of Formula (R)-I, or a pharmaceutically acceptable salt and/or solvate thereof for preparation of a medicament for treating one or more signs or symptoms of an autism spectrum disorder, as well as the enantiomerically pure compound of Formula (R)-I, or a pharmaceutically acceptable salt and/or solvate thereof for use to treat one or more signs or symptoms of an autism spectrum disorder.

In some embodiments, the one or more signs or symptoms of an autism spectrum disorder are selected from general anxiety, clinical anxiety, irritability, inappropriate speech, stereotypy, social withdrawal, repetitive behavior, and hyperactivity.

In some embodiments, the one or more signs or symptoms of an autism spectrum disorder is selected from stereotypy and social withdrawal. In some embodiments, the one or more sign or symptoms of an autism spectrum disorder is stereotypy. In some embodiments, the one or more signs or symptoms of an autism spectrum disorder is social withdrawal. Accordingly, in some embodiments, the enantiomerically pure compound of Formula (R)-I, or a pharmaceutically acceptable salt and/or solvate thereof is for use to promote prosocial activity The present application further comprises treating one or more symptoms of an autism spectrum disorder while reducing adverse side effects of treatment with a racemic MDMA or (R/S)-I comprising administering or using the enantiomerically pure compound of Formula (R)-I, or a pharmaceutically acceptable salt and/or solvate thereof to a subject in need thereof.

In some embodiments, the one or more symptoms of an autism spectrum disorder is selected from stereotypy and social withdrawal and the adverse side effect is selected from hyperthermia, stereotypy and neurotoxicity. In some embodiments, the one or more symptoms of an autism spectrum disorder is selected from stereotypy and social withdrawal and adverse side effect is selected from hyperthermia and neurotoxicity. In some embodiments, the one or more symptoms of an autism spectrum disorder is selected from stereotypy and social withdrawal and the adverse side effect is selected from hyperthermia.

In some embodiments, the autistic spectrum disorder is as defined by DSM-IV, wherein the one or more symptoms is selected from: (i) qualitative impairment in social interaction; (ii) qualitative impairment in communication; and (iii) restricted repetitive and stereotyped patterns of behaviour, interest and activities.

In some embodiments, the one or more symptoms is selected from qualitative impairment in social interaction.

In some embodiments, the qualitative impairment in social interaction includes one or more of: marked impairment in the use of multiple nonverbal behaviours, including eye-to-eye gaze, facial expression, body postures, and gestures to regulate social interaction; failure to develop peer relationships appropriate to developmental level; a lack of spontaneous seeking to share enjoyment, interests, or achievements with other people (e.g., by a lack of showing, bringing, or pointing out objects of interest); and lack of social or emotional reciprocity.

In some embodiments, the qualitative impairment in communication include one or more of: delay in, or total lack of, the development of spoken language (not accompanied by an attempt to compensate through alternative modes of communication such as gesture or mime); in individuals with adequate speech, marked impairment in the ability to initiate or sustain a conversation with others; stereotyped and repetitive use of language or idiosyncratic language; and lack of varied, spontaneous make-believe play or social imitative play appropriate to developmental level.

In some embodiments, the restricted repetitive and stereotyped patterns of behaviour, interest and activities include one or more of: encompassing preoccupation with one or more stereotyped and restricted patterns of interest that is abnormal either in intensity or focus; apparently inflexible adherence to specific, non-functional routines or rituals; stereotyped and repetitive motor mannerisms (e.g., hand or finger flapping or twisting or complex whole-body movements); and persistent preoccupation with parts of objects.

In some embodiments, the disease, disorder or condition that is treatable by activation of a serotonin receptor is an anxiety disorder, and the present application also includes a method of treating one or more signs or symptoms of an anxiety disorder comprising administering a therapeutically effective amount of the enantiomerically pure compound of Formula (R)-I, or a pharmaceutically acceptable salt and/or solvate thereof to a subject in need thereof.

The present application further includes a use of the enantiomerically pure compound of Formula (R)-I, or a pharmaceutically acceptable salt and/or solvate thereof for treating one or more signs or symptoms of an anxiety disorder, a use of the enantiomerically pure compound of Formula (R)-I, or a pharmaceutically acceptable salt and/or solvate thereof for preparation of a medicament for treating one or more signs or symptoms of an anxiety disorder, as well as the enantiomerically pure compound of Formula (R)-I, or a pharmaceutically acceptable salt and/or solvate thereof for use to treat one or more signs or symptoms of an anxiety disorder.

In some embodiments, the one or more signs or symptoms of the anxiety disorder is measured according to a diary assessment, an assessment by a clinician or caregiver, or a clinical scale.

In some embodiments, the one or more signs or symptoms of the anxiety disorder is fear including fear of social interaction or situations, avoidance of anxiety triggers, feelings of stress, easily agitated, catastrophizing, nervousness, tachycardia, heart palpitations, tremor, fatigue, worry, irritability, obsession, compulsion, muscle tension, sweating, dizziness, shortness of breath, disturbed sleep, or combinations thereof Accordingly, in some embodiments, the enantiomerically pure compound of Formula (R)-I, or a pharmaceutically acceptable salt and/or solvate thereof is for use to promote prosocial activity in a subject having the anxiety disorder.

In some embodiments, the anxiety disorder is selected from one or more of obsessive-compulsive disorder (OCD), social anxiety disorder, phobias, panic disorder and post-traumatic stress disorder (PTSD) as described above. In some embodiments, the anxiety disorder is social anxiety disorder.

In some embodiments, the enantiomerically pure compound of Formula (R)-I, or a pharmaceutically acceptable salt and/or solvate thereof is administered or use as a second agent or "add-on" therapy.

In some embodiments, the enantiomerically pure compound of Formula (R)-I comprises greater than 99% by weight of the compound of Formula (R)-I and less than 1% by weight of the compound of Formula (S)-I. In some embodiments, the enantiomerically pure compound of Formula (R)-I comprises 99.1%, 99.2%, 99.3%, 99.4%, 99.5%, 99.6%, 99.7%, 99.8%, 99.9%, 99.91%, 99.92%, 99.93%, 99.94%, 99.95%, 99.96%, 99.97%, 99.98%, 99.9% or 100% by weight of the compound of Formula (R)-I and 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, or 0% respectively less by weight of the compound of Formula (S)-I.

In some embodiments, the enantiomerically pure compound of Formula (R)-I comprises an enantiomeric excess (ee) of 98% or more. In some embodiments, the enantiomerically pure compound of Formula (R)-I comprises comprise an enantiomeric excess (ee) of 98% to 100%. In some embodiments, the enantiomerically pure compound of Formula (R)-I comprises comprise an enantiomeric excess (ee) of 98%, 98.1%, 98.2%, 98.3% 98.4%, 98.5%, 98.6%, 98.7%, 98.8%, 98.9%, 98.9%, 99%, 99.1%, 99.2%, 99.3%, 99.4%, 99.5%, 99.7%, 99.8%, 99.9% or about 100%.

In some embodiments, the enantiomeric purity of the compound is determined by optical rotation.

In some embodiments, the enantiomerically pure compound of Formula (R)-I, or a pharmaceutically acceptable salt and/or solvate thereof is used or administered in an amount that is a quantity sufficient to, when administered to a subject, effect beneficial or desired results, including clinical results, and, as such, the amount depends upon the context in which it is being applied. Therefore, the amount administered or used is that amount of the compound that is sufficient to treat, prevent or inhibit diseases or conditions. In some embodiments, the amount of the compound of Formula (R)-I, or a pharmaceutically acceptable salt and/or solvate thereof, administered will vary depending upon factors, such as the pharmaceutical formulation, the route of administration, the type of condition, disease or disorder, the identity of the subject being treated, and the like, but can nevertheless be routinely determined by one skilled in the art. In an embodiment, the amount administered or used is one that, following treatment therewith, manifests as an improvement in or reduction of any disease, disorder or condition symptom, in particular compared to the disease, disorder or condition symptom without treatment.

In an embodiment, the enantiomerically pure compound of Formula (R)-I, or a pharmaceutically acceptable salt and/or solvate thereof, or a pharmaceutically acceptable salt and/or solvate thereof, is administered at least once a week. However, in another embodiment, the enantiomerically pure compound of Formula (R)-I, or a pharmaceutically acceptable salt and/or solvate thereof, is administered to the subject from about one time per two weeks, three weeks or one month. In another embodiment, the enantiomerically pure compound of Formula (R)-I, or a pharmaceutically acceptable salt and/or solvate thereof, is administered about one time per week to about once daily. In another embodiment, the enantiomerically pure compound of Formula (R)-I, or a pharmaceutically acceptable salt and/or solvate thereof, is administered 2, 3, 4, 5 or 6 times daily. The length of the treatment period depends on a variety of factors, such as the severity of the disease, disorder or condition, the age of the subject, the concentration and/or the activity of the enantiomerically pure compound of Formula (R)-I, or a pharmaceutically acceptable salt and/or solvate thereof, and/or a combination thereof. It will also be appreciated that the effective dosage of the enantiomerically pure compound of Formula (R)-I, or a pharmaceutically acceptable salt and/or solvate thereof, used for the treatment may increase or decrease over the course of a particular treatment regime.

Changes in dosage may result and become apparent by standard diagnostic assays known in the art. In some instances, chronic administration is required. For example, the enantiomerically pure compound of Formula (R)-I or a pharmaceutically acceptable salt and/or solvate thereof, is administered to the subject in an amount and for duration sufficient to treat the subject.

In an embodiment, the subject is a mammal. In another embodiment, the subject is human. In an embodiment, the subject is a non-human animal. In an embodiment, the subject is canine. In an embodiment, the subject is feline. Accordingly, the methods and uses of the present application are directed to both human and veterinary diseases, disorders and conditions.

The enantiomerically pure compound of Formula (R)-I or a pharmaceutically acceptable salt and/or solvate thereof, is either used alone or in combination with other known agents useful for treating a disease, disorder or condition treatable by activation of a serotonin receptor.

In some embodiments, when used in combination with other agents useful in treating a disease, disorder or condition treatable by activation of a serotonin receptor, it is an embodiment that the enantiomerically pure compound of Formula (R)-I, or a pharmaceutically acceptable salt and/or solvate thereof, is administered contemporaneously with those agents. As used herein, "contemporaneous administration" of two substances to a subject means providing each of the two substances so that they are both active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present application that a combination of agents is administered to a subject in a non-contemporaneous fashion.

The dosage of the enantiomerically pure compound of Formula (R)-I, or a pharmaceutically acceptable salt and/or solvate thereof, varies depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the enantiomerically pure compound of Formula (R)-I, or a pharmaceutically acceptable salt and/or solvate thereof, in the subject to be treated. One of skill in the art can determine the appropriate dosage based on the above factors.

As a representative example, oral dosages of o the enantiomerically pure compound of Formula (R)-I, or a pharmaceutically acceptable salt and/or solvate thereof will range between about 1 mg per day to about 50 mg per day for an adult, suitably about 1 mg per day to about 40 mg per day, more suitably about 2 mg per day to about 30 mg per day. In some embodiments, the subject weights 55 to 65 kg, suitably 60 kg. For oral administration, a representative amount is from about 0.01 mg/kg to about 1 mg/kg, about 0.05 mg/kg to about 1 mg/kg, about 0.05 mg/kg to about 0.75 mg/kg or about 0.05 mg/kg to about 0.5 mg/kg.

In some embodiments of the application the pharmaceutical compositions of enantiomerically pure compound of Formula (R)-I, or a pharmaceutically acceptable salt and/or solvate thereof of the application are used in the treatment of any of the diseases, disorders or conditions described herein as described below.

(ii) Methods and Uses of the Compositions of the Application

In some embodiments, the compositions of the application, including pharmaceutical compositions, are useful for treating a disease, disorder or condition treatable by activating a serotonin receptor such as 5-HT$_{2A}$.

Accordingly, the present application includes a method of treating a disease, disorder or condition treatable by activation of a serotonin receptor comprising administering a therapeutically effective amount of a composition of the application to a subject in need thereof.

The present application also includes a use of a composition of the application for treatment of a disease, disorder or condition treatable by activation of a serotonin receptor as well as a use of a composition of the application for the preparation of a medicament for treatment of a disease, disorder or condition treatable by activation of a serotonin receptor. The application further includes a composition of the application for use in treating a disease, disorder or condition treatable by activation of a serotonin receptor.

In some embodiments, the serotonin receptor is 5-HT$_{2A}$. Accordingly, the present application includes a method for activating a 5-hydroxytryptamine 2A receptor (5-HT$_{2A}$) in a cell, either in a biological sample or in a patient, comprising administering comprises administering a one or more compositions of the application to a subject in need thereof.

The application also includes a use one or more compositions of the application for activating 5-HT$_{2A}$ in a cell as well as a use of one or more compositions of the application for the preparation of a medicament for activating 5-HT$_{2A}$ in a cell. The application further includes one or more compositions of the application for use in activating 5-HT$_{2A}$ in a cell.

The present application also includes a method of treating a disease, disorder or condition treatable by activation of 5-HT$_{2A}$ comprising administering a composition of the application to a subject in need thereof. The present application also includes a use of a composition of the application for treatment of a disease, disorder or condition treatable by activation of 5-HT$_{2A}$ as well as a use of a composition of the application for the preparation of a medicament for treatment of a disease, disorder or condition treatable by activation of 5-HT$_{2A}$. The application further includes a composition of the application for use in treating a disease, disorder or condition treatable by activation of 5-HT$_{2A}$.

In some embodiments, the disease, disorder or condition treatable by activation of 5-HT$_{2A}$ is any disease, disorder or condition that benefits from treatment with a racemic MDMA.

In some embodiments, treatment with the composition of the application comprises a reduced risk of adverse side effects compared to a treatment with racemic methylenedioxyphenethylamine (MDMA).

In some embodiments, treatment with the composition of the application comprises a reduced risk of adverse side effects compared to treatment with racemic 2-[(2H-1,3-benzodioxol-5-yl)methyl]pyrrolidine (i.e. compound of Formula (R/S)-I).

In some embodiments, treatment with the composition of the application comprises a reduced risk of adverse side effects compared to treatment with racemic 2-[(2H-1,3-benzodioxol-5-yl)methyl]pyrrolidine (i.e. compound of Formula (R/S)-I) or a treatment with an enantiomerically pure compound of Formula (S)-I.

In some embodiments, the adverse side effects are selected from one or more of neurotoxicity, hyperthermia, hypothermia, cardiotoxicity and substance use disorder. In some embodiments, the adverse side effects are selected from one or more of neurotoxicity, hyperthermia, and substance use disorder. In some embodiments, the substance use disorder is drug abuse or drug dependence. In some embodiments, the substance use disorder is drug abuse of racemic MDMA.

In some embodiments, the adverse side effects is hyperthermia or hypothermia. In some embodiments, the adverse side effect is hyperthermia. In some embodiments, the adverse side effect is hypothermia.

Reports have suggested that long term use of MDMA could lead to heart valve fibroplasia and disfunction, such as valvular heart disease (VHD) (Setola et al. Mol. Pharmacol. 63:1223-1229, 2003). Therefore, in some embodiments, the adverse side effects is cardiotoxicity. In some embodiments, the cardiotoxicity is heart valve fibroplasia and disfunction. In some embodiments, the cardiotoxicity is valvular heart disease. Therefore, in some embodiments, the adverse side effect is valvular heart disease. In some embodiments, the cardiotoxicity is tachycardia or tremor.

In some embodiments, the reduced risk of adverse side effects is by binding to the 5-hydroxytryptamine 2B (5-HT$_{2B}$) receptor with less affinity compared to the 5-hydroxytryptamine 2A (5-HT$_{2A}$) receptor using the compositions of the application compared to a composition comprising the racemic compound of Formula (R/S)-I.

In some embodiments, the reduced risk of adverse side effects is by providing a more balanced binding between the 5-hydroxytryptamine 2B (5-HT$_{2B}$) receptor and the 5-hydroxytryptamine 2A (5-HT$_{2A}$) receptor using the compositions of the application compared to a composition comprising the racemic compound of Formula (R/S)-I.

In some embodiments, the disease, disorder or condition that is treatable by activation of a serotonin receptor is a disease, disorder or condition that benefits from treatment with racemic MDMA, or a pharmaceutically acceptable salt and/or solvate thereof.

In some embodiments, the disease, disorder or condition that is treatable by activation of a serotonin receptor is a disease, disorder or condition that benefits from treatment with racemic MBDB, or a pharmaceutically acceptable salt and/or solvate thereof.

In some embodiments, the disease, disorder or condition that is treatable by activation of a serotonin receptor is a disease, disorder or condition that benefits from treatment with racemic MDMA and the method comprises a reduced risk of adverse side effects compared to a treatment with racemic 3,4-methylenedioxymethamphetamine (MDMA).

In some embodiments, the disease, disorder or condition that is treatable by activation of a serotonin receptor, are any disease, disorder or condition that benefits from psychotherapy, including but not limited to one or more of post-traumatic stress disorder (PTSD), social anxiety disorder, depression, alcohol addiction, and eating disorders.

In some embodiments, the one or more compositions are administered or used in combination with psychotherapy to treat the diseases, disorders or conditions. In some embodiments, the one or more compositions improve the efficacy of psychotherapy. In some embodiment, the psychotherapy is for psychiatric disorders.

In some embodiments, the disease, disorder or condition that is treatable by activation of a serotonin receptor, are one or more psychiatric disorders. In some embodiments, the one or more psychiatric disorders are selected from one or more of anxiety disorders, mood disorders, developmental disorders, substance use disorders and addictions, eating disorders, personality disorders and psychotic disorders. In some embodiments, the substance use disorder is drug abuse or drug dependence.

In some embodiments, the anxiety disorder is selected from one or more of obsessive-compulsive disorder (OCD), social anxiety disorder, phobias, panic disorder and post-traumatic stress disorder (PTSD). In some embodiments, the anxiety disorder is social anxiety disorder. In some embodiments, the anxiety disorder is PTSD.

In some embodiments, the mood disorder is selected from one or both of depression and bipolar disorder.

In some embodiments, the developmental disorder is selected from one or both of autism spectrum disorder (ASD) and Asperger syndrome.

In some embodiments, the substance use disorders and addictions are selected from one or more of alcoholism, drug abuse, drug dependence and compulsive gambling. In some embodiments, the drug dependence is opioid dependence. In some embodiments, the substance use disorder is opioid use disorder.

In some embodiments, the eating disorder is selected from anorexia and bulimia.

In some embodiments, the personality disorder is selected from borderline personality disorder and dependent personality disorder In some embodiments, the psychotic disorders are selected from schizophrenia and other disorders that cause detachment from reality.

In some embodiments, the one or more psychiatric disorders are selected from one or more of autism spectrum disorder (ASD), depression and drug dependence. In some embodiments, the depression is clinical depression, for example, in palliative care subjects. In some embodiments, the substance use disorder is opioid use disorder.

In some embodiments, the disease, disorder or condition treatable by activation of $5\text{-HT}_{2A}$ is an autism spectrum disorder.

In some embodiments, the autism spectrum disorder is selected from autism, Asperger's syndrome, childhood disintegrative disorder, Rett syndrome, and pervasive developmental disorder not otherwise specified.

In some embodiments, the one or more psychiatric disorders are selected from post-traumatic stress disorder (PTSD), eating disorder and alcoholism. In some embodiments, the one or more psychiatric disorders is post-traumatic stress disorder (PTSD).

In some embodiments, the one or more psychiatric disorders are selected from autism spectrum disorder (ASD), depression, and substance use disorder. In some embodiments, the depression is clinical depression, for example, in palliative care subjects. In some embodiments, the substance use disorder is opioid use disorder.

In some embodiments, the composition of the application is administered before, during and/or after psychotherapy. In some embodiments, the composition of the application is administered during and/or after the psychotherapy.

In some embodiments, the psychotherapy is selected from behavior psychotherapy, exposure-based psychotherapy, cognitive psychotherapy, and psycho-dynamically oriented psychotherapy.

In some embodiments, the disease, disorder or condition that is treatable by activation of a serotonin receptor, is any a disease, disorder or condition that benefits from treatment with L-3,4-dihydroxyphenylalanine (L-DOPA).

In some embodiments, the composition is administered or used in combination with L-DOPA to treat the disease, disorder or condition that benefits from treatment with L-DOPA. In some embodiments, the composition improves the efficacy of L-DOPA. In some embodiments, the composition is administered or used in combination with L-DOPA to improve the efficacy of L-DOPA.

In some embodiments, the disease, disorder or condition that benefits from treatment with L-DOPA is Parkinson's Disease.

The present application also includes a method for treating Parkinson's Disease comprising administering one or more compositions of the application to a subject in need thereof.

The present application further includes a use of one or more compositions of the application for treating Parkinson's Disease, a use of one or more compositions of the application for preparation of a medicament for treating Parkinson's Disease, as well as one or more compositions of the application for use to treat Parkinson's Disease.

In some embodiments, the one or more compositions are administered or used in combination with L-DOPA to treat Parkinson's Disease. In some embodiments, the one or more compositions improve the efficacy of L-DOPA for treating Parkinson's Disease. In some embodiments, the one or more compositions are administered or used in combination with L-DOPA to improve the efficacy of L-DOPA for treating Parkinson's Disease.

In some embodiments, the one or more compositions improves the efficacy of L-DOPA by decreasing L-DOPA-induced dyskinesia.

Therefore, in some embodiments, the disease, disorder or condition that benefits from treatment with a racemic MDMA is dyskinesia. In some embodiments, the dyskinesia is L-DOPA-induced dyskinesia.

In some embodiments, the one or more compositions improves the efficacy of L-DOPA by increasing the duration of antiparkinsonian benefits of L-DOPA (e.g. ON-time). In some embodiments, the one or more compositions improves the efficacy of L-DOPA by increasing the duration of antiparkinsonian benefits of L-DOPA without disabling dyskinesia.

In some embodiments, the one or more compositions improves the efficacy of L-DOPA by decreasing L-DOPA-induced Parkinson disease psychosis.

Therefore, in some embodiments, the disease, disorder or condition that benefits from treatment with the one or more compositions of the application is L-DOPA-induced Parkinson disease psychosis.

By "decreasing L-DOPA-induced dyskinesia" or "decreasing L-DOPA-induced Parkinson disease psychosis" it is meant any diminishment of extent, stabilized (i.e., not worsening) state, delay or slowing of progression, amelioration or palliation, and remission (whether partial or total), whether detectable or undetectable of dyskinesia in the presence of one or more compositions of the application compared to otherwise identical conditions except in the absence of one or more compositions of the application.

By "increasing the duration of antiparkinsonian benefits of L-DOPA" it is meant any increase in the duration of antiparkinsonian benefits of L-DOPA compared to otherwise identical conditions except in the absence of one or more compositions of the application.

By "increasing the duration of antiparkinsonian benefits of L-DOPA without disabling dyskinesia" it is meant any increase in the duration of antiparkinsonian benefits of L-DOPA without disabling dyskinesia compared to otherwise identical conditions except in the absence of one or more compositions of the application.

It would be appreciated by a person skilled in the art that methods for the assessment of L-DOPA induced dyskinesia and/or psychosis are well known in the art, such as those found, for example, in Fox et al. 2006 Arch Neurol 63:1343-1344; Gomez-Ramirez et al. 2006, Mov Disord 21:839-846; Visanji et al. 2006, Mov Disord 21:1879-1891; Huot et al. Journal of Neuroscience, 2011, 31 (19) 7190-7198, and Fox et al. 2010 Can J Neurol Sci 37:86-95).

The Applicant has shown that the compositions of the application promote pro-social behaviour in in vivo mice models of autism spectrum disorder. It has further been shown that the compositions of the application do not influence locomotor activity in mice models of autism spectrum disorder. The Applicant has further shown that composition of the application also did not elicit significant effects on core temperature. Further, the Applicant has shown that compositions of the application had lower impact on cardiovascular events compared to a compound of Formula (S)-I, MDMA and methamphetamine.

Accordingly, the present application also includes a method of treating one or more signs or symptom of a disease, disorder or condition that is treatable by activation of a serotonin receptor comprising administering a composition of the application to a subject in need thereof.

The present application further includes a use of a composition of the application of for treating one or more signs or symptom of a disease, disorder or condition that is treatable by activation of a serotonin receptor, a use of a composition of the application for preparation of a medicament for treating one or more signs or symptoms of a disease, disorder or condition that is treatable by activation of a serotonin receptor, as well a composition of the application described above for use to treat one or more signs or symptom of a disease, disorder or condition that is treatable by activation of a serotonin receptor.

In some embodiments, at least one sign or symptom of the disease, disorder or condition that is treatable by activation of a serotonin receptor is reduced following the administration of the composition of the application.

In some embodiments, the methods and uses provided herein reduce at least one sign or symptom of a disease, disorder or condition that is treatable by activation of a serotonin receptor. In some embodiments, the methods and uses provided herein reduce at least one sign or symptom of a disease, disorder or condition that is treatable by activation of a serotonin receptor by about 5% to about 100%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, or more, compared to treatment without the composition of the application.

In some embodiments, the sign or symptom of the disease, disorder or condition that is treatable by activation of a serotonin receptor is reduced or eliminated in the subject within about 1 hour, about 2 hours, about 3 hours, about 6 hours, about 12 hours, about 24 hours, about 48 hours, about 3 days, about 1 week, about 2 weeks, about 3 weeks, about 4 weeks, about 5 weeks, about 6 weeks, about 7 weeks, about 8 weeks, or about 3 months following administration the composition of the application.

In some embodiments, the sign or symptom of the disease, disorder or condition that is treatable by activation of a serotonin receptor is reduced or eliminated in the subject for a period of about 1 day, about 3 days, about 7 days, about 10 days, about 2 weeks, about 3 weeks, about 4 weeks, about 5 weeks, about 6 weeks, about 7 weeks, about 8 weeks, about 3 months, about 4 months, about 5 months, about 6 months, about 7 months, about 8 months, about 9 months, about 10 months, about 11 months, about 12 months, about 18 months, about 24 months, or about 48 months following administration of the composition of the application.

By "reduce at least one sign or symptom of the disease, disorder or condition that is treatable by activation of a serotonin receptor" it is meant any decrease or reduction in the sign or symptom of the disease, disorder or condition compared to otherwise identical conditions except in the absence of a composition of the application.

In some embodiments, the sign or symptom of the disease, disorder or condition that is treatable by activation of a serotonin receptor is neurotoxicity, hyperthermia, hypothermia, cardiotoxicity and substance use disorder.

In some embodiments, the disease, disorder or condition that is treatable by activation of a serotonin receptor is autism spectrum disorder, and the present application also includes a method of treating one or more signs or symptoms of an autism spectrum disorder comprising administering a therapeutically effective amount of a composition of the application to a subject in need thereof.

The present application further includes a use of a composition of the application for treating one or more signs or symptoms of an autism spectrum disorder, a use of a composition of the application for preparation of a medicament for treating one or more signs or symptoms of an autism spectrum disorder, as well as a composition of the application described above for use to treat one or more signs or symptoms of an autism spectrum disorder.

In some embodiments, the one or more signs or symptoms of an autism spectrum disorder are selected from general anxiety, clinical anxiety, irritability, inappropriate speech, stereotypy, social withdrawal, repetitive behavior, and hyperactivity.

In some embodiments, the one or more signs or symptoms of an autism spectrum disorder is selected from stereotypy and social withdrawal. In some embodiments, the one or more sign or symptoms of an autism spectrum disorder is stereotypy. In some embodiments, the one or more signs or symptoms of an autism spectrum disorder is social withdrawal. Accordingly, in some embodiments, the compositions of the application are for use to promote prosocial activity The present application further comprises a method or uses of treating one or more symptoms of an autism spectrum disorder while reducing adverse side effects of treatment with a racemic MDMA or (R/S)-I In some embodiments, the one or more symptoms of an autism spectrum disorder is selected from stereotypy and social withdrawal and the adverse side effect is selected from hyperthermia, stereotypy and neurotoxicity. In some embodiments, the one or more symptoms of an autism spectrum disorder is selected from stereotypy and social withdrawal and the adverse side effect is selected from hyperthermia and neurotoxicity. In some embodiments, the one or more symptoms of an autism spectrum disorder is selected from stereotypy and social withdrawal and the adverse side effect is selected from hyperthermia.

In some embodiments, the autistic spectrum disorder is, as defined by DSM-IV, wherein the one or more symptoms is selected from: (i) qualitative impairment in social interaction; (ii) qualitative impairment in communication; and (iii) restricted repetitive and stereotyped patterns of behaviour, interest and activities.

In some embodiments, the one or more symptoms is qualitative impairment in social interaction.

In some embodiments, the qualitative impairment in social interaction includes one or more of: marked impairment in the use of multiple nonverbal behaviours, including eye-to-eye gaze, facial expression, body postures, and gestures to regulate social interaction; failure to develop peer relationships appropriate to developmental level, a lack of spontaneous seeking to share enjoyment, interests, or achievements with other people (e.g., by a lack of showing, bringing, or pointing out objects of interest); and lack of social or emotional reciprocity.

In some embodiments, the qualitative impairment in communication include one or more of: delay in, or total lack of, the development of spoken language (not accompanied by an attempt to compensate through alternative modes of communication such as gesture or mime); in individuals with adequate speech, marked impairment in the ability to initiate or sustain a conversation with others; stereotyped and repetitive use of language or idiosyncratic language; and lack of varied, spontaneous make-believe play or social imitative play appropriate to developmental level.

In some embodiments, the restricted repetitive and stereotyped patterns of behaviour, interest and activities include one or more of: encompassing preoccupation with one or more stereotyped and restricted patterns of interest that is abnormal either in intensity or focus; apparently inflexible adherence to specific, non-functional routines or rituals; stereotyped and repetitive motor mannerisms (e.g., hand or finger flapping or twisting or complex whole-body movements); and persistent preoccupation with parts of objects.

In some embodiments, the disease, disorder or condition that is treatable by activation of a serotonin receptor is an anxiety disorder, and the present application also includes a method of treating one or more signs or symptoms of an anxiety disorder comprising administering a therapeutically effective amount of the composition of the application to a subject in need thereof.

The present application further includes a use of the composition of the application for treating one or more signs or symptoms of an anxiety disorder, a use of the composition of the application for preparation of a medicament for treating one or more signs or symptoms of an anxiety disorder, as well as the composition of the application for use to treat one or more signs or symptoms of an anxiety disorder.

In some embodiments, the one or more signs or symptoms of the anxiety disorder is measured according to a diary assessment, an assessment by a clinician or caregiver, or a clinical scale.

In some embodiments, the one or more signs or symptoms of the anxiety disorder is fear including fear of social interaction or situations, avoidance of anxiety triggers, feelings of stress, easily agitated, catastrophizing, nervousness, tachycardia, heart palpitations, tremor, fatigue, worry, irritability, obsession, compulsion, muscle tension, sweating, dizziness, shortness of breath, disturbed sleep, or combinations thereof Accordingly, in some embodiments, the composition of the application is for use to promote prosocial activity in a subject having the anxiety disorder.

In some embodiments, the anxiety disorder is selected from one or more of obsessive-compulsive disorder (OCD), social anxiety disorder, phobias, panic disorder and post-traumatic stress disorder (PTSD) as described above. In some embodiments, the anxiety disorder is social anxiety disorder.

In some embodiments, the composition of the application is administered or use as a second agent or "add-on" therapy.

In some embodiments, the compositions of the application are used or administered in an amount that is a quantity sufficient to, when administered to a subject, effect beneficial or desired results, including clinical results, and, as such, the amount depends upon the context in which it is being applied. Therefore, the amount administered or used is that amount of the composition that is sufficient to treat, prevent or inhibit diseases or conditions. In some embodiments, the amount of a given composition that is used or administered will vary depending upon factors, such as the given composition(s), the pharmaceutical formulation, the route of administration, the type of condition, disease or disorder, the identity of the subject being treated, and the like, but can nevertheless be routinely determined by one skilled in the art. In an embodiment, the amount administered or used is one that, following treatment therewith, manifests as an improvement in or reduction of any disease, disorder or condition symptom, in particular compared to the disease, disorder or condition symptom without treatment.

In some embodiments, the compositions of the application are administered at least once a week. In some embodiments, the compositions of the application are administered from about one time per two weeks, three weeks or one month. In some embodiments, the compositions of the application are administered about one time per week to about once daily. In some embodiments, the compositions of the application are administered 2, 3, 4, 5 or 6 times daily. The length of the treatment period depends on a variety of factors, such as the severity of the disease, disorder or condition, the age of the subject, the concentration and/or the activity of the compositions of the application, and/or a combination thereof.

It will also be appreciated that the effective dosage of the compositions used for the treatment may increase or decrease over the course of a particular treatment regime. Changes in dosage may result and become apparent by standard diagnostic assays known in the art. In some instances, chronic administration is required. For example, the compositions are administered to the subject in an amount and for duration sufficient to treat the subject.

In some embodiments, the subject is a mammal. In some embodiments, the subject is human. In some embodiments, the subject is a non-human animal. In some embodiments, the subject is canine. In some embodiments, the subject is feline. Accordingly, the compositions, methods and uses of the present application are directed to both human and veterinary diseases, disorders and conditions. In some embodiments, the "subject in need thereof" is a subject having the disease, disorder or condition to be treated.

Compositions of the application are either used alone or in combination with other known agents useful for treating diseases, disorders or conditions treatable by activation of a serotonin receptor. When used in combination with other agents useful in treating diseases, disorders or conditions that are treatable by activation of a serotonin receptor, it is an embodiment that a composition of the application is administered contemporaneously with those agents. As used herein, "contemporaneous administration" of two substances to a subject means providing each of the two substances so that they are both active in the individual at the same time. The exact details of the administration will depend on the pharmacokinetics of the substances in the presence of each other, and can include administering the substances within a few hours of each other, or even administering one substance within 24 hours of administration of the other, if the pharmacokinetics are suitable. Design of suitable dosing regimens is routine for one skilled in the art. In particular embodiments, substances will be administered substantially simultaneously, i.e., within minutes of each other, or in a single composition that contains all substances. It is a further embodiment of the present application that a combination of agents is administered to a subject in a non-contemporaneous fashion.

The dosage of a composition of the application varies depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors. In some embodiments, a composition of the application is administered initially in a suitable dosage that is adjusted as required, depending on the clinical response.

As a representative example, oral dosages of one or more composition of the application will range between about 1 mg per day to about 50 mg per day for an adult, suitably about 1 mg per day to about 40 mg per day, more suitably about 2 mg per day to about 30 mg per day. In some embodiments, the subject weights 55 to 65 kg, suitably 60 kg. For oral administration, a representative amount is from about 0.01 mg/kg to about 1 mg/kg, about 0.05 mg/kg to about 1 mg/kg, about 0.05 mg/kg to about 0.75 mg/kg or about 0.05 mg/kg to about 0.5 mg/kg.

V. Processes of the Application

The present application includes a novel process for preparing (R)-2-[(2H-1,3-benzodioxol-5-yl)methyl]pyrrolidine ((R)-I) or (S)-2-[(2H-1,3-benzodioxol-5-yl)methyl]pyrrolidine ((S)-I). In particular, the application includes a stereoselective and efficient two step process for preparing a compound of (R)-I or (S)-I using an aryl acylation reaction followed by a carbonyl reduction.

Accordingly, the present application includes a process for preparing a compound of Formula (R)-I or (S)-I:

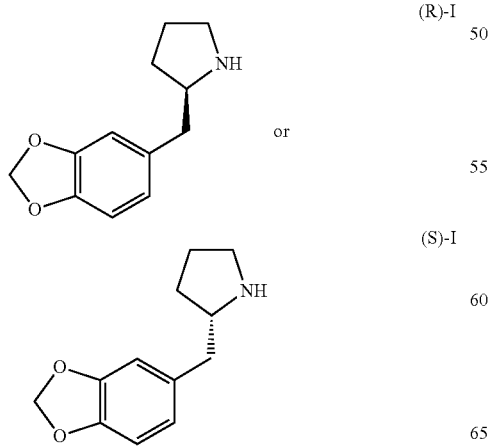

the process comprising:
reacting a compound of Formula (R)-A or (S)-A

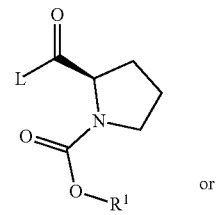

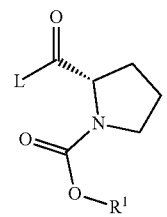

wherein L is selected from halo and $C(O)OR^2$,
$R^1$ is an unsubstituted or substituted benzyl group; and
$R^2$ is $C_{1-6}$alkyl, or
$R^2$ is

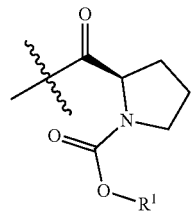

in the compound of Formula (R)-A or $R^2$ is

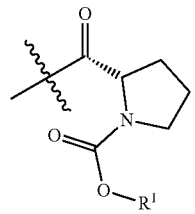

in the compound of Formula (S)-A,
with a compound of Formula B

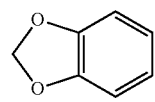

in the presence of a Lewis acid to provide a compound of Formula (R)-C and (S)-C, respectively; and

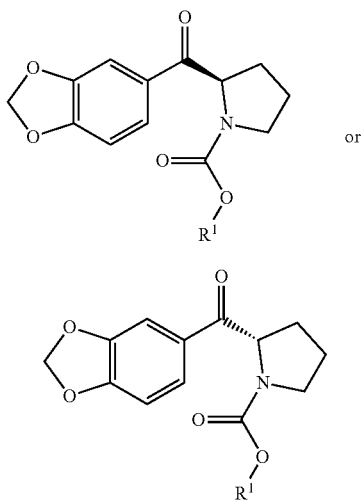

wherein R¹ is an unsubstituted or substituted benzyl group converting the compound of Formula (R)-C and (S)-C to the compound of Formula (R)-I or (S)-I, respectively.

In some embodiments, L is halo. In some embodiment, L is selected from Cl, Br and I. In some embodiments, L is Cl. Therefore, in some embodiments, the compounds of Formula (R)-B or (S)-B are acyl chlorides.

In some embodiments, L is C(O)OR². In some embodiments, R² is $C_{1-4}$alkyl. In some embodiments, R² is $CH_3$. In some embodiments, R² is

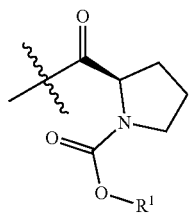

in the compound of Formula (R)-A or R² is

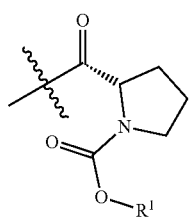

in the compound of Formula (S)-A. Therefore, in some embodiments, the compounds of Formula (R)-A or (S)-A are anhydrides.

In some embodiments, R¹ is unsubstituted benzyl group and the compounds of Formula (R)-A or (S)-A are benzyloxycarbonyl protected compounds.

In some embodiments, R¹ is substituted benzyl group. In some embodiments, substituted benzyl group is substituted with one or more substituents selected from $NO_2$, halo, $C_{1-4}$alkyl and $C_{1-4}$alkoxy. In some embodiments, R¹ is a benzyl group substituted with one or more substituents selected from $NO_2$, Br, Cl, $C_{1-4}$alkyl and $C_{1-4}$alkoxy . . . In some embodiments, R¹ is benzyl substituted with $NO_2$. In some embodiments, R¹ is p-nitrobenzyl or o-nitrobenzyl. In some embodiments, R¹ is p-nitrobenzyl. In some embodiments, R¹ is benzyl substituted with one or more of Cl or Br. In some embodiments, R¹ is 2-chlorobenzyl, 4-chlorobenzyl, 2,4-dichlorobenzyl, 2-bromobenzyl or 4-bromobenzyl. In some embodiments, R¹ is a benzyl group substituted with one or more $C_{1-4}$alkoxy. In some embodiments, R¹ is a benzyl group substituted with one or more $OCH_3$. In some embodiments, R¹ is 3,4-dimethoxybenzyl or p-methoxybenzyl. In some embodiments, R¹ is a benzyl group substituted with one or more $CH_3$ and $C(CH_3)_3$. In some embodiments, R¹ is 3,5-di-t-butylbenzyl.

In some embodiments, the Lewis acid is any Lewis acid suitable for use in a Friedel-Crafts acylation reaction. In some embodiments, the Lewis acid is selected from $BF_3$, $AlCl_3$, $SbCl_5$, $SbF_5$, $InCl_3$, $GaCl_3$, $BCl_3$, $FeCl_3$, $SnCl_4$, $TiCl_4$, $Mo_2Cl_{10}$ and $AlBr_3$, and combinations thereof. In some embodiments, the Lewis acid is selected from $BF_3$, $AlCl_3$, $SbCl_5$, $FeCl_3$, $SnCl_4$, $TiCl_4$, and $AlBr_3$ and combinations thereof. In some embodiments, the Lewis Acid is $AlCl_3$.

In some embodiments, the step of reacting compound of Formula (R)-A or (S)-A with a compound of Formula B in the presence of a Lewis acid to provide a compound of Formula (R)-C and (S)-C, respectively is performed in a suitable solvent. In some embodiments, the suitable solvent is selected from methylene dichloride, carbon disulfide, 1,2-dichloroethane, tetrachloroethane, 1,1,2,2-tetrachloroethane, and mixtures thereof. In some embodiments, the suitable solve is methylene dichloride.

In some embodiments, the compound of Formula (R)-A or (S)-A is reacted with a compound of Formula B in the presence of an excess amount (for example, about 1.2 to about 4, about 1.5 to about 2.5, about 1.2 to about 2, about 1.2 to about 1.5 molar equivalent) of the Lewis acid to provide a compound of Formula (R)-C and (S)-C, respectively.

As representative, non-limiting examples, the temperature for reacting a compound of Formula (R)-A or (S)-A with a compound of Formula B in the presence of a Lewis acid to provide a compound of Formula (R)-C and (S)-C, respectively is about −18° C. to about 25° C., about −10° C. to about 25° C., about −5° C. to about 10° C., about 0° C. to about 10° C., about 0° C. to about 20° C. about 0° C. to about 5° C. or about −10° C. to about −5° C. In some embodiments, the temperature is the temperature of ice and NaCl mixture. In some embodiments, the temperature is the temperature of a cold water bath. In some embodiments, the compound of Formula (R)-A or (S)-A is combined with a compound of Formula B in the presence of a Lewis acid at about −5° C. to about 10° C. or about 0° C. to about 10° C. and then allowed to warm to room temperature or about 18° C. to about 25° C.

In some embodiments, the compound of Formula (R)-C or (S)-C is prepared using any suitable conditions for acylating a compound of Formula (R)-A or (S)-A with a compound of Formula B in the presence of a Lewis Acid to provide a compound of Formula (R)-C and (S)-C, respectively, known in the art, for example, using the synthetic procedures found in Ookawa and Soai J. Chem. Soc., Perkin Trans. 1, 1987, 1465-1471.

In some embodiments, the compound of Formula (R)-A or (S)-A is either commercially available or can be prepared using methods known in the art or readily prepared from available precursors using methods known in the art.

For example, in some embodiments, the compound of Formula (R)-A or (S)-A when L is Cl is prepared by reacting a benzyloxycarbonyl protected D-proline or L-proline respectively in the presence of a suitable chlorinating agent in a suitable solvent. In some embodiments, the compound of Formula (R)-A or (S)-A when L is Cl is prepared by reacting a benzyloxycarbonyl protected D-proline or L-proline respectively in the presence of an excess amount (for example, about 1.2 to about 2, about 1.2 to about 1.5 or about 1.5 molar equivalent) suitable chlorinating agent in a suitable solvent. In some embodiments, the suitable chlorinating reagent is selected from thionyl chloride ($SOCl_2$), phosphorus trichloride ($PCl_3$), phosphorus pentachloride (PCls) or oxalyl chloride [$(COCl)_2$]. In some embodiments, the suitable chlorinating reagent is oxalyl chloride. In some embodiments, the suitable solvent is an inert solvent such as methylene dichloride, carbon disulfide, 1,2-dichloroethane, tetrachloroethane, 1,1,2,2-tetrachloroethane, and mixtures thereof. In some embodiments, the suitable solvent is methylene dichloride.

In some embodiments, the benzyloxycarbonyl protected D-proline or L-proline is commercially available or can be prepared using methods known in the art. For example, in some embodiments, benzyloxycarbonyl protected D-proline (i.e., N-Cbz-D-proline) and benzyloxycarbonyl protected L-proline (i.e., N-Cbz-L-proline) are available from Millipore-Sigma (Burlington, Massachusetts).

In some embodiments, the compound of Formula (R)-A or (S)-A when L is Cl is prepared in situ. Therefore, in some embodiments, the process comprises reacting benzyloxycarbonyl protected D-proline or benzyloxycarbonyl protected L-proline in the presence of a suitable chlorinating agent in a suitable solvent to provide a compound of Formula (R)-A or (S)-A wherein L is Cl respectively, and without isolation, further reacting the compound of Formula (R)-A or (S)-A wherein L is Cl with a compound of Formula B in the presence of a Lewis acid to provide a compound of Formula (R)-C or (S)-C wherein L is Cl respectively.

In some embodiments, the suitable solvent for reacting benzyloxycarbonyl protected D-proline or benzyloxycarbonyl protected L-proline in the presence of a suitable chlorinating agent to provide a compound of Formula (R)-A or (S)-A wherein L is Cl respectively, and without isolation, further reacting the compound of Formula (R)-A or (S)-A wherein L is Cl with a compound of Formula B in the presence of a Lewis acid to provide a compound of Formula (R)-C or (S)-C wherein L is Cl respectively is methylene dichloride.

In some embodiments, the compound of Formula B, 1,3-benzodioxole, is either commercially available or may be prepared using methods known in the art. For example, in some embodiments, the compound of Formula B, 1,3-benzodioxole, is available from Millipore-Sigma (Burlington, Massachusetts).

In some embodiments, the compounds of Formula (R)-C and (S)-C are converted to the compounds of Formula (R)-I or (S)-I, respectively using a one step or a two step method.

In some embodiments, the compound of Formula (R)-C and (S)-C are converted to the compound of Formula (R)-I or (S)-I, respectively using a one step one step method. In some embodiments, the compound of Formula (R)-C and (S)-C are converted to the compound of Formula (R)-I or (S)-I, respectively using a one step method in the presence of $H_2$ and a catalyst. Therefore, in some embodiments, the process comprises converting the compound of Formula (R)-C and (S)-C to the compound of Formula (R)-I or (S)-I, respectively in the presence of $H_2$ and a catalyst.

In some embodiments, the catalyst is a nickel, palladium or platinum catalyst. In some embodiment, the catalyst is a palladium catalyst. In some embodiments, the palladium catalyst is palladium on carbon (Pd/C), palladium hydroxide on carbon ($Pd(OH)_2$/C), or palladium acetate ($Pd(OAc)_2$ on carbon. In some embodiments, the palladium catalyst is palladium on carbon (Pd/C). In some embodiments, the palladium on carbon (Pd/C) is about 5% to about 10% palladium on carbon (Pd/C). In some embodiments, the palladium on carbon (Pd/C) is about 10% palladium on carbon (Pd/C).

A person skilled in the art would appreciate that in the step of converting the compound of Formula (R)-C and (S)-C to the compound of Formula (R)-I or (S)-I, respectively in the presence of $H_2$ and a catalyst, a hydrogenolysis reaction to remove the benzyloxycarbony protecting group from the compound of Formula (R)-C and (S)-C and a hydrogenation reaction to reduce the aryl carbonyl group in the compound of Formula (R)-C and (S)-C occur at the same time.

In some embodiments, the step of converting the compound of Formula (R)-C and (S)-C to provide the compound of Formula (R)-I or (S)-I, respectively can occur in two steps.

In some embodiments, the compound of Formula (R)-C and (S)-C is converted to the compound of Formula (R)-I or (S)-I, respectively using a two step method. Therefore, in some embodiments, the process comprises converting the compound of Formula (R)-C and (S)-C to the compound of Formula (R)-I or (S)-I, respectively, the converting comprising reducing the compound of compound of Formula (R)-C and (S)-C with a suitable
reducing agent to provide a compound of (R)-D and (S)-D, respectively, and

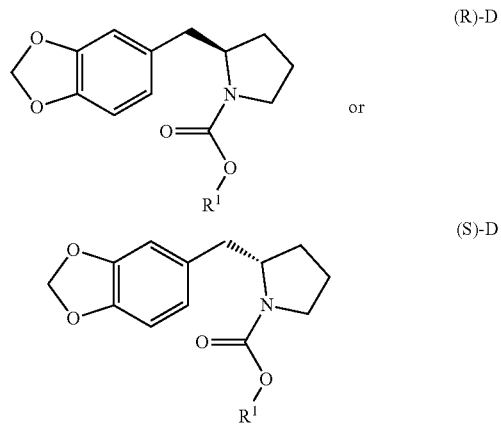

wherein $R^1$ is an unsubstituted or substituted benzyl group
deprotecting the compound of (R)-D and (S)-D to provide the compound of Formula (R)-I or (S)-I, respectively.

In some embodiments, the reducing agent to provide the compound of a compound of (R)-D and (S)-D, respectively from the compound of (R)-C and (S)-C, is any suitable reducing agent that reduces the aryl ketone of the compound of (R)-C and (S)-C to an alkylene. In some embodiments, the compound of compound of Formula (R)-C and (S)-C is reduced with a suitable reducing agent to provide a compound of (R)-D and (S)-D under Clemmensen reduction conditions. In some embodiments, the suitable reducing agent for reacting with the compound of (R)-C and (S)-C is zinc amalgam (Zn—Hg) in the presence of an acid. In some embodiments, the acid is concentrated hydrochloric acid.

In some embodiments, deprotecting the compound of (R)-D and (S)-D to provide the compound of Formula (R)-I or (S)-I, respectively is in the presence of $H_2$ and a catalyst. In some embodiment, the catalyst is a nickel, palladium or platinum catalyst. In some embodiment, the catalyst is a palladium catalyst. In some embodiments, the palladium catalyst is palladium on carbon (Pd/C), palladium hydroxide on carbon (Pd(OH)$_2$/C), or palladium acetate (Pd(OAc)$_2$ on carbon. In some embodiments, the palladium catalyst is palladium on carbon (Pd/C). In some embodiments, the palladium on carbon (Pd/C) is about 5% to about 10% palladium on carbon (Pd/C). In some embodiments, the palladium on carbon (Pd/C) is about 10% palladium on carbon (Pd/C).

In some embodiments, the step of deprotecting the compound of (R)-D and (S)-D to provide the compound of Formula (R)-I or (S)-I, respectively is in the presence of a Lewis acid and an acid. In some embodiments, the acid is hydrobromic acid.

In some embodiments, the process provides the compound of Formula (R)-I or (S)-I, respectively as the major isomer. In some embodiments, the process provides the compound of Formula (R)-I in greater than 60% ee, 65% ee, 70% ee, 75% ee. 80% ee, 85% ee, 90% ee, 95% ee, 98% ee or 99% ee. In some embodiments, the process provides the compound of Formula (S)-I in greater than 60% ee, 65% ee, 70% ee, 75% ee, 80% ee, 85% ee, 90% ee, 95% ee, 98% ee or 99% ee.

In some embodiments, the enantiomeric excess of an enantiomer is determined using a variety of analytical techniques known in the art, including NMR spectroscopy, chiral column chromatography, or optical polarimetry. In some embodiments, the enantiomeric excess of an enantiomer is determined using a polarimeter using methods known in the art.

In some embodiments, the process provides the compound of Formula (R)-I. Therefore, the present application includes a process for preparing a compound of Formula (R)-I:

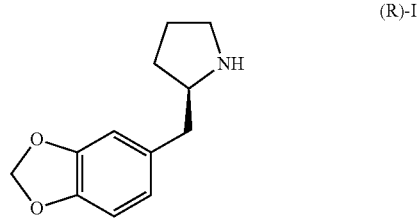 [SMILES: c1cc2c(cc1C[C@H]1CCCN1)OCO2]

the process comprising:
reacting a compound of Formula (R)-A

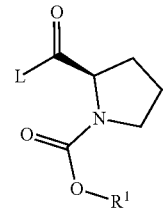

wherein L is selected from halo and C(O)OR$^2$,
R$^1$ is an unsubstituted or substituted benzyl group; and
R$^2$ is C$_{1-6}$alkyl or

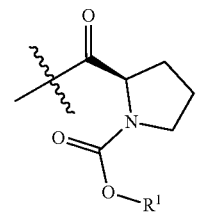

with a compound of Formula B

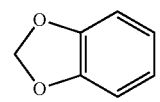

in the presence of a Lewis acid to provide a compound of Formula (R)-C; and

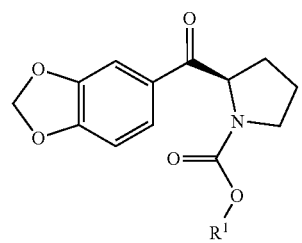

wherein R$^1$ is an unsubstituted or substituted benzyl group
converting the compound of Formula (R)-C to the compound of Formula (R)-I.

In some embodiments, the process provides the compound of Formula (S)-I. Therefore, the present application includes a process for preparing a compound of Formula (S)-I:

In an exemplary embodiment of a process of the application, the present application includes a process for preparing a compound of Formula (R)-I or (S)-I:

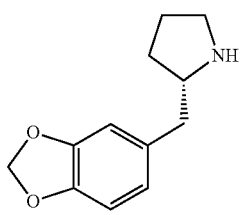
(R)-I the process comprising:
reacting a compound of Formula (S)-A

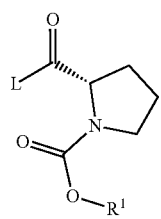
(S)-A wherein L is selected from halo and C(O)OR², 
R¹ is an unsubstituted or substituted benzyl group; and
R² is $C_{1-6}$alkyl or

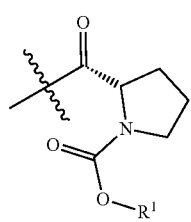

with a compound of Formula B

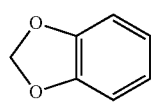

in the presence of a Lewis acid to provide a compound of Formula (S)-C; and

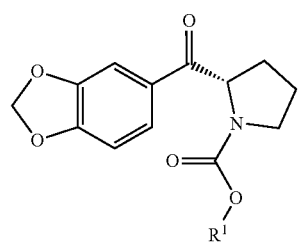
(S)-C wherein R¹ is an unsubstituted or substituted benzyl group
converting the compound of Formula (S)-C to the compound of Formula (S)-I.

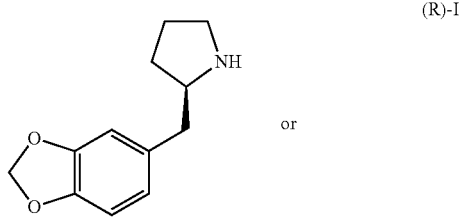
(R)-I or (S)-I the process comprising:
reacting a compound of Formula (R)-A or (S)-A (R)-A or (S)-A wherein L is halo; and
R¹ is an unsubstituted or substituted benzyl group;
with a compound of Formula B

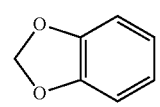

in the presence of a Lewis acid to provide a compound of Formula (R)-C and (S)-C, respectively; and

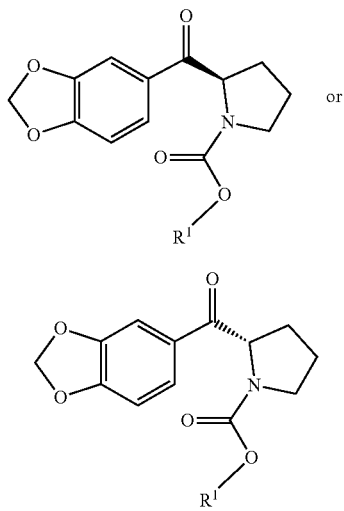

(R)-C or (S)-C wherein R¹ is an unsubstituted or substituted benzyl group converting the compound of Formula (R)-C and (S)-C to the compound of Formula (R)-I or (S)-I, respectively in the presence of $H_2$ and a catalyst.

In an exemplary embodiment of a process of the application, the present application includes a process for preparing a compound of Formula (R)-I:

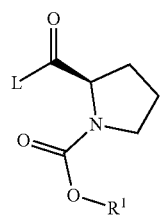

(R)-I the process comprising:

reacting a compound of Formula (R)-A

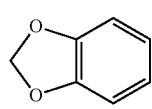

(R)-A wherein L is halo; and

R¹ is a an unsubstituted or substituted benzyl group;

with a compound of Formula B

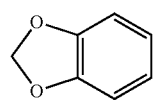

in the presence of a Lewis acid to provide a compound of Formula (R)-C; and

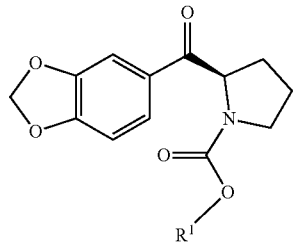

(R)-C wherein R¹ is an unsubstituted or substituted benzyl group converting the compound of Formula (R)-C to the compound of Formula (R)-I in the presence of $H_2$ and a catalyst.

In an exemplary embodiment of a process of the application, the present application includes a process for preparing a compound of Formula (S)-I:

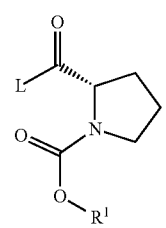

(S)-I the process comprising:

reacting a compound of Formula (S)-A

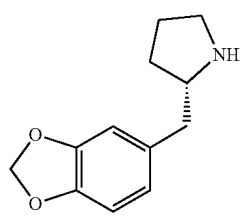

(S)-A wherein L is halo; and

R¹ is an unsubstituted or substituted benzyl group;

with a compound of Formula B

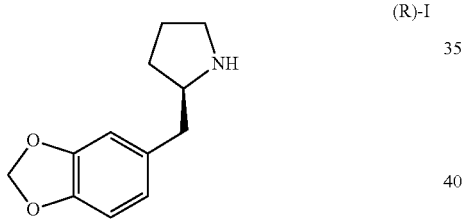

in the presence of a Lewis acid to provide a compound of Formula (S)-C, respectively; and

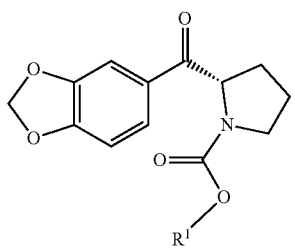

(S)-C wherein $R^1$ is an unsubstituted or substituted benzyl group converting the compound of Formula (S)-C to the compound of Formula (S)-I in the presence of $H_2$ and a catalyst.

In an exemplary embodiment, $R^1$ is an unsubstituted benzyl group.

In some embodiments, the compound of Formula (R)-I or (S)-I: prepared by a process of the application is further converted to a salt, solvate and/or prodrug thereof, for example, a pharmaceutically acceptable salt, solvate and/or prodrug thereof. In some embodiments, the compound of Formula (R)-I prepared by a process of the application is further converted to a salt, solvate and/or prodrug thereof, for example, a pharmaceutically acceptable salt, solvate and/or prodrug thereof. In some embodiments, the compound of Formula (S)-I prepared by a process of the application is further converted to a salt, solvate and/or prodrug thereof, for example, a pharmaceutically acceptable salt, solvate and/or prodrug thereof.

In some embodiments the pharmaceutically acceptable salt is an acid addition salt and the selection of a suitable salt may be made by a person skilled in the art (see, for example, S. M. Berge, et al., "Pharmaceutical Salts," J. Pharm. Sci. 1977, 66, 1-19).

An acid addition salt that is pharmaceutically acceptable, that is suitable for, or compatible with, the treatment of subjects, is any non-toxic organic or inorganic acid addition salt of any basic compound. Basic compounds that form an acid addition salt include, for example, compounds comprising an amine group. Illustrative inorganic acids which form suitable salts include hydrochloric, hydrobromic, sulfuric, nitric and phosphoric acids, as well as acidic metal salts such as sodium monohydrogen orthophosphate and potassium hydrogen sulfate. Illustrative organic acids which form suitable salts include mono-, di- and tricarboxylic acids. Illustrative of such organic acids are, for example, acetic, trifluoroacetic, propionic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, mandelic, salicylic, 2-phenoxybenzoic, p-toluenesulfonic acid and other sulfonic acids such as methanesulfonic acid, ethanesulfonic acid and 2-hydroxyethanesulfonic acid. In an embodiment, the mono- or di-acid salts are formed, and such salts exist in either a hydrated, solvated or substantially anhydrous form. In general, acid addition salts are more soluble in water and various hydrophilic organic solvents, and generally demonstrate higher melting points in comparison to their free base forms. The selection criteria for the appropriate salt will be known to one skilled in the art. Other non-pharmaceutically acceptable salts such as but not limited to oxalates may be used, for example in the isolation of compounds of the application for laboratory use, or for subsequent conversion to a pharmaceutically acceptable acid addition salt.

In some embodiments, the compound of Formula (R)-I or (S)-I is reacted with hydrochloric acid to provide the hydrochloride salt of the compound of Formula (R)-I or (S)-I. In some embodiments, the compound of Formula (R)-I is reacted with hydrochloric acid to provide the hydrochloride salt of the compound of Formula (R)-I. In some embodiments, the compound of Formula (S)-I is reacted with hydrochloric acid to provide the hydrochloride salt of the compound of Formula (S)-I. Solvates of the compounds of Formula (R)-I or (S)-I include, for example, those made with solvents that are pharmaceutically acceptable. Examples of such solvents include water (resulting solvate is called a hydrate) and ethanol and the like. Suitable solvents are physiologically tolerable at the dosage administered.

The formation of a desired compound salt is achieved using standard techniques. For example, the neutral compound is treated with an acid in a suitable solvent and the formed salt is isolated by filtration, extraction or any other suitable method.

The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

Prodrugs of the compounds of Formula (R)-I or (S)-I may be, for example, conventional esters formed with the available amino group. Some common esters which have been utilized as prodrugs are phenyl esters, aliphatic ($C_1$-$C_{24}$) esters, acyloxymethyl esters, carbamates and amino acid esters.

Examples of inert solvents include, but are not limited to, benzene, toluene, tetrahydrofuran, ethyl ether, ethyl acetate, dimethyl formamide (DMF), acetonitrile, $C_{1-6}$alkylOH (e.g. methanol, ethanol, n-propanol, 2-propanol, n-butanol, butan-2-ol and 2-methyl-1-propanol), diethylcarbonate, hexane and dimethylsulfoxide (DMSO). Further examples can include aqueous solutions, such as water and dilute acids and bases, and ionic liquids, provided that such solvents do not interfere with the reaction.

VI. Methods and Preparation of the Application

The compound of Formula (R)-I can also be prepared by various synthetic processes known in the art. The selection of a particular process is within the purview of the person of skill in the art. Some starting materials are available from commercial chemical sources. Other starting materials are readily prepared from available precursors using straightforward transformations that are well known in the art.

The compound of Formula (R)-I generally can be prepared according to the processes illustrated in the Schemes below. A person skilled in the art would appreciate that many of the reactions depicted in the Schemes below would be sensitive to oxygen and water and would know to perform the reaction under an anhydrous, inert atmosphere if needed. Reaction temperatures and times are presented for illustrative purposes only and may be varied to optimize yield as would be understood by a person skilled in the art.

Accordingly, in some embodiments, the compound of Formula (R)-I, is prepared as shown in Scheme 1. Therefore, in some embodiments, (R)-prolinol ((R)-2-(hydroxymethyl) pyrrolidine) is reacted with sulfuryl chloride in a suitable solvent such as pyridine and dichloromethane or a mixture thereof at a suitable temperature such as about 60° C. to about 80° C. to provide the sulfamate intermediate of Formula A. The sulfamate intermediate of Formula A is subsequently reacted with the compound of Formula B wherein X is a leaving group in the presence of an organolithium reagent such as n-butyl lithium followed by acidic hydrolysis of the resultant sulfamic acid in the presence of a suitable acid such as HCl and a suitable solvent such as ethanol at a suitable temperature such as about 70° C. to about 95° C. to provide the compound of Formula (R)-I.

the presence of a coupling agent such as phosphorus oxychloride affords the 2-acylpyrrole compound of Formula D. Removal of the ketonic oxygen from the compound of Formula D in the presence of a suitable reducing agent such as sodium borohydride provides the compound of Formula E. Hydrogenation of the pyrrole ring in the compound of Formula E provide the racemic compound of Formula (R/S)-I. The racemic compound of Formula (R/S)-I can be resolved into the separate R and S enantiomers of Formula (R)-I and (S)-I by methods known in the art.

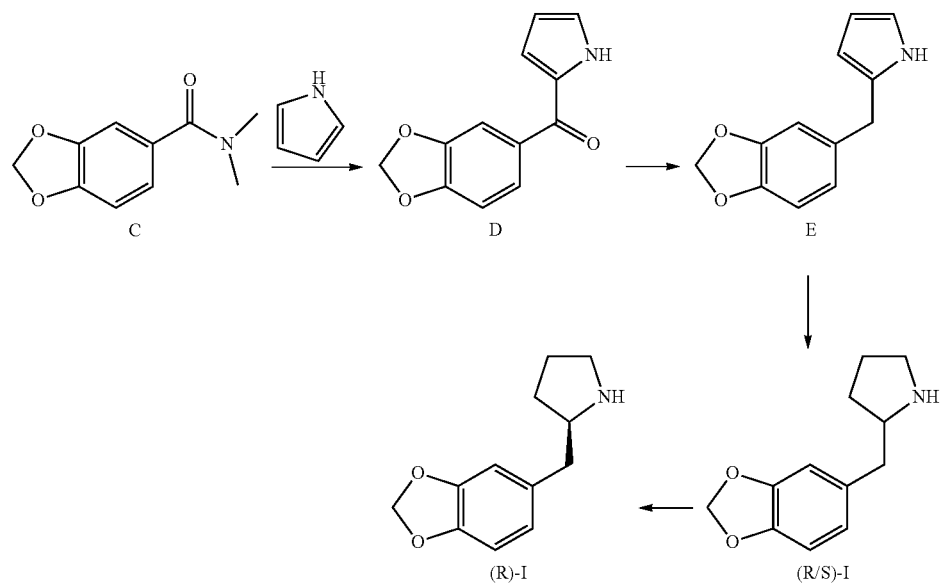

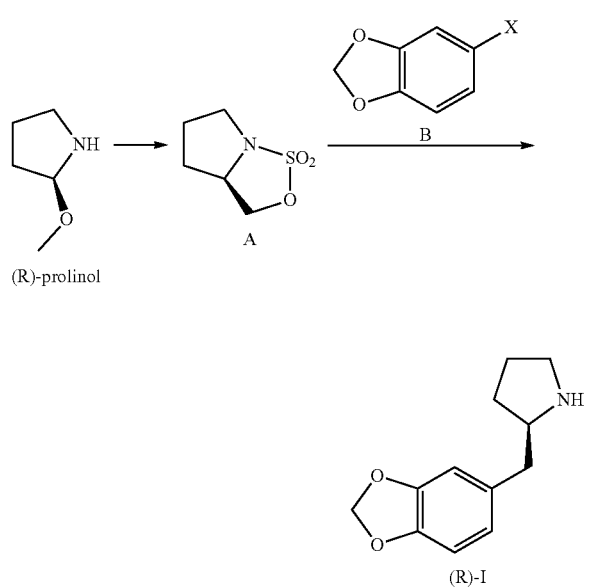

In some embodiments, the compounds of Formula (R)-I are prepared as shown in Scheme 2. Therefore, in some embodiments, the condensation between the N,N-dimethylpiperonylamide compound of Formula C and pyrrole in It would be appreciated by the person skilled in the art that the compound of Formula (S)-I and Formula (R/S)-I can be prepared according to the processes illustrated in the Schemes above using starting materials having the corresponding (S) enantiomeric configuration or starting materials which are racemic, respectively. The compounds of Formula (R)-I, Formula (S)-I and Formula (R/S)-I can also be prepared by methods known in the art, for example, by the methods disclosed in Williams et al., Med. Chem. Commun., 2015, 6, 1054 and Dolby L. J. et al, J. Org. Chem., 37 (23), 1972 p 3691.

Comparative racemic MDMA compounds can be prepared by various synthetic processes. The selection of a particular process is within the purview of the person of skill in the art. For example, by the methods disclosed in Dunlap et al (2018), ACS Chem Neurosci; 9(10): 2408-2427; Llabrés et al (2014), European J. of Med. Chem. 81 (2014) 35-46; Huot et al (2011), J Neurosci. (2011) May 11; 31(19): 7190-7198 and Felim et al., Chem Res Toxicol. 2010 23(1):211-9.

Nucleophilic displacement reaction conditions comprise any known method for the reaction of a nucleophile to displace a leaving group to form a bond that is compatible with the intermediates and products shown in the above Schemes or that may be used to prepare a compound of the application. In some embodiments, such conditions comprise combining reactants in the presence of a base in a suitable solvent.

Throughout the processes described herein it is to be understood that, where appropriate, suitable protecting groups will be added to, and subsequently removed from, the various reactants and intermediates in a manner that will be readily understood by one skilled in the art. Conventional procedures for using such protecting groups as well as examples of suitable protecting groups are described, for example, in "*Protective Groups in Organic Synthesis*", T. W. Green, P. G. M. Wuts, Wiley-Interscience, New York, (1999).

It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to one skilled in the art. Examples of transformations are given herein, and it is to be understood that the described transformations are not limited only to the generic groups or substituents for which the transformations are exemplified. References and descriptions of other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "*Advanced Organic Chemistry*", March, 4th ed. McGraw Hill (1992) or, "*Organic Synthesis*", Smith, McGraw Hill, (1994).

Techniques for purification of intermediates and final products include, for example, straight and reversed phase chromatography on column or rotating plate, recrystallisation, distillation and liquid-liquid or solid-liquid extraction, which will be readily understood by one skilled in the art.

The products of the processes of the application may be isolated according to known methods, for example, the compounds may be isolated by evaporation of the solvent, by filtration, centrifugation, chromatography or other suitable method.

Generally, the reactions described above can be performed in a suitable inert organic solvent and at temperatures and for times that will optimize the yield of the desired compounds. Examples of suitable inert organic solvents include, but are not limited to, 2-propanol, dimethylformamide (DMF), 1,4-dioxane, methylene chloride, chloroform, tetrahydrofuran (THF), toluene, and the like.

The formation of a desired compound salt is achieved using standard techniques. For example, the neutral compound is treated with an acid or base in a suitable solvent and the formed salt is isolated by filtration, extraction or any other suitable method.

The formation of solvates of the compounds of the application will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

Prodrugs of the compounds of the present application may be, for example, conventional esters formed with available hydroxy, thiol, amino or carboxyl groups. For example, available hydroxy or amino groups may be acylated using an activated acid in the presence of a base, and optionally, in inert solvent (e.g. an acid chloride in pyridine).

One skilled in the art will recognize that where a reaction step of the present application is carried out in a variety of solvents or solvent systems, said reaction step may also be carried out in a mixture of the suitable solvents or solvent systems.

EXAMPLES

The following non-limiting examples are illustrative of the present application:

Example 1: Exemplary preparation of (R)-2-[(2H-1, 3-benzodioxol-5-yl)methyl]pyrrolidine—A (R)-2-[(2H-1,3-benzodioxol-5-yl)methyl]pyrrolidine may be prepared using methods disclosed in Williams et al., Med. Chem. Commun., 2015, 6, 1054 for the preparation of (S)-2-[(2H-1,3-benzodioxol-5-yl)methyl]pyrrolidine (R)-tetrahydro-3H-pyrrolo[1,2-c][1,2,3]oxathiazole 1,1-dioxide A solution of sulfuryl chloride (8 mL, 99 mmol) in DCM (40 mL) is added dropwise over 1.5 h to a well stirred −78° C. solution of (R)-2-(hydroxymethyl)pyrrolidine (10 g, 99 mmol) and pyridine (16 mL, 20 mmol) in DCM (60 mL) under argon. After 3 h the cooling bath is removed and the mixture is allowed to reach 0° C. The reaction mixture is quenched into ice water and transferred to a separating funnel. The layers are separated and the aqueous layer is extracted with DCM (2×). The combined organic extracts are washed with 1M aq. HCl soln., with water, and with brine. The organic layer is dried over $Na_2SO_4$, filtered, and evaporated in vacuo to give a yellow solid. This was then re-dissolved in THF (50 mL), filtered through a sintered funnel to remove residual pyridine·HCl and concentrated in vacuo to give the title compound as a pale yellow solid (8.8 g, 55%).

(R)-2-(benzo[d][1,3]dioxol-5-ylmethyl)pyrrolidine n-BuLi 1.6 M in hexane is added to a solution of 4-bromo-1,2-(methylenedioxy)benzene (1.8 mL, 15 mmol) in THF under Argon at such a rate that the internal temperature remains below −70° C. After a few minutes the mixture becomes cloudy and a suspension is formed. After 30 min a solution of (R)-tetrahydro-3H-pyrrolo[1,2-c][1,2,3]oxathiazole 1,1-dioxide (2.0 g, 12 mmol) in THF) is added keeping the internal temperature below −70° C. The cooling bath is removed and the mixture returned slowly to room temperature (RT) where all solids go back into solution. The solution is stirred for 1 h at RT and the volatiles are removed in vacuo. The residue is dissolved in 1:1 2 M aq. HCl and ethanol and heated to 95° C. for 40 h. The reaction mixture is cooled to RT, diluted with $H_2O$, and the mixture is washed with TBME (1×). This extract is discarded and the aqueous phase is basified with 5 M aq. NaOH and re-extracted with TBME (3×60 mL). The combined organic extracts are dried over Na2SO4, filtered, and evaporated in vacuo to give the title compound.

Example 2: Exemplary preparation of (R)-2-[(2H-1, 3-benzodioxol-5-yl)methyl]pyrrolidine—B (R)-2-[(2H-1,3-benzodioxol-5-yl)methyl]pyrrolidine may be prepared using methods disclosed in Dolby L. J. et al, J.

Org. Chem., 37 (23), 1972 p 3691 for (R/S)-2-[(2H-1,3-benzodioxol-5-yl)methyl]pyrrolidine.

N,N-Dimethylpiperonylamide

Piperonylic acid (63.8 g, 0.384 mol) is added in portions with stirring to thionyl chloride (270 ml) over 20 min. The slurry is heated under reflux for 1 hr, during which time the acid gradually dissolves. Excess thionyl chloride is removed under reduced pressure and the residue is evaporated with dry benzene. The crude acid chloride is added to 40% aqueous dimethylamine in portions with stirring and cooling over 15 min. The mixture is stirred for 2 hr at room temperature and then is made strongly alkaline with 4 N sodium hydroxide and saturated with sodium chloride. The aqueous solution is extracted with methylene chloride, and the organic phases are filtered through paper and concentrated under reduced pressure to give the crude amide (57.1 g, 77%) as a dark oil. Distillation gives the amide as a hygroscopic, viscous liquid (53 g, 71%):

2-(3,4-Methylenedioxybenzoyl)pyrrole

To a cooled solution of N,N-dimethylpiperonylamide (58.5 g, 0.303 mol) in ethylene dichloride (60 ml) is added dropwise over 15 min freshly distilled phosphorus oxychloride (46.5 g, 0.303 mol) with stirring. The mixture is stirred in the cold for 10 min and then at room temperature for 1.5 hr. Additional ethylene dichloride is added (60 ml) followed by addition of a solution of freshly distilled pyrrole (20.3 g, 0.303 mol) in ethylene dichloride (60 ml) over 10 min. The mixture is stirred at room temperature for 10 min and then is brought to reflux for 1 hr. The dark red mixture is cooled and sodium acetate trihydrate (300 g) in water (600 ml) is added, slowly at first, then as rapidly as possible with vigorous stirring. The mixture is brought to reflux for about 15 min, after which the phases are separated while still warm. The aqueous phase is extracted with chloroform and the combined organic solutions are washed with brine, dried, and concentrated under reduced pressure. The dark solid residue is washed with a small amount of cold methanol, then ether, and is dried to give the acylpyrrole (51.7 g, 80%) as a yellow solid. 2-(3,4-Methylenedioxybenzyl)pyrrole A mixture of 2-(3,4-methylenedioxybenzoyl)pyrrole (37.8 g, 0.175 mol), sodium borohydride (19 g, 0.50 mol), and dioxane (500 ml) is refluxed under nitrogen for 4 hr. The solution is concentrated under reduced pressure, diluted with water (500 ml), and is extracted with ether-methylene chloride (2:1, 300 ml). The organic solution is washed with water, dried, and is concentrated under reduced pressure to leave a dark viscous oil. Distillation under reduced pressure gives the benzylpyrrole as a colorless liquid (20.8 g, 59%), bp 125-130° (0.03 mm).

2-(3,4-Methylenedioxybenzyl)pyrrolidine

A solution of 2-(3,4-methylenedioxybenzyl)pyrrole (28.9 g, 0.144 mol) in glacial acetic acid (100 ml) is hydrogenated at an initial pressure of 50 psi in a Parr apparatus over 5% rhodium on alumina (3 g) for 8 hr. The catalyst is filtered and the filtrate is diluted to 500 ml with water. The aqueous solution is extracted with ether and then made strongly alkaline with 50% sodium hydroxide and is extracted with methylene chloride. The organic solution is dried and concentrated under reduced pressure and the dark oil is distilled under reduced pressure to give the benzylpyrrolidine. A hydrochloride salt is prepared by the addition of saturated ethanolic hydrogen chloride to an ether solution of the pyrrolidine.

(R)-2-(3,4-Methylenedioxybenzyl)pyrrolidine (R)-2-(3,4-Methylenedioxybenzyl)pyrrolidine (Compound of Formula (R)-1) is resolved using enantiomer separation methods known in the art, for example, using chromatographic method such as chiral chromatographic, crystallization, synthetic methods such as by the introduction of a suitable asymmetric group on N-atom to form diastereomers which can be resolved using chromatographic methods, or other such methods to obtain a compound of Formula (R)-1 from the racemic mixture, for example, the methods as disclosed in Jacques, J., et al., Enantiomers, Racemates and Resolutions (Wiley-Interscience, New York, 1981); Wilen, S. H., et al, Tetrahedron 33:2725 (1977); Eliel, E. L., Stereochemistry of Carbon Compounds (McGraw-Hill, N Y, 1962); Wilen, S. H., Tables of Resolving Agents and Optical Resolutions p. 268 (E. L. Eliel, Ed., Univ. of Notre Dame Press, Notre Dame, IN, 1972 and Thompson, Wayne J. et al: Journal of Medicinal Chemistry, 33(2), 789-808; 1990.

Example 3: Exemplary Preparation of (R)-2-[(2H-1,3-benzodioxol-5-yl)methyl]pyrrolidine Using the Process of the Application*

(R)-benzyl 2-(chlorocarbonyl)pyrrolidine-1-carboxylate (Cbz-(D)-Pro-OH) a (2.0 g, 8.0 mmol) is dissolved in DCM (10 mL) and oxalyl chloride (6 mL of a 2M solution, 12.0 mmol) is added, followed by addition of DMF (2 drops). The mixture is stirred at room temperature for 30 min. The solution is concentrated to afford (R)-benzyl 2-(chlorocarbonyl)pyrrolidine-1-carboxylate. The acid chloride is mixed with aluminum chloride (1.03 g, 8.4 mmol) in DCM (10 mL) and stirred until aluminum chloride all dissolved under cooling water bath. Then 2H-1,3-benzodioxole (1.074 g, 8.8 mmol) is added dropwise and stirred at room temperature. The reaction mixture is poured into water and ice. The organic layer is extracted with DCM, dried over sodium sulphate. The solvent is evaporated under reduced pressure, to produce *CBz protected (R)-benzo[d][1,3]dioxol-5-yl(pyrrolidin-2-yl)methanone.

A suspension of about 100 g of CBz protected (R)-benzo[d][1,3]dioxol-5-yl(pyrrolidin-2-yl)methanone in about 1000 ml methanol, and 10% Pd/C (about 1.0-5 g) is subjected to hydrogenation at about 45-50 psi. Upon completion of the reaction the catalyst is filtered and the solvent is distilled off the solvent under vacuum to provide the title compound. *(S)-2-[(2H-1,3-benzodioxol-5-yl)methyl]pyrrolidine is prepared in a same manner as (R)-2-[(2H-1,3-benzodioxol-5-yl)methyl]pyrrolidine. CBz protected (S)-benzo[d][1,3]dioxol-5-yl(pyrrolidin-2-yl)methanone is prepared in a same manner from (S)-benzyl 2-(chlorocarbonyl)pyrrolidine-1-carboxylate starting from (Cbz-(L)-Pro-OH).

Example 4: Exemplary Preparation of (R)-2-[(2H-1,3-benzodioxol-5-yl)methyl]pyrrolidine and (S)-2-[(2H-1,3-benzodioxol-5-yl)methyl]pyrrolidine

Step 1: Manufacturing of (S)-tetrahydro-3H-pyrrolo[1,2-c][1,2,3]oxathiazole 1,1-dioxide

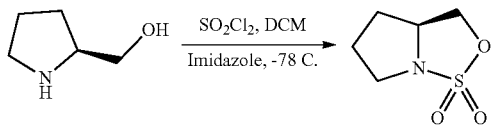 [SMILES: OC[C@@H]1CCCN1 ; O=S1(=O)OC[C@@H]2CCCN21]

A solution of sulfuryl chloride (8 mL, 99 mmol) in dichloromethane (DCM) (40 mL) was added dropwise over 1 h to a well-stirred −78° C. solution of (S)-(+)-prolinol (5 g, 49.43 mmol) and imidazole (6.73 g, 98.86 mmol) in DCM (75 mL) under argon.

After 4 h, the cooling bath was removed and allowed to warm to room temperature overnight.

The reaction mixture was filtered through a short plug of silica to remove the precipitated imidazolium salt and washed with water (1×).

The aqueous layer was back extracted with DCM (×3), and the organic layers were combined. The combined organic layer was washed with brine, dried with sodium sulfate, and concentrated in vacuo to give a light-yellow oil.

The product was crystallized in ethanol/diethyl ether to afford a white solid. (4.22 g 52%). Spectral data matched that reported in the literature (Ferrari et al. (2022), Org. Process Res. Dev. 26, 9, 2614-2623).

The above procedure was modified to produce the R-enantiomer (4.46 g, 55%) by starting from (R)-(−)-prolinol.

Step 2: Manufacturing (S)-2-(benzo[d][1,3]dioxol-5-ylmethyl)pyrrolidine ((S)-I)

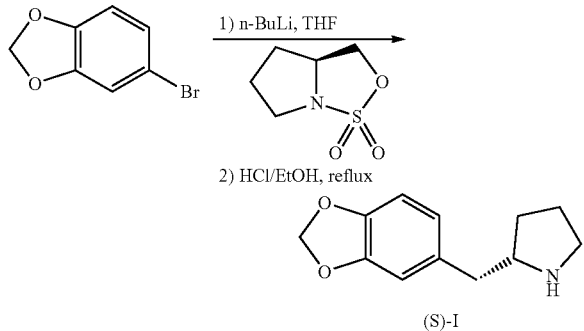

nBuLi (2.5 M in hexanes, 5.88 mL, 14.7 mmol) was added to a solution of 4-bromo-1,2-methylenedioxybenzene (2.95 g, 14.7 mmol) in THF (40 mL) under nitrogen at such a rate that the internal temperature remained below −70° C.

A cloudy white suspension formed in the solution. This suspension was allowed to stir for approximately 90 minutes at −78 C, after which the sulfamidate (in THF) (2.0 g, 12.25 mmol) was added dropwise over 1 hr at −78 C. This was slowly allowed to warm to RT overnight and then concentrated in vacuo.

The residue was dissolved in 2 M aq. HCl (25 mL) and ethanol (25 mL) and heated to reflux for 2 days. The reaction mixture was cooled to RT, concentrated in in-vacuo to remove ethanol, and diluted with $H_2O$.

The aqueous layer was extracted with diethyl ether, and the ether layer was discarded. The aqueous layer solution was basified with 5N NaOH and extracted with DCM (5×).

The organic layers were combined, washed with brine, dried with $MgSO_4$, filtered, and concentrated in vacuo to obtain a yellow oil (1.1 g).

The oil was taken up in EtOH, and 2N HCl in diethyl ether was added to generate the hydrochloride salt as an off-white solid ((S)-I. Hydrochloride) (525 mg, 27%)

The same procedure was followed to generate the hydrochloride salt of (R)-I·hydrochloride (610 mg, 31%) as an off-white solid.

$^1$H NMR* ($CD_3OD$) δ: 1.70-1.76 (m, 1H), 1.99-2.17 (m, 3H), 2.92-2.96 (m, 2H), 3.24-3.35 (m, 3H), 3.69-3.73 (pent, 1H, J=8 Hz, 15.2 Hz), 5.93 (s, 2H), 6.75-6.81 (m, 3H). $^{13}$C: 24.27, 30.98, 38.67, 46.45, 63.63, 102.61, 109.67, 110.24, 123.29, 131.74, 148.49, 149.76 [M+H]$^+$=206.1

HCl salt

Final Yields: (S)-I hydrochloride: 27%; (R)-I hydrochloride: 31%

Example 5: Exemplary Compositions of the Application

Exemplary Composition 1: enantiomerically pure compound of Formula (R)-I (>99% R enantiomer)
Exemplary Composition 2: 90-99% compound of Formula (R)-I, 1-10% compound of Formula (S)-I
Exemplary Composition 3: 80-89.9% compound of Formula (R)-I 10.1%-20% compound of Formula (S)-I
Exemplary Composition 4: 70-79.9% compound of Formula (R)-I, 20.1-30% compound of Formula (S)-I
Exemplary Composition 5: 60-69.9% compound of Formula (R)-I, 30.1-40% compound of Formula (S)-I
Exemplary Composition 6: 51-59.9% compound of Formula (R)-I, 40.1-40% compound of Formula (S)-I
Comparative Composition 1: Racemic compound of Formula (R/S)-I
Comparative Composition 2: Racemic MDMA
Comparative Composition 2: Racemic MBDB Biological Data

Example 6: Computational Studies a. Docking Studies

Docking studies were performed with the compound of Formula (R)-I and (S)-I with the 5-HT$_{2A}$ receptor and using the Glide® ligand docking program (e.g., Halgren T. A et al. J. Med. Chem. 2004, 47, 1750-1759) using 6WHA cryoEM structure of 5-HT2A, resolved at 3.4 A (FIG. 1). As shown in FIG. 1, the basic alkylamine forms a salt bridge to the highly conserved D155 side chain in TM3. There is a cluster of aromatic residues F243, W336, F339 and F340.

Figure 2:
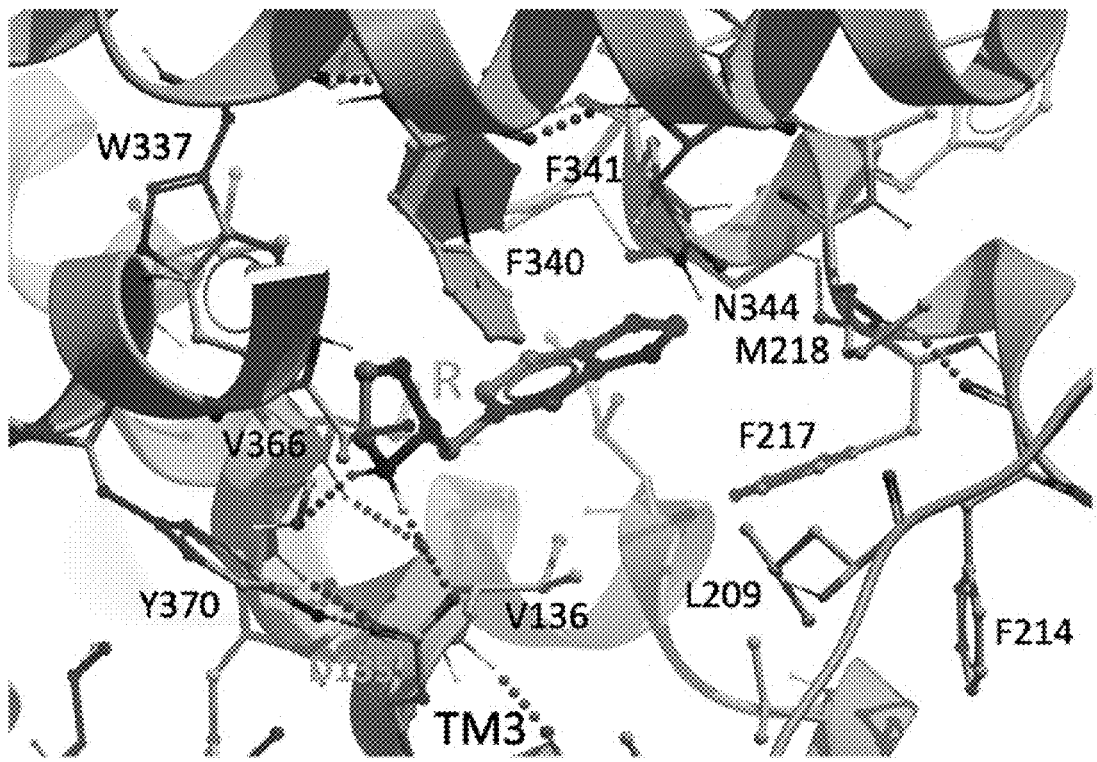
FIG. 2 are pictures showing the results of docking studies with the compound of Formula (R)-I (top panel) and the compound of Formula (S)-I (bottom panel) with the 5-HT2B receptor using Glide® using 6DRZ cryoEM structure of 5-HT2B, resolved at 3.1 A.
Figure 2:
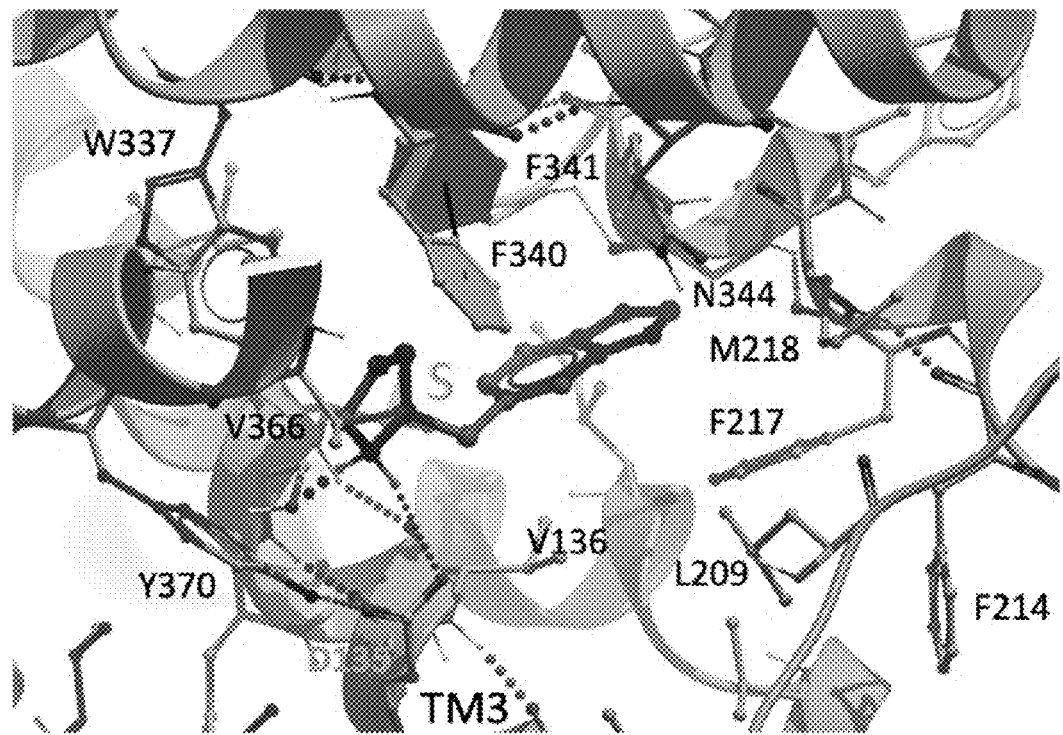

Docking studies were performed with the compound of Formula (R)-I and (S)-I with the 5-HT2B receptor and using the Glide® ligand docking program using 6DRZ cryoEM structure of 5-HT2B, resolved at 3.1 A (FIG. 2). As shown in FIG. 2, the basic alkylamine forms a salt bridge to the highly conserved D135 side chain in TM3. There is a cluster of aromatic & aliphatic residues V136, 1186, F340, F341, V366.

Similar docking studies were performed using the (R)- and (S)-enantiomers of MDMA.

Docking scores of the compound of Formula (R)-I and (S)-I and the (R)- and (S)-enantiomers of MDMA (R-MDMA and S-MDMA, respectively) when docked to the 5-HT$_{2A}$ receptor are provided in Table 1.

Docking scores of the compound of Formula (R)-I and (S)-I and the (R)- and (S)-enantiomers of MDMA when docked to the 5-HT$_{2B}$ receptor are provided in Table 2.

TABLE 1

| | 5HT$_{2A}$ | | | |
| --- | --- | --- | --- | --- |
| Parameters | Compound of Formula (R)-1- | Compound of Formula (S)-1- | R-MDMA | S-MDMA |
| XP GScore (kcal/mol) | −7.35 | −7.00 | −7.17 | −6.97 |
| Glide Energy | −35.40 | −34.56 | −32.47 | −37.91 |
| *Glide evdw | −22.50 | −23.11 | −20.48 | −22.10 |
| **Glide ecoul | −12.91 | −11.45 | −12.00 | −15.81 |

*Glide evdw stands for van der Waals energy.
**Glide ecoul stands for Coulomb energy.

All items are involved in the Glide gscore algorithm

TABLE 2

| | 5HT2B | | | |
| --- | --- | --- | --- | --- |
| Parameters | Compound of Formula (R)-1 | Compound of Formula (S)-1 | R-MDMA | S-MDMA |
| XP GScore (kcal/mol) | −7.53 | −8.18 | −7.71 | −7.83 |

TABLE 2-continued

| | 5HT2B | | | |
| --- | --- | --- | --- | --- |
| Parameters | Compound of Formula (R)-1 | Compound of Formula (S)-1 | R-MDMA | S-MDMA |
| Glide Energy | −32.98 | −36.32 | −31.82 | −33.79 |
| *Glide evdw | −24.19 | −24.24 | −21.86 | −23.09 |
| **Glide ecoul | −8.80 | −12.08 | −9.6 | −10.70 |

*Glide evdw stands for van der Waals energy.
**Glide ecoul stands for Coulomb energy.

All items are involved in the Glide gscore algorithm.

As can be seen from the docking scores in Table 1 and Table 2, in a manner similar to S-MDMA, the compound of Formula (S)-I molecule binds with stronger affinity to 5HT$_{2B}$ compared to its corresponding R enantiomer.

b. Predicted IC$_{50}$

In silico studies (QSAR and docking) are useful tools to understand drug mechanisms, and they are relatively cheaper and faster than experiments. A QSAR model was created for each monoamine transporter. Additionally, the docking properties of phenethylamines were investigated.

QSAR: DAT, SERT and NET IC$_{50}$ values were collected from the literature for 73 phenethylamines. Three different software's were used for descriptor calculations, and almost 2000 descriptors were calculated. Highly correlated descriptors were eliminated before multi-linear regression (MLR) analysis. All descriptors were merged with experimental inhibition values in QSARiNS software. The multi-Criteria Decision-Making tool of QSARiNS was used to pick the best model.

Docking: Selected compounds were built by MOE as +1 charged (extra hydrogen is always on amine). The energy minimization tool of MOE was used to optimise molecular geometries. Transporter and receptor 3D structures were downloaded from Protein Data Bank (PDB) website as shown in Table 3. Unnecessary components of PDB files were deleted. The energy minimization tool was used to optimise the 3D structure of proteins.

TABLE 3

| Protein structure of transporters and receptors selected for QSAR modeling | | | | | |
| --- | --- | --- | --- | --- | --- |
| Protein Information | PD BID | Reference | Active Site 1 | Active Site 2 | Conformation |
| SERT | 7LIA | Yang, D., & Gouaux, E. (2021). *Science Advances*, 7(49), eabl3857 | Ser559, Glu494, Phe556, Tyr579, Pro499, Pro561 | Asp98, Ile172, Asn177, Tyr176, Thr439, Gly442, Tyr95 | Outward |
| DAT | 4XP1 | Wang et al., (2015), *Nature*, 521(7552), 322-327 | | Phe43, Asp46, Ala117, Val120, Asp121, Tyr124, Ser422, Gly425, Phe325 | Outward |
| 5-HT2A | 6A93 | Kimura et al., (2019), *Nature Structural & Molecular Biology*, 26(2), 121-128 | Val156, Phe339, Phe340, Thr160, Ser159, Phe243, Ile163, Phe332, Trp336, Tyr370, Asp155 | | |
| 5-HT2B | 7SRQ | Cao et al., (2022), *Neuron*, 110(19), 3154-3167 | Asp135, Ala225, Gly221, Met218, Leu362, Phe340, Phe341, Val136 | | |

The predicted IC$^{50}$ (mM) values of the test molecules generated based on the QSAR developed as described above are presented in Table 4.

TABLE 4

Predicted IC$_{50}$ (μM) values of Test molecules based on QSAR model developed in-house

| Molecule | DAT | SERT | NET | DAT/SERT (calculated*) |
|---|---|---|---|---|
| R-I: (R)-2-[(2H-1,3-benzodioxol-5-yl)methyl]pyrrolidine | 23.20 | 0.51 | 0.53 | 0.022 |
| S- I (S)-2-[(2H-1,3-benzodioxol-5-yl)methyl]pyrrolidine | 11.14 | 0.48 | 0.42 | 0.043 |
| S-MDMA | 3.76 | 1.44 | 1.06 | 0.383 |
| R-MDMA | 86.10 | 0.88 | 2.18 | 0.010 |

*DAT/SERT ratio = 1/DAT IC50:1/SERT IC50

As stated in Liechti 2015 "Many novel psychoactive substances interact with biogenic amine neurotransmitter transporters. Amphetamines, including methamphetamine and MDMA, inhibit the dopamine, serotonin and noradrenaline (norepinephrine) transporter (DAT, SERT, NET, respectively) and release these monoamines through the respective transporter. Methamphetamine predominantly increases dopamine and noradrenaline. MDMA mainly increases serotonin and noradrenaline. The entactogenic effects of MDMA are generally considered to depend on its serotonergic effects. Consequently, substances which predominantly release serotonin, like MDMA, can be expected to produce MDMA-like entactogenic effects. In contrast, psychostimulants such as methamphetamine or methylphenidate mainly enhance dopaminergic neurotransmission. Dopamine mediates the reinforcing and addictive properties of drugs of abuse. In contrast, an increase in the serotonergic properties of a substance is associated with a reduced potential for addiction. Consequently, the relative dopaminergic to serotonergic properties in vitro (dopamine/serotonin transporter inhibition ratio) of a novel substance can be determined as a useful marker for its potential clinical psychotropic and acute toxic effects. Serotonin release and a DAT/SERT inhibition ratio of typically 0.01-0.1 are expected to result in subjective drug effects like those of MDMA or other empathogens." (Liechti M. (2015). *Swiss Medical Weekly*, 145(0304), w14043.)

Predicted IC$_{50}$ (Table 4) for (R)-I, (S)-I indicate that R-I is expected to behave much like R-MDMA. R-MDMA has a well-established lower toxicity potential than its S-enantiomer counterpart and racemic MDMA (Pitts et al., (2018) *Psychopharmacology*, 235(2), 377-392).

Example 7: Behaviour Experiments a. Social Interaction Testing

A social interaction test that has been used to test the effects of MDMA, specifically to test prosocial effects of MDMA, is described in Morley and McGregnor Eur J Pharmacol. 2000; 408:41-9, and is used to test the exemplary and comparative compositions of the application.

In order to familiarize subjects (mice) with the testing procedure and screen out aggressive subjects, the social interaction test is performed twice. During the first session, subjects receive injections of exemplary compositions of the application, comparative compositions or saline, and are isolated in clean cages for 30 minutes. Each subject is then paired with an unfamiliar weight-matched conspecific from the same treatment group in a 30×18 cm clear Plexiglas testing chamber for 10 minutes. An experimenter is present during the first test day to separate aggressive subjects. Any removed subjects are replaced with new naïve subjects so that each treatment condition has an equal number of non-aggressive subjects.

The second test session is performed 48 hours later using the same pairs, treatments, and procedure except that an experimenter is not present in the room during testing. While in the testing arena, subjects are free to move around and interact, allowing a diverse range of observable behaviors. On the second test day, the social pairings are videotaped and the duration of social behavior is quantified using JWatcher or BORIS (Friard and Gamba, Methods Ecol Evol. 2016; 7 (11) 1325-1330) by an observer blind to the experimental conditions. The durations of 3 behaviors are scored: anogenital investigation (sniffing the conspecific's anogenital area), general investigation (non-anogenital sniffing, grooming, and following the conspecific), and adjacent lying (side-by-side contact or huddling). These behaviors are averaged for each pair and then summed to produce a total social interaction score, upon which statistical analysis is performed.

b. Locomotor Behaviour

Effects of exemplary compositions of the application and comparative compositions on locomotor activity is tested in 45×39×37 cm open field chambers with 16×16 photocells positioned 2.5 cm off the chamber. Mice are treated with the exemplary compositions of the application, comparative compositions or saline (n=13/group) immediately before being placed into the chambers for 1 hour. Testing is performed in a dark, enclosed space. Accumulative beam breaks of adjacent photocells are recorded as the measure of locomotor activity.

c. Fear Conditioning and Extinction

The effects of exemplary compositions of the application and comparative compositions on conditioned freezing are evaluated using an established protocol (Young et al., 2015, Transl Psychiatry. 5:1-8) previously used to test racemic MDMA. For consistency with this prior study, C57BL/6 mice are used in this experiment. Briefly, mice are exposed to cued fear conditioning on day 1, fear extinction training on day 3, and extinction testing on day 4. Cued fear conditioning consists of a single pairing of a conditioned stimulus (CS) tone (80 dB, 4.5 kHz, 30 s) and an unconditioned stimulus (US) foot shock (1 mA, 2 s). Extinction training is carried out 48 hours later in a new context from conditioning. R-MDMA, S-MDMA, or saline (n=6-7/group) were administered on day 3, 30 minutes before training. Extinction training consists of a sub-optimal regimen of 4 CS-tone re-exposures separated by 45 seconds. Extinction testing is performed 24 hours later to determine the lasting effect of treatment on conditioned freezing. Extinction testing is performed in the same context as training and followed the same procedure except that no treatments is administered. Throughout these experiments, percent freezing (the conditioned response) is estimated by scoring the presence or absence of non-respiratory movement every 5 seconds.

d. Social Preference and Locomotor Activity (LMA) Studies in Rodent Models Introduction Autism spectrum disorder (ASD) is a complex neurodevelopmental disorder defined by two main clusters of behaviors. The first group of behaviors is defined by deficits in social communication and social interaction, while the second group of behaviors consists of repetitive and inflexible patterns of behaviors, interests, and thoughts. In 2016, the Autism and Developmental Disabilities Monitoring Network estimated ASD prevalence at 1 in 54 children, and stated that ASD was 4.3 times more prevalent among boys compared to girls. Over the last several decades, the reported incidence of ASD has increased in the US, but the etiology of ASD remains poorly understood.

To better understand the neurological basis of ASD, rodent models of ASD have been developed for research. The BTBR T+Itpr3tf/J mouse (BTBR), originally bred for studies on insulin-resistance, diabetes-induced nephropathy and phenyloketonuria, was identified approximately a decade ago as displaying strong and consistent autism-relevant behaviors. Identification of novel drugs which increase sociability and decrease repetitive behaviors in the autism-like BTBR mouse and in the C57BL/6J (C57) background stock may be therapeutically useful in the context of social anxiety, generalized anxiety and/or ASD The studies described herein used male BTBR and C57 mice to evaluate the effects of racemic 3,4-methylenedioxymethamphetamine (MDMA), R/S)-2-[(2H-1,3-benzodioxol-5-yl)methyl]pyrrolidine ((R/S)-1), it's individual enantiomers ((R)-I and (S)-I) in an autism-relevant assay of social preference, as well as in studies of the safety and abuse liability of these drugs.

In three-dimensional space, these enantiomers would be distinguished from one another as non-superimposable mirror images, like left and right hands, based on whether the group bonded to the chiral carbon projects above or below the plane of the rest of the molecule. Pharmacologically, enantiomers can have very different biological effects, including quantitative differences in potency and effectiveness and qualitative differences in the mechanism of action or interoceptive effects, because the two species "fit" differently into the binding pockets of relevant receptors. In the case of methamphetamine, the S(+)-enantiomer is an abused psychostimulant with potent and long-lasting psychoactive effects, while the R(−)-enantiomer is more than 100-fold less potent at eliciting any of these effects (because it "fits" the relevant receptors like a right hand in a left glove.) In the case of MDMA, both enantiomers are active at similar doses, although they elicit effects which are different in kind from one another. Based on their similar chemical structures, methamphetamine was chosen as a positive control compound against which to compare the effects of MDMA in the social preference tests. Both compounds were expected to elicit locomotor stimulant effects at large doses, but methamphetamine was not expected to elicit any pro-social effects.

General Animal Handling

Adult male C57 and BTBR mice were shipped to the University of Arkansas for Medical Sciences from Charles River Laboratories and The Jackson Laboratory, respectively. Upon arrival, mice were housed 3 per cage, according to strain, with food and water available ad lib. Mice were allowed to acclimatise to the UAMS facilities for at least 48 hours before any experimental procedures were performed.

Drug Administration

All drugs were dissolved in physiological 0.9% saline and administered at a constant volume of 1 ml/100 g body weight. Because all drugs utilized in these studies were synthesized as hydrochloride (HCl) salts, they were weighed as salts prior to the preparation of all solutions. All drugs at all concentrations are readily dissolved in an aqueous solution at normal pH. Injections of all drugs were administered intraperitoneally (IP) to mimic pharmacokinetic parameters typical of oral administration, without the behaviour-impairing effects of gavage stress.

Social Preference Testing Methods

This assay was conducted in adult male C57 and BTBR mice (n=6 per group) in a dedicated conditioning room where ambient light, sound, and human contact were tightly controlled.

Social preference chambers consisted of two polycarbonate boxes (13.5 cm wide×22.5 cm tall×31.0 cm deep), floored with rough-textured black ABS plastic, and connected to one another by a 1.25" PVC T-junction. An infrared photobeam emitter/detector array was mounted at each intersection of the T-junction and each preference compartment, and as a mouse traversed the apparatus, it would break the photobeam upon entry to or exit from each preference compartment. Beam breaks started or stopped a counter on an interfaced computer, allowing automated collection of time spent in each compartment. At the end of each test, data were reported as time (in seconds) spent in each compartment, the number of entries into each compartment, and the average time spent in each compartment following an entry. Social preference tests were conducted in an iterative manner, with each test subject completing four distinct phases as described below. Between testing sessions, chambers were sanitized by wiping the insides with a disinfectant product provided by the UAMS Department of Laboratory Animal Medicine. At the end of the week (upon completion of all phases of the procedure), each apparatus was disassembled and all parts were sanitized. No food or water were available during social preference sessions, but were available in the home cage immediately afterwards.

Phase 1—Habituation

A single habituation session occurred prior to preference testing, where each compartment contained an identical empty wire mesh pencil cup (9.0 cm diameter×10.5 cm tall). During this session, mice were weighed, no injection was administered, and subjects were introduced into the T-junction and allowed to explore both preference compartments for 30 minutes. This habituation session was conducted as a procedural control to allow animals to become accustomed to the apparatus and to screen out any animals with a strong initial bias for one of the two compartments. An a priori exclusion criterion was established such that any subjects spending more than 75% of the total time in one single preference compartment would be excluded from further study, but no subjects in these studies met this standard for exclusion. Habituation sessions always occurred on Mondays or Tuesdays to prevent any weekend testing.

Phase 2—Novelty Preference

A single novelty preference session occurred the day after the habituation test, where one compartment contained an empty wire mesh cup and the other compartment contained an identical wire mesh cup with a novel dummy mouse inside. The position of the dummy mouse (left or right compartment) was counterbalanced across subjects. Dummy mice were constructed from 2.5" lengths of white ¾" PVC pipe, with a zip tie attached to one end (to mimic a tail) and two red dots drawn on the other end (to mimic eyes.) During this session, mice were weighed, administered an injection, and returned to their home cage for a 30 min pretreatment period. Mice were then introduced into the T-junction and allowed to explore both preference compartments for 15 minutes. These tests were conducted as a procedural control to ensure that any observed drug effects were not simply due to enhancement of the innate novelty preference of mice.

Novelty preference sessions always occurred on Tuesdays or Wednesdays to prevent any weekend testing.

Phase 3—Sociability Testing

Figure 4:
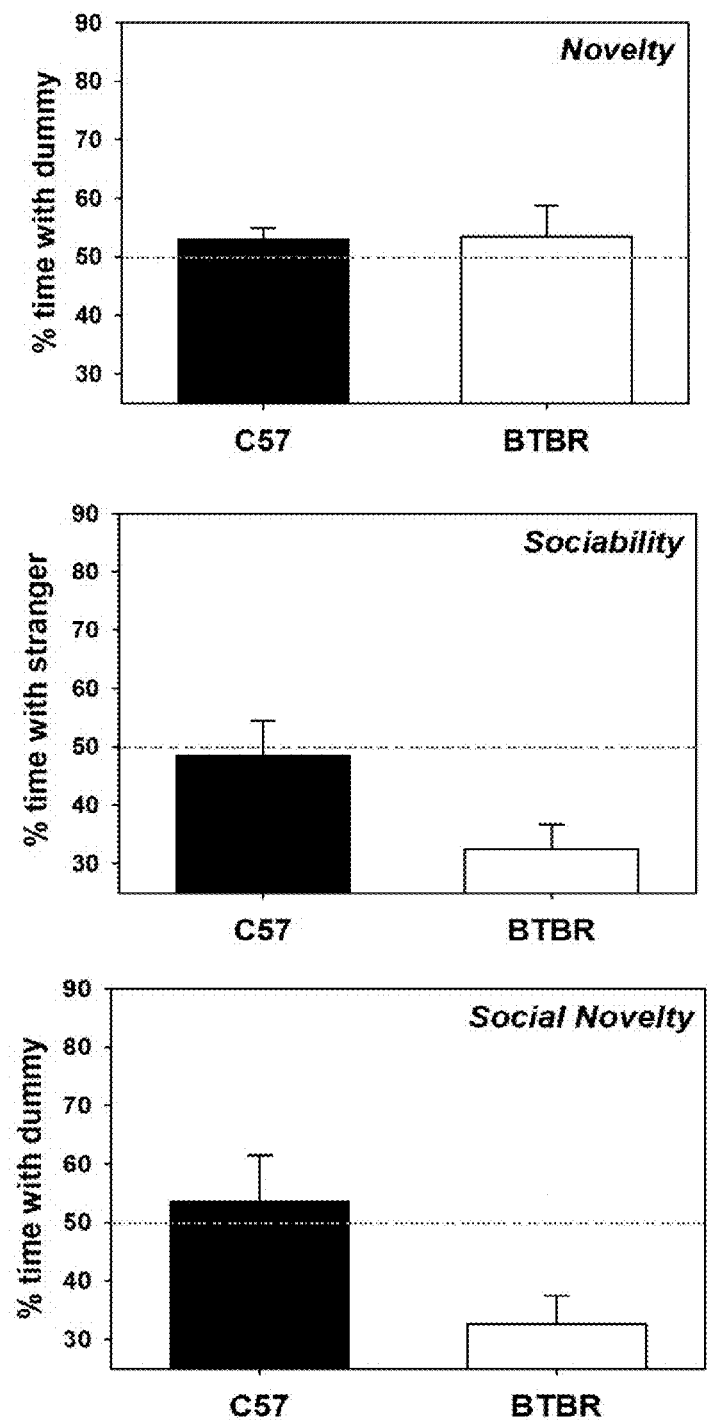
FIG. 4 are graphs showing baseline strain differences in preference during each phase of the social preference procedure in C57 (filled bars) and BTBR (open bars) mice administered saline injections before testing. Bars represent group means, and error bars represent standard error mean (SEM). Note that both strains exhibit a comparable indifference during the novelty preference control test (top panel), but consistent with their autism-like phenotype, BTBR mice show social avoidance in the sociability (middle panel) and social novelty (bottom panel) phases.

A single sociability session occurred the day after the novelty preference test, where one compartment contained a wire mesh cup with a dummy mouse inside while the other compartment contained a male NIH Swiss stranger mouse inside the previously empty cup (see FIG. 4). The wire mesh cups allowed visual, olfactory, auditory, and limited tactile contact, but prevented aggressive behaviors which may otherwise have resulted in injury. The position of the dummy mouse (left or right compartment) remained the same for each subject as during the novelty test the day before, thereby counterbalancing the position of the stranger mouse across subjects. NIH Swiss stranger mice were similar in mass and appearance to the dummy PVC mice, and were housed separately from the experimental subjects (C57 and BTBR mice) in the colony facility. The first time the experimental subjects ever encountered the stranger mice was when they entered the compartment where they were contained. During this session, mice were weighed, administered the same injection as the day before, and returned to their home cage for a 30 min pretreatment period. Mice were then introduced into the T-junction and allowed to explore both preference compartments for 15 minutes. Sociability tests always occurred on Wednesdays or Thursdays to prevent any weekend testing.

Phase 4—Social Novelty Preference

Figure 5:
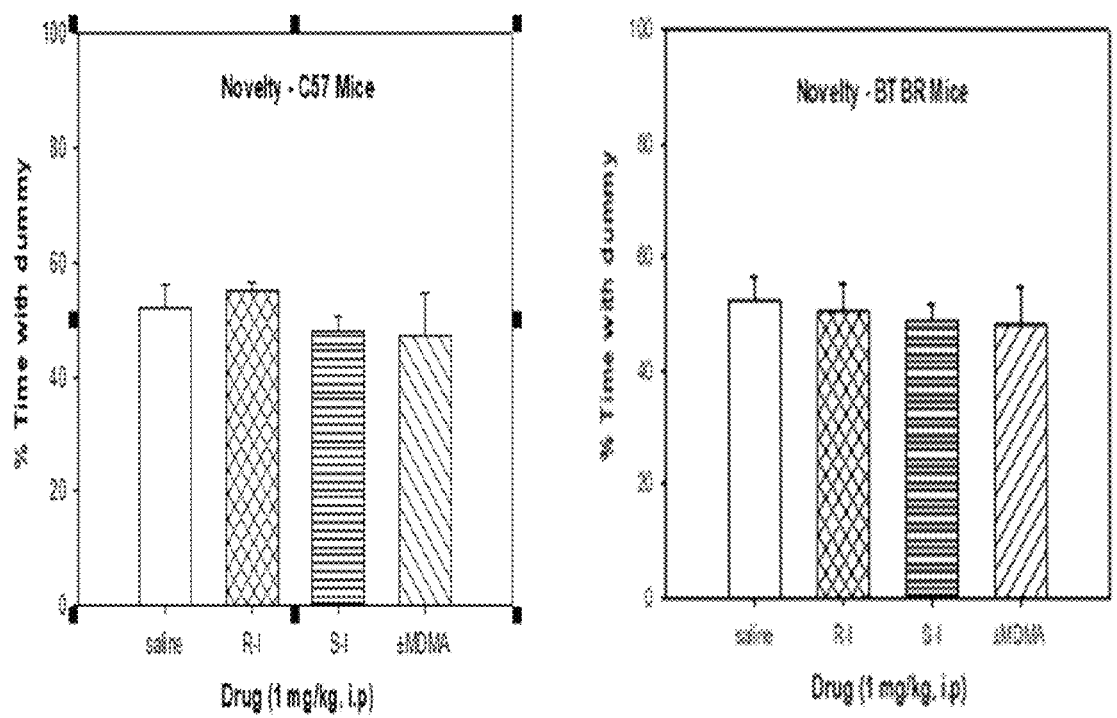
FIG. 5 are graphs showing the effect of 1 mg/kg of saline (first bar from left), (R)-I (cross hatched bar—second bar from left), (S)-I (horizontal lines—third bar from left) and racemic MDMA (diagonal lines-fourth bar from left) on time spent with the dummy mouse during the novelty preference test in C57 mice (left panel) and BTBR mice (right panel). Note that C57s and BTBRs receiving saline display essentially identical behaviour in this test, exhibiting a small preference for the novel dummy mouse.

A single social novelty preference session occurred the day after the sociability test, where one compartment contained a wire mesh cup with the same NIH Swiss mouse from the previous day inside (referred to now as the "familiar" mouse) while the other compartment contained a new male NIH Swiss stranger mouse inside the cup which previously contained the dummy mouse during the sociability test (see FIG. 5). The wire mesh cups allowed visual, olfactory, auditory, and limited tactile contact, but prevented aggressive behaviors which may otherwise have resulted in injury. The position of the now familiar NIH Swiss mouse (left or right compartment) remained the same for each subject as during the sociability test the day before, thereby counterbalancing the position of the new NIH Swiss stranger mouse across subjects. As before, the new NIH Swiss stranger mice were housed separately from the experimental subjects (C57 and BTBR mice) in the colony facility, and the first time the experimental subjects ever encountered them was when they entered the compartment where they were contained. During this session, mice were weighed, administered the same injection as the day before, and returned to their home cage for a 30 min pretreatment period. Mice were then introduced into the T-junction and allowed to explore both preference compartments for 15 minutes. Social novelty tests always occurred on Thursdays or Fridays to prevent any weekend testing.

Drug Effect on Locomotor Activity

Quantifying total entries into the preference compartments provides a proxy measurement for locomotor stimulant effects of the various doses of the various test drugs. This establishes a limit to the drug doses that can be tested in the social preference procedure, as induction of locomotor stimulant effects confounds preference assessments (because mice stop attending to the social stimuli in each compartment and instead spend their time engaged in locomotor behavior.) Motor activity varies across the distinct phases of social preference testing, in part because the habituation session is twice as long (30 minutes) as the novelty, sociability, and social novelty tests (15 minutes each), but also because mice emit high levels of exploratory behavior in novel environments. Thus, as familiarity with the test apparatus increases over successive exposures to the chambers, the number of entries decreases.

Figure 3:
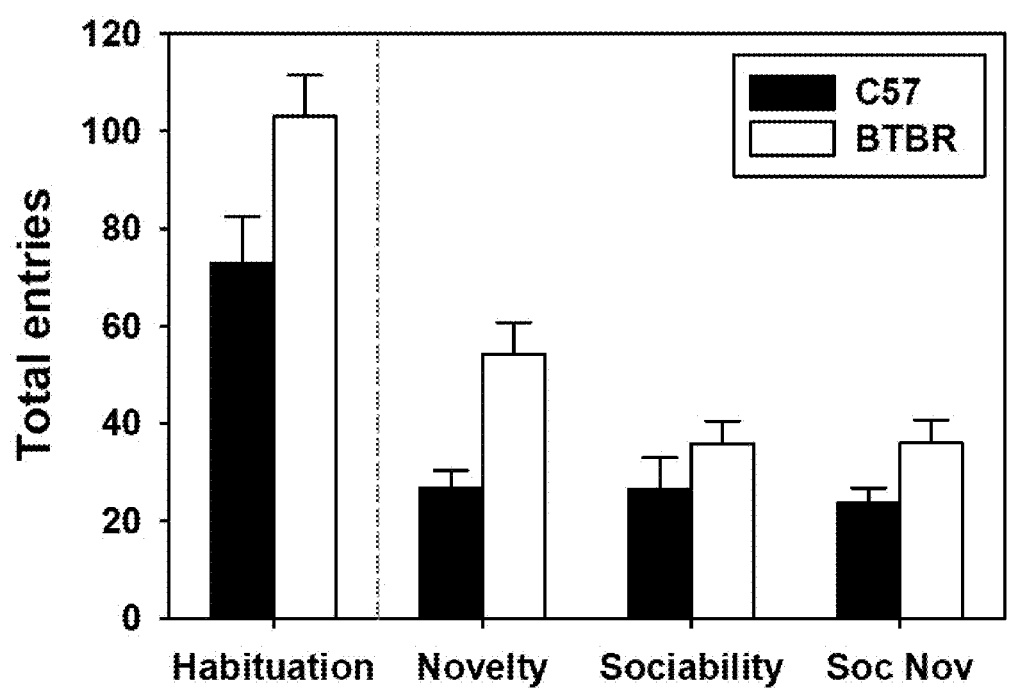
FIG. 3 is a graph showing total entries into the testing compartments during each phase of the social preference procedure in C57 (filled bars) and BTBR (open bars) mice administered saline injections prior to the novelty, sociability and social novelty (Soc Nov) tests.

FIG. 3 illustrates this decreasing trend in motor activity in C57 (filled bars) and BTBR (open bars) in the absence of any drug injections. It was noted that baseline differences in locomotor activity were also observed between the C57 and BTBR mice in the absence of drug injection, such that BTBR subjects always exhibited more entries during every phase of the social preference procedure.

Because baseline activity for C57 and BTBR mice does not change from the sociability to the social novelty test (the final testing phase, when mice are at maximum familiarity with the apparatus), drug effects during this phase was focused on to determine locomotor stimulant effects of the various treatment drugs. (Note that entries were collected for every test, but drug effects on entries during earlier phases may be less reliable due to the confounding influence of changing familiarity with the apparatus across phases.)

In C57 mice (see FIG. 4, closed bars), approximately 20 entries were observed following saline administration.

C57 mice (see FIG. 5 left panel) and BTBR Mice (see FIG. 5 right panel) exhibited no strong preference for the dummy mouse over the empty cup, as approximately equal amounts of time were spent in each compartment following saline administration.

Injection of (R)-I, (S)-I or racemic MDMA had no systematic effects on novelty preference at this dose. Because none of the test drugs increased novelty preference, any enhancement of social preference in subsequent tests is unlikely to be confounded by novelty-related effects, such as changes in the motivational properties of novel objects, which might otherwise be confused for pro-social effects.

Drug Effects on Sociability

Figure 6:
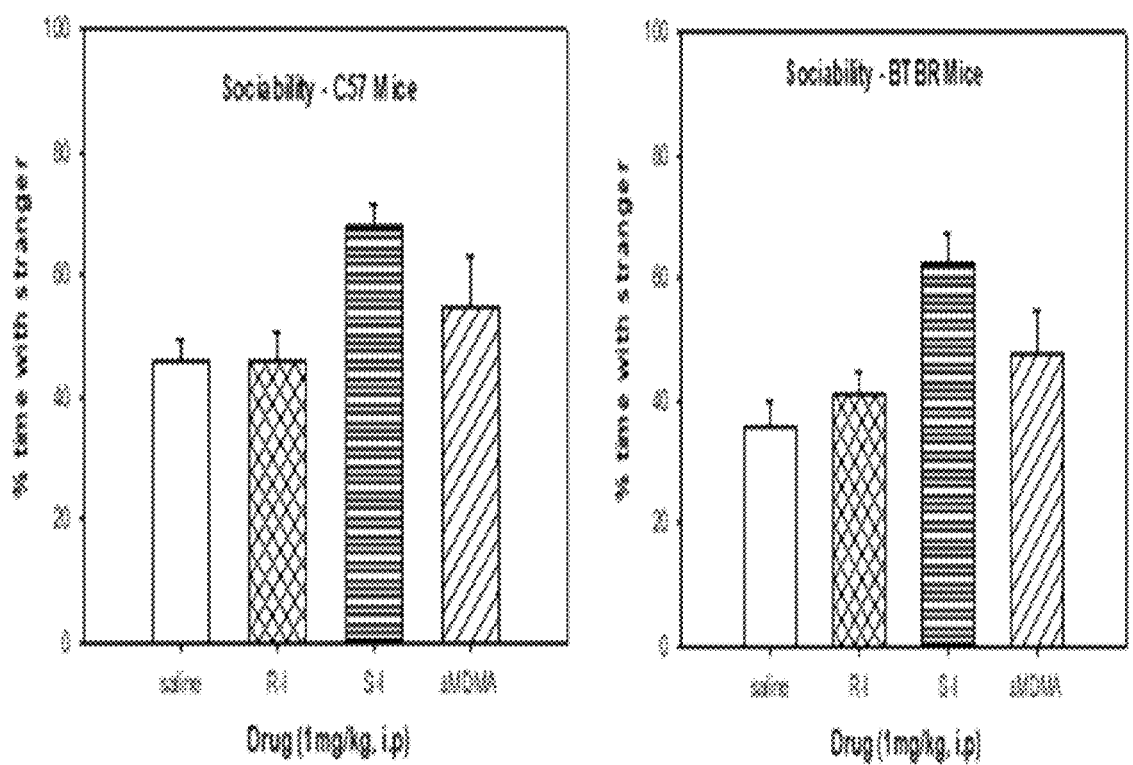
FIG. 6 are graphs showing the effects of 1 mg/kg of i.p injection of saline (first bar from left), (R)-I (cross hatched bar—second bar from left), (S)-I (horizontal lines—third bar from left) and racemic MDMA (diagonal lines-fourth bar from left) on time spent with stranger mouse during the sociability test in C57 mice (left panel) and BTBR mice (right panel).

C57 mice slightly avoided the stranger mouse, as slightly less time was spent in the compartment containing the stranger mouse than in the compartment containing the dummy following the saline administration (see FIG. 6 left panel). In BTBR mice (see FIG. 6 right panel), the expected autism-like social decrement was observed following saline administration, where mice exhibited a strong avoidance of the stranger mouse.

Injection of 1 mg/kg (R)-I, racemic MDMA had no impact on the sociability of the C57 mice. However, injection of 1 mg/kg (S)-I elicited a slight increase in time spent with the stranger mouse, producing a moderate preference for the stranger over the dummy.

Figure 7:
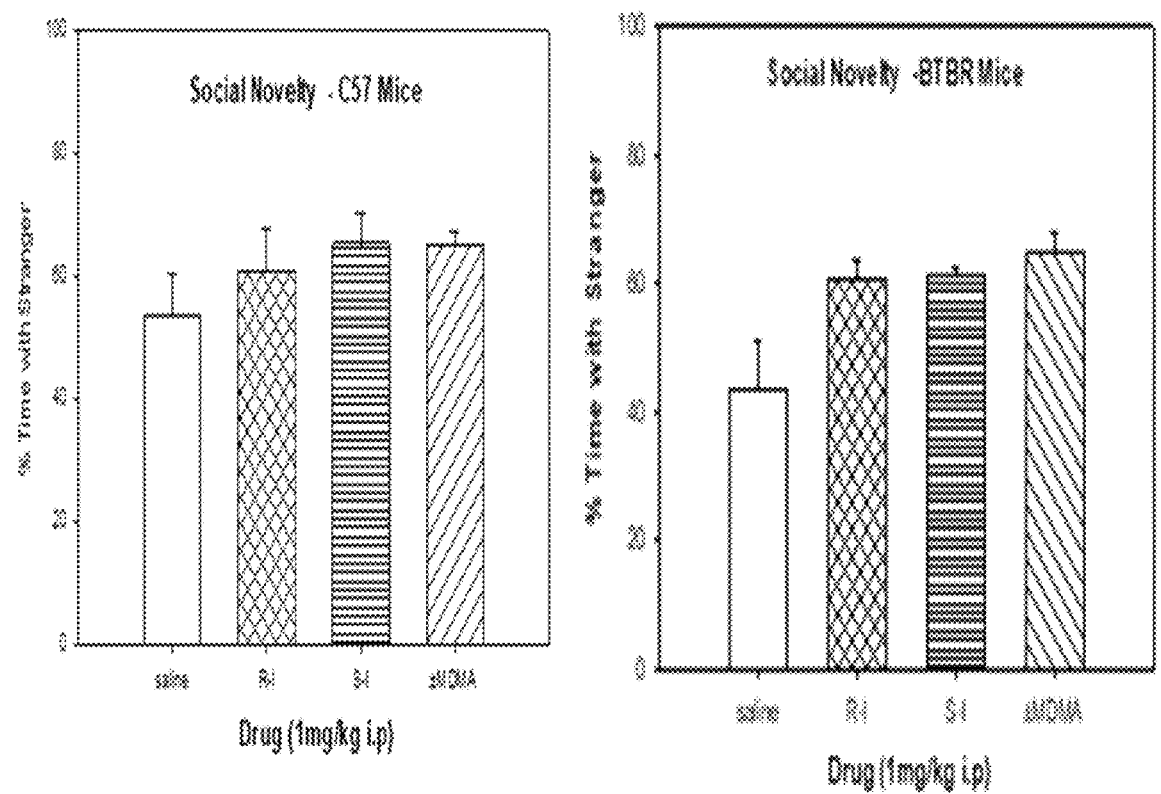
FIG. 7 are graphs showing effects of 1 mg/kg of saline (first bar from left), (R)-I (cross hatched bar—second bar from left), (S)-I (horizontal lines—third bar from left) and racemic MDMA (diagonal lines-fourth bar from left) on time spent with stranger mouse during the social novelty preference test in C57 (left panel) and BTBR (right panel) mice. Note that BTBRs receiving saline display the expected autism-like social avoidance in this test, exhibiting avoidance of the stranger mouse.

In BTBR Mice, (S)-I elicited a strong response in sociability. However, (R)-I and racemic MDMA have a minor increase in the sociability response Drug effects on social novelty preference C57 mice exhibited a small preference for the new stranger mouse, as slightly more time was spent in the compartment containing the new stranger mouse than in the compartment containing the now familiar mouse following saline administration (see FIG. 7, left panel). In BTBR mice (see FIG. 7, right panel), the expected autism-like social decrement was observed following saline administration, where mice exhibited a small avoidance of the stranger mouse.

Figure 8:
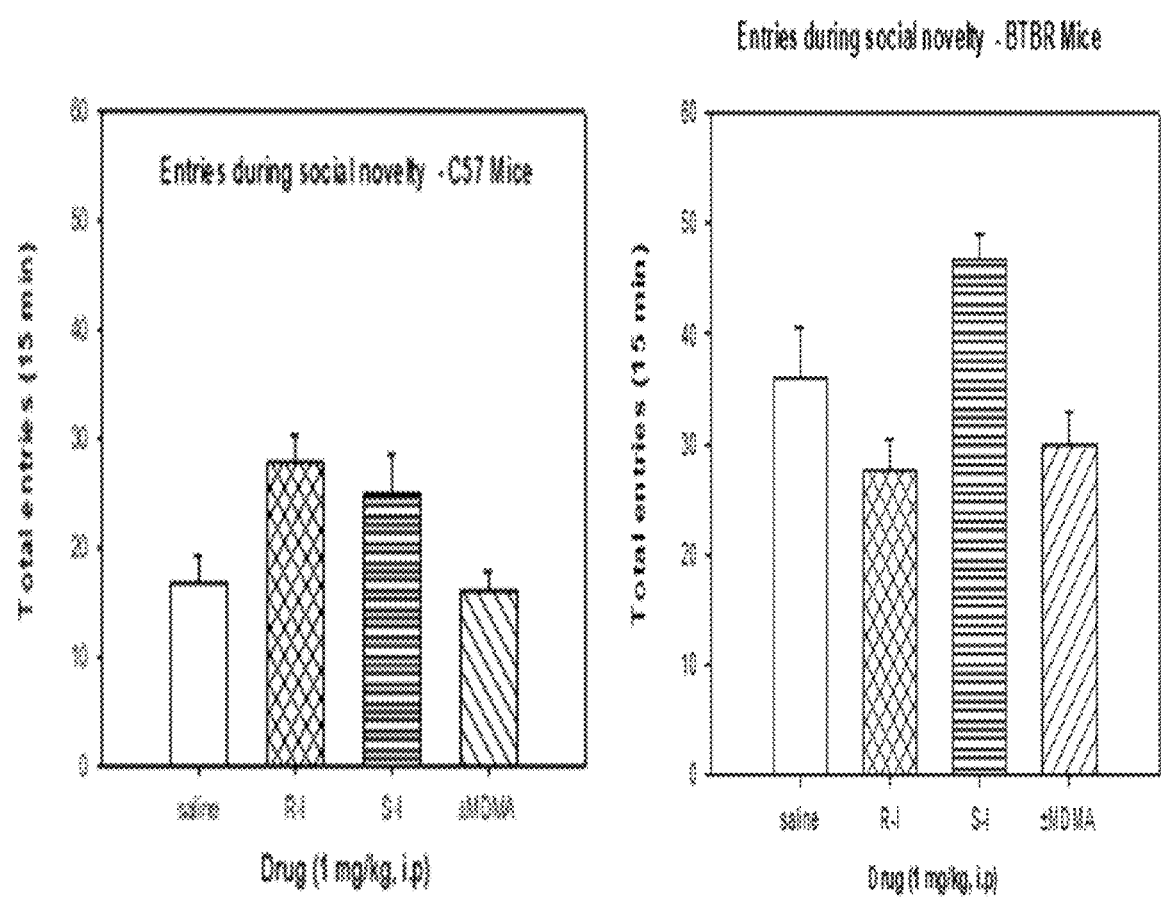
FIG. 8 are graphs showing the effects of 1 mg/kg (i.p) of saline (first bar from left), (R)-I (cross hatched bar—second bar from left), (S)-I (horizontal lines—third bar from left) and racemic MDMA (diagonal lines-fourth bar from left) on compartment entries during the social novelty test in C57 mice (left panel) and BTBR mice (right panel).

Relative to saline, injection of (R)-I and (S)-I in C57 mice at 1 mg/kg only slightly increased the total entries during social novelty, while racemic MDMA had no effect at this dose (see FIG. 8, left panel). In BTBR mice, approximately 40 entries were observed following saline administration, consistent with their greater baseline level of locomotor effects previously described and shown in FIG. 3.

Figure 9:
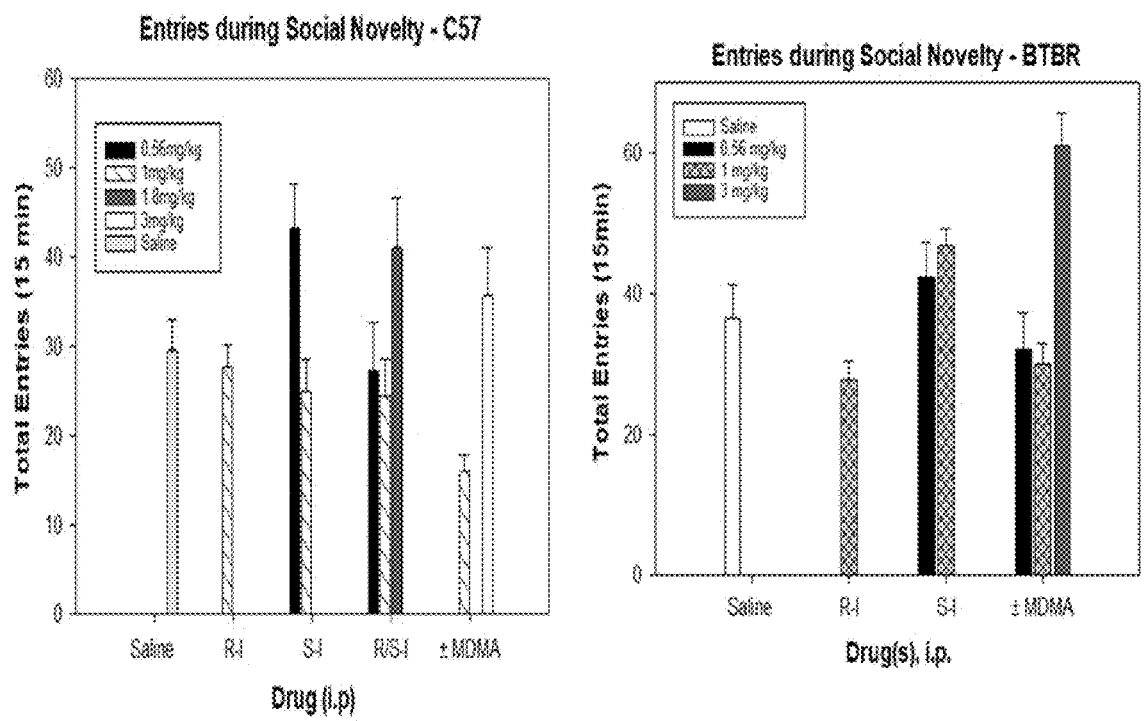
FIG. 9 are graphs showing: A the effects of saline (first bar from left), or various doses of (R)-I (second bar from left), (S)-I (horizontal lines—third set of bars from left), (R/S)-I (fourth set of bars from left) and racemic MDMA (fifth set of bars from left) on compartment entries during social novelty test in C57 mice (left panel) and BTBR mice (right panel); and B the effects of saline (first bar from left), or various doses of (R)-I (second bar from left), (S)-I (horizontal lines—third set of bars from left), (R/S)-I (fourth set of bars from left) and racemic MDMA (fifth set of bars from left) on time spent with stranger mouse during the social novelty preference test in C57 mice (left panel) and BTBR mice (right panel)
Figure 9:
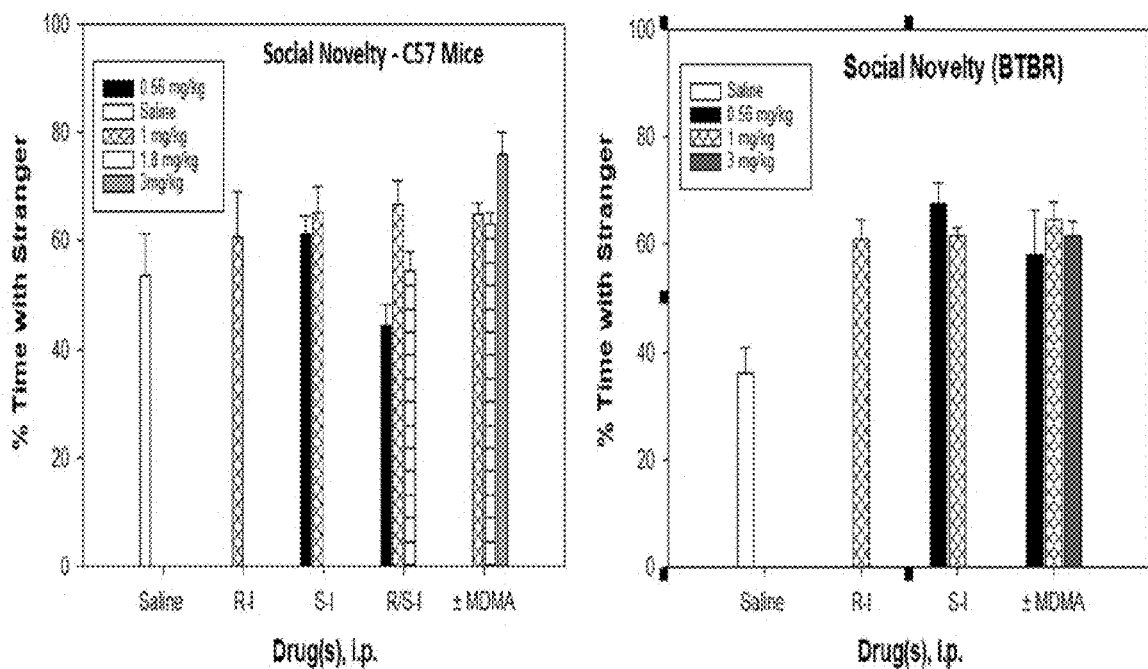

Injection of 1 mg/kg of (S)-I substantially stimulated the BTBR mice (right panel, FIG. 8) compared to (R)-I, Racemic MDMA and saline. This stimulation seemed to increase with increasing dose in BTBR mice (FIG. 9A, right panel), but reverses in C57 mice (see Figure FIG. 9A, left panel).

In BTBR mice (Figure FIG. 9B, right panel), the pro-social response documented by 1 mg/kg of (R)-I was similar to that of 3 mg/kg of Racemic MDMA. Thereby demonstrating that (R)-I is a more potent drug when tested for social preference in BTBR mice.

Similarly, in C57 mice (Figure FIG. 9, left panel), the pro-social response of mice upon injection of 1 mg/kg of (R)-I was similar to that as documented when the mice are injected with 1.8 mg/kg racemic MDMA. Interestingly, (R/S)-I had the strongest pro-social response at 1 mg/kg, and at 1.8.mg/kg the response drops.

e. Drug Effects on Conditioned Place Preference Rodent Models

The same 2-compartment chambers as described above in the social preference studies for conditioned place preference. For these studies, compartments are differentiated by floor texture (rough black plastic vs steel punch plate) and wall pattern (vertical vs. horizontal stripes.) An initial preference/habituation test was first run where mice were able to freely traverse the apparatus for 30 minutes. The following day, mice were assigned to receive saline in one compartment and drug in the other. Saline pairings occurred in the morning, drug pairings occurred in the afternoon, and were separated by at least 4 hours, during which time mice returned to their home cages. Three such pairings were performed, where mice were injected, returned to the home cage for a 15 min pretreatment period, then confined to the injection-appropriate compartment for 30 minutes. Half the subjects (within strain) received drug pairings on the plastic floor+vertical stripes side, and the other half received drug pairings on the punch plate floor+horizontal stripes side. Counterbalancing was accomplished by assigning drug to the initially non-preferred side for all mice expressing a preference, then filling in the remaining slots with mice that did not express a preference in the initial trial. The post-conditioning preference test was identical to the initial preference/habituation session, where mice were freely able to traverse the apparatus for 30 minutes. Time spent in each compartment was recorded, and expressed as a preference score for the drug paired side (calculated as time spent in that compartment during the post-test—time spent there during the pre-test.) All preference and conditioning sessions were conducted under the same low light conditions as in the social preference tests.

Figure 21:
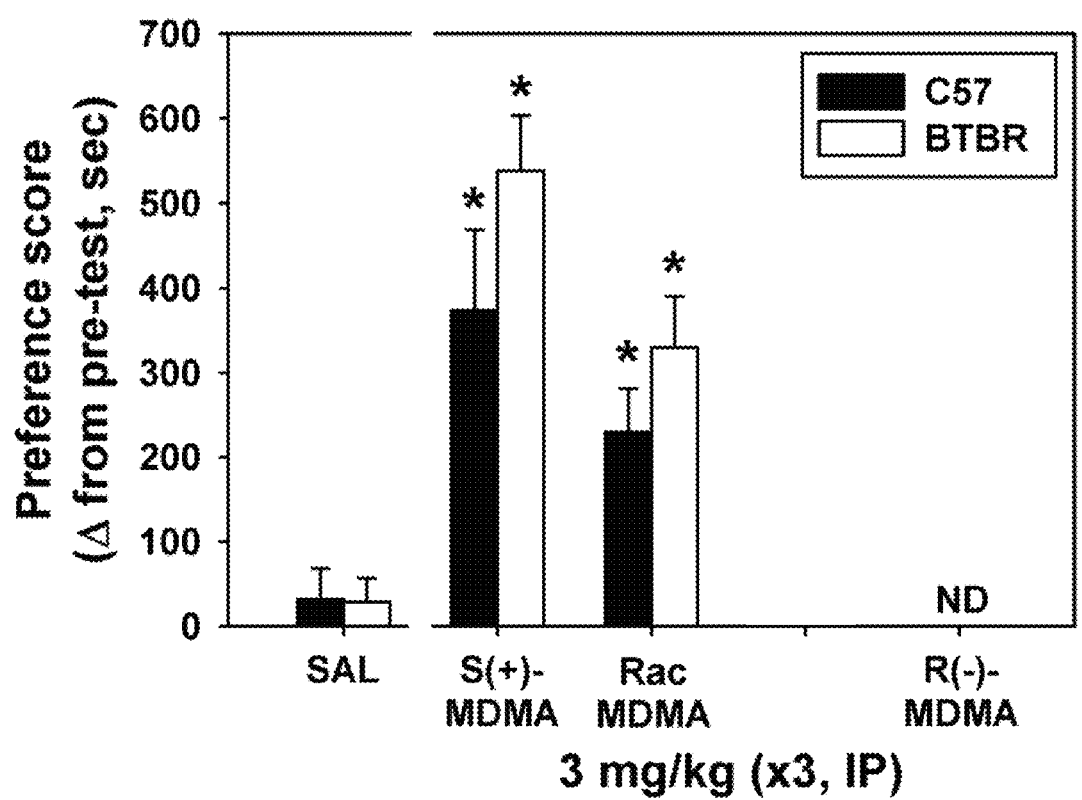
FIG. 21 is a graph showing the effects of saline or 3 mg/kg of MDMA (×3 pairings each) at various enantiomer ratios on place conditioning in C57 mice (black bars) and in BTBR mice (open bars).

FIG. 21 shows the effects of saline or 3 mg/kg of MDMA (×3 pairings each) at various enantiomer ratios on place conditioning in C57 mice (filled bars) and in BTBR mice (open bars). Saline administered in both compartments had negligible effects on place conditioning, and 3 mg/kg S-MDMA or racemic MDMA elicited significant place preferences in both C57 and BTBR mice. BTBR mice displayed a greater place preference than C57 mice, suggesting an increased sensitivity to rewarding effects of racemic MDMA (but note that a statistical comparison between the strains was not performed). 3 mg/kg R-MDMA was not tested because it had no significant effects at 10 mg/kg in either strain (see FIG. 22).

Figure 22:
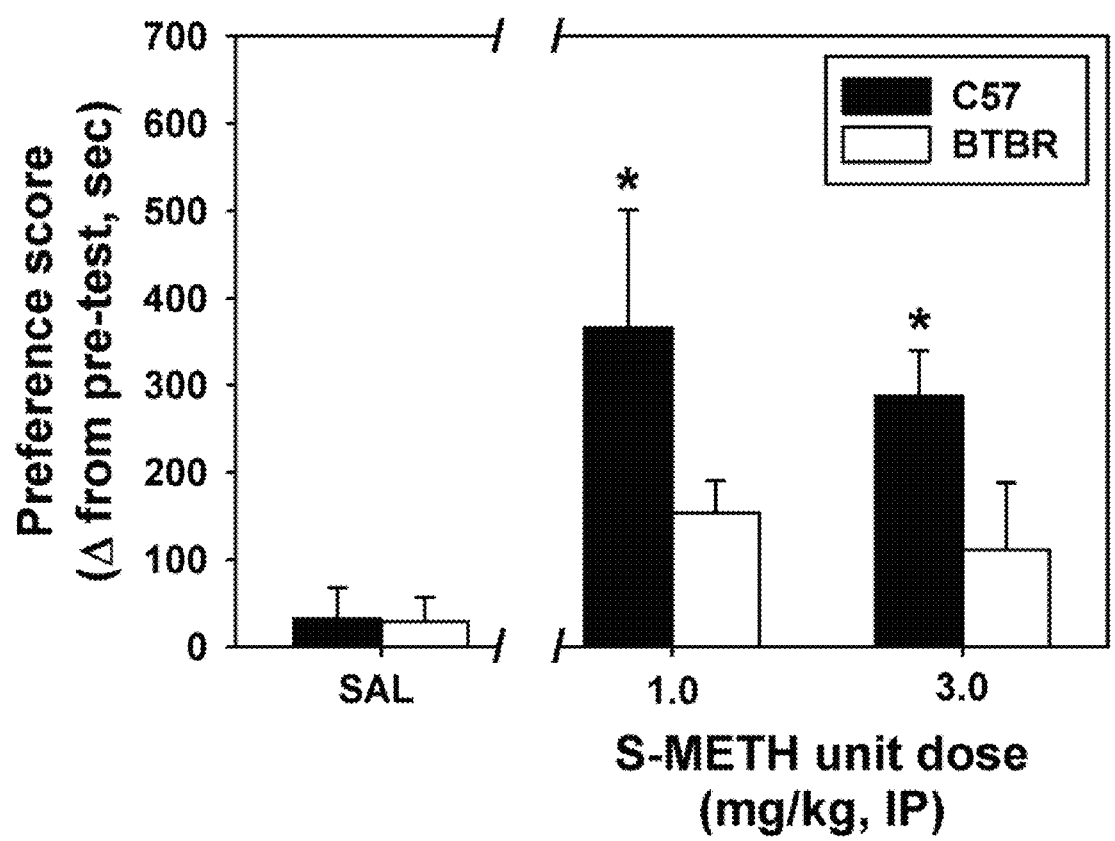
FIG. 22 is a graph showing the effect of saline, 1.0 or 3.0 mg/kg of S-METH (×3 pairings each) on place conditioning in C57 mice (filled bars) and in BTBR mice (open bars).

FIG. 22: Effects of saline, 1.0 or 3.0 mg/kg of S-METH (×3 pairings each) on place conditioning in C57 mice (filled bars) and in BTBR mice (open bars). Saline administered in both compartments had negligible effects on place conditioning, but 1.0 and 3.0 mg/kg S-methamphetamine (METH) elicited significant place preferences in C57 mice only (see FIG. 22). These results suggest that the apparent increased sensitivity to the rewarding effects of MDMA observed in BTBR mice is, therefore, not simply a general increase in sensitivity to all drugs. The effect may be specific to the MDMA-like compounds.

Figure 23:
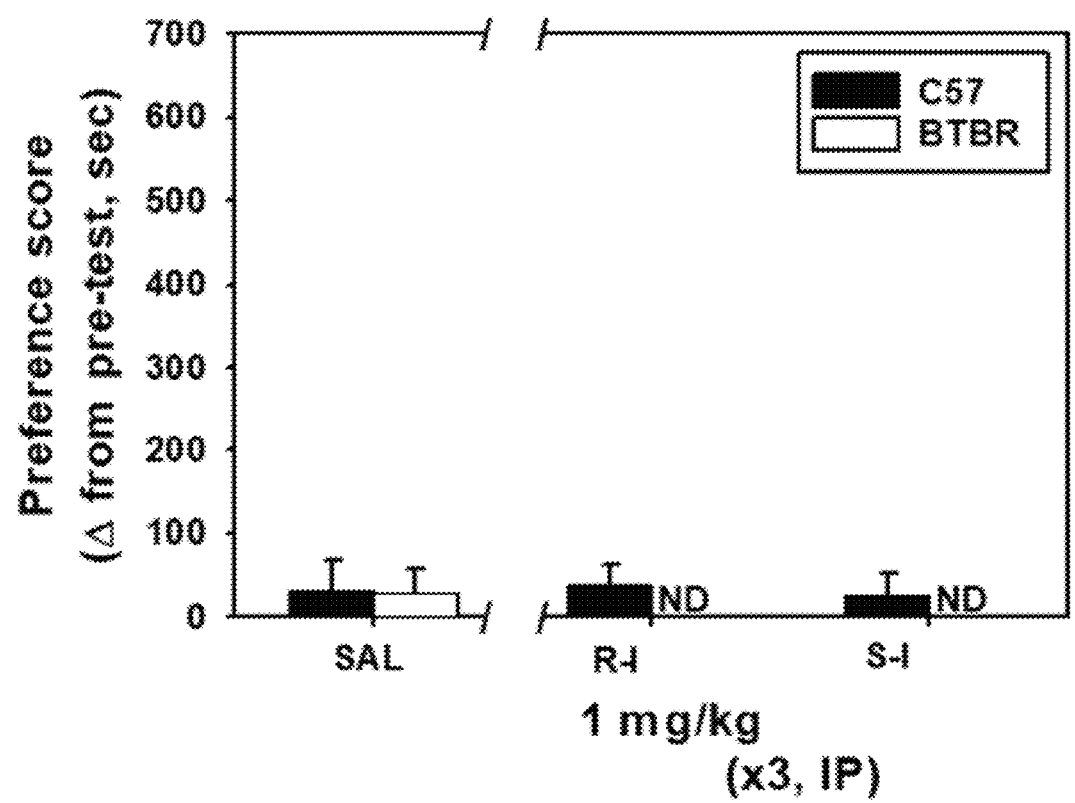
FIG. 23 is a graph showing the effects of saline, 1.0 mg/kg (R)-I or 1.0 mg/kg (S)-I (×3 pairings each) on place conditioning in C57 mice (filled bars) and in BTBR mice (open bars).

FIG. 23 shows the effects of saline, 1.0 mg/kg (R)-I or 1.0 mg/kg (S)-11 (×3 pairings each) on place conditioning in C57 mice (filled bars) and in BTBR mice (open bars). Saline administered in both compartments had negligible effects on place conditioning, and neither 1.0 mg/kg (R)-I nor 1.0 mg/kg (S)-I elicited significant place preferences in C57 mice. BTBR mice were not tested. Given the apparent increased sensitivity to rewarding effects of MDMA-like drugs in BTBR mice, this strain may display place preference with doses that are ineffective in C57 mice.

When 1 mg/kg (R)-I and (S)-I in C57 mice was tested relative to S-methamphetamine (tested at the same dose), both enantiomers had negligible effects on the mice (see FIG. 23).

3 mg/kg of Racemic MDMA and S-MDMA elicited significant place preferences in C57 and BTBR mice (see FIG. 22).

Example 8: Neurotoxicity Studies a. Neurotoxic Dosing and Tissue Collection

In a modified dosing regimen from Itzhak et al., Psychopharmacol. 2003; 166:241-248, subjects receive a total of four injections of exemplary compositions of the application, comparative compositions or saline given twice, two hours apart on two consecutive days. Subject are isolated during treatment and returned to their home cages 2 hours after the second daily dose. Following treatment, subjects are divided into two groups. 48 hours after the final injection, subjects from group 1 are anesthetized and transcardially perfused with 4% formaldehyde. Their brains are post-fixed overnight and then immersed in 15% sucrose for 48 hours, frozen in chilled methyl butane, sectioned at 35 μm, and stored at −20° C. until analysis by immunohistochemistry. Subjects in group 2 are euthanized by cervical dislocation 14 days after the last injection. Their brains are removed and prefrontal cortex, striatum, and hippocampus are rapidly dissected and stored at −80° C. for subsequent analysis by high-performance liquid chromatography (HPLC) or Western blot.

b. Body Temperature Monitoring

The effect of exemplary compositions of the application and comparative compositions on body temperature, given twice at a two-hour intervals, is monitored using a rectal thermometer (n=5/group). Measurements are taken every 30 minutes at an ambient room temperature of 22±2° C. During monitoring, mice are separated to individual holding cages.

c. Body Temperature Monitoring Studies in Rodent Models of Autism Spectrum Disorder Radiotelemetry of Core Temperature and Motor Activity Testing Methods Monoamine-mimetic agents can affect temperature control, particularly amphetamine derivatives such as MDMA, which has perhaps been most widely studied (Docherty & Green, (2010), *British Journal of Pharmacology*, 160(5), 1029-1044; Freedman et al., (2005), *Psychopharmacology*, 183(2), 248-256; Kendrick et al., (1977), *Annals of Internal Medicine*, 86(4), 381; Parrott, (2012), *Drug and Alcohol Dependence*, 121(1-2), 1-9). Thus, this study aimed to study the impact of the drug(s) of interest on the core body temperature of C57 and BTBR mice.

The radiotelemetry assay was conducted in adult male C57 and BTBR mice (n=6 per group) in a dedicated testing room where ambient light, sound, and human contact were tightly controlled.

Prior to surgical implantation of radiotelemetry probes, mice received 3 mg/kg meloxicam (IP), and anesthesia was induced with 4% inhaled isoflurane and maintained with 1-3% isoflurane (as needed) throughout the procedure at a flow rate of 1.5 litres/minute. The abdominal area of each animal was treated with depilatory cream, then sanitized with 3 alternating scrubs with iodine and alcohol. A rostral-caudal cut approximately 1.5 cm in length was made with sterile skin scissors, providing access to the intraperitoneal cavity. A cylindrical glass-encapsulated radiotelemetry probe (model ER-4000 E-Mitter, Mini Mitter, Bend, OR, USA) was then inserted. These probes measure 15.5 mm×6.5 mm and weigh approximately 1 gram. Incisions were closed (skin layer and muscle layer separately) using reverse cutting 5-0 Vicryl absorbable sutures for the muscle layer and 5-0 nylon suture material for the skin layer. Surgeries were carried out at least 7 days before initiation of experimental conditions, allowing time for incisions to heal and for animals to recover normal body weights. Following surgery, all implanted mice were individually housed in Plexiglas cages within the telemetry room for the duration of all experiments. Implanted transmitters produce activity- and temperature-modulated signals which are sent to a receiver (model ER-4000 Receiver, Mini Mitter Co., Inc.) underneath each cage. Following use, telemetry probes were removed from carcasses, wiped with alcohol swabs, and stored in the disinfectant solution until re-use.

At least 7 days after surgical implantation of radiotelemetry probes, mice in their individual home cages were placed atop a telemetry energizer/receiver, which powers probes and transmits their data to an interfaced computer. Upon initiation of an experimental session, the computer collects two data updates from the probes at 5 min intervals: core temperature (in ° C.) on one channel, and locomotor counts (in arbitrary units, depending on the relative position of the probe atop the receiver) on the other. After at least 60 minutes of baseline data collection, mice were removed from their cages, injected with saline or a given dose of a specific drug, then returned to the home cage 24 hours of data collection.

Food and water were always freely available in the home cage. Mice were injected with ascending doses of a given drug, with at least 48 hours separating doses. Because there are few studies of drug effects in BTBR mice, the first drug dose tested occasionally elicited unexpectedly large locomotor effects in these animals. In these cases, smaller drug doses were tested next, after a washout period of at least one full day.

Results—Core Body Temperature and Locomotor Activity

Effect of Saline Injection on Core Temperature and (Locomotor Activity) LMA in C57 and BTBR Mice [Establishment of Baseline and Characteristics of the Mice Species]

Figure 10:
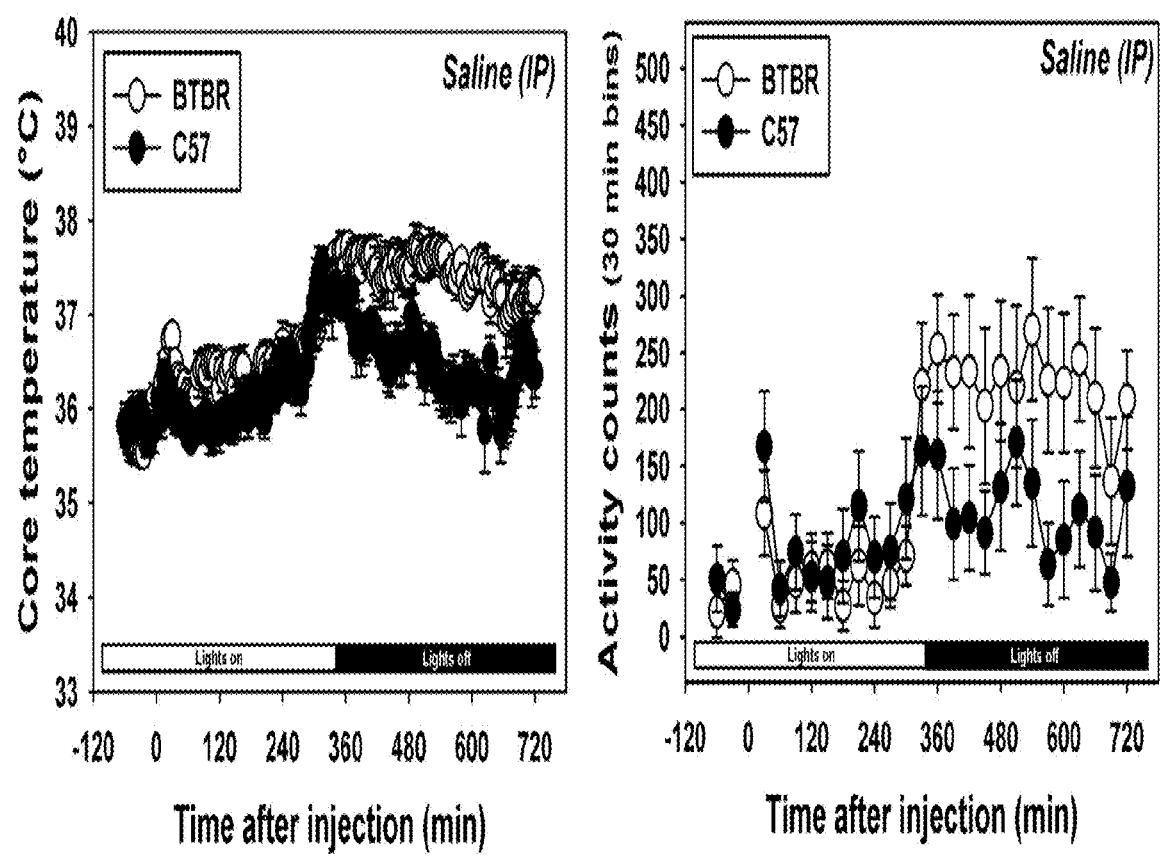
FIG. 10 are graphs showing the effect of saline injection on core temperature (left panel) and locomotor activity (right panel) in C57 (filled circles) and BTBR mice (open circles). Symbols represent group means, and error bars represent SEM unless the SEM is smaller than the size of the symbol. The bar at the bottom of each panel indicates when room lights were on or off.

Both strains displayed a transiently increased core temperature and higher activity levels for approximately 30 min following saline administration (FIG. 10). The activity also followed the normal circadian pattern for both strains. More motor activity was recorded during the subjective dark phase, but interestingly, the BTBR mice exhibited more activity than the C57s, along with an elevated core temperature likely due to this higher activity (FIG. 10).

Figure 11:
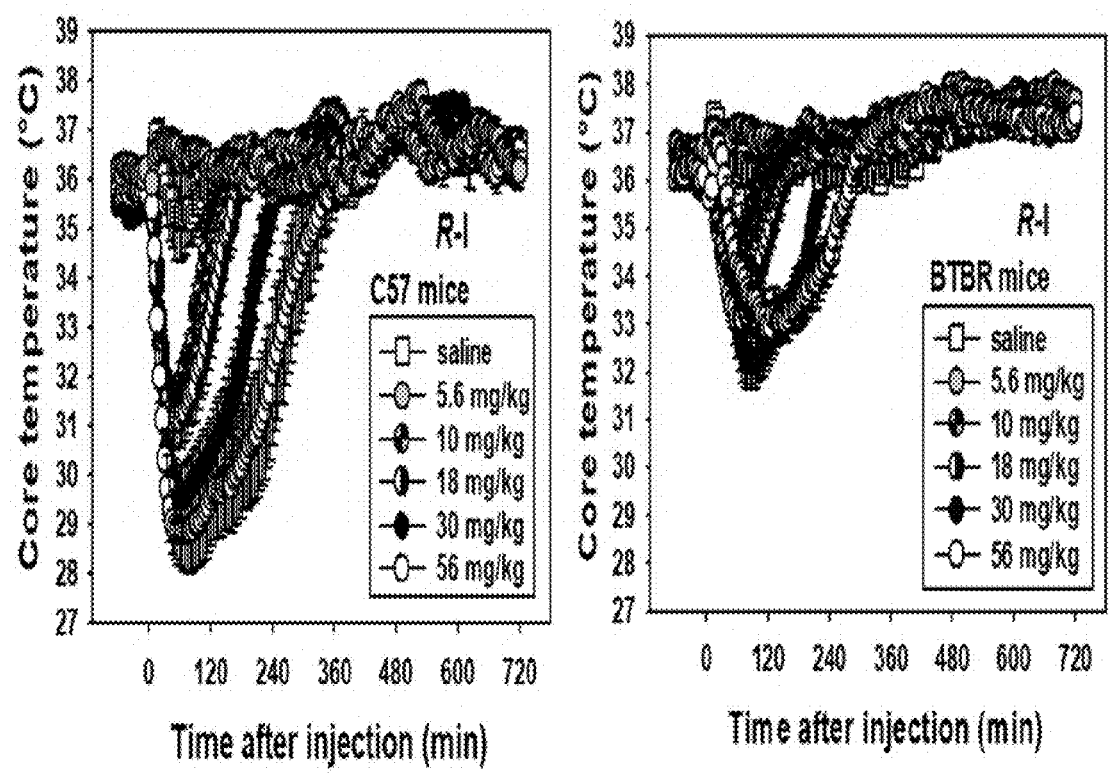
FIG. 11 are graphs showing the time activity curve for (R)-I effects on core body temperature in C57 (left panel) and BTBR mice (right panel). All injections were administered IP at a concentration of 0.1 cc/10 g.

Effect of (R)-I Injection on Core Temperature and (Locomotor Activity) LMA in C57 and BTBR Mice Intraperitoneal injection of (R)-I had a more acute response in C57 mice as compared to BTBR mice (FIG. 11). Unlike MDMA, (R)-I did not result in a rise in core body temperature in either of the strains at any of the doses tested. However, both strains exhibited dose-dependent hypothermic effects after injection. These effects were greater in C57 mice (Figure FIG. 12) following doses of 10, 18, 30 and 56 mg/kg. It was noted that at 5.6 mg/kg, (R)-I did not elicit a rise or drop in core body temperature in either of the mice strains.

Figure 13:
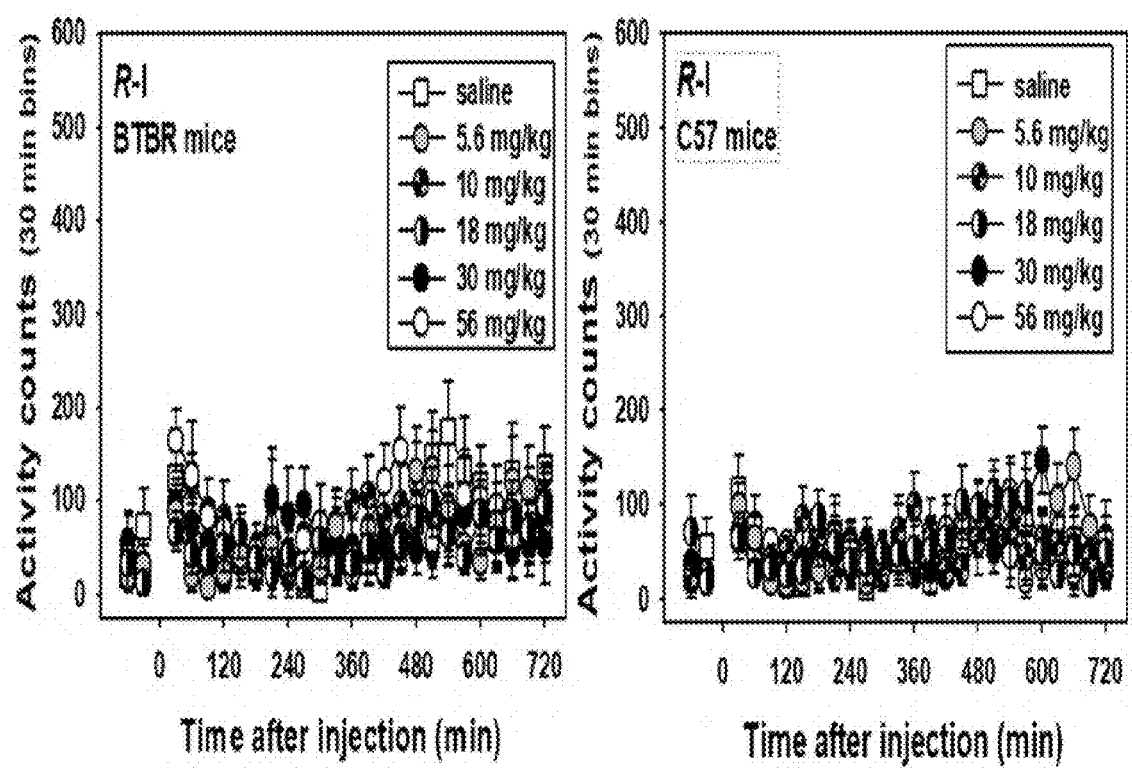
FIG. 13 are graphs showing time-activity curves for (R)-I effects on home cage locomotor activity in C57 (left panel) and BTBR (right panel) mice. All injections were administered IP at a concentration of 0.1 cc/10 g.

Intraperitoneal injection of different doses of (R)-I in C57 and BTBR did not have significant locomotor stimulant effects, even at doses as high as 30 mg/kg (FIG. 13). At 56 mg/kg i.p injection, (FIG. 14) BTBR mice elicited a locomotor effect stronger than C57 mice at the same dose, which was also significantly different from saline.

Figure 12:
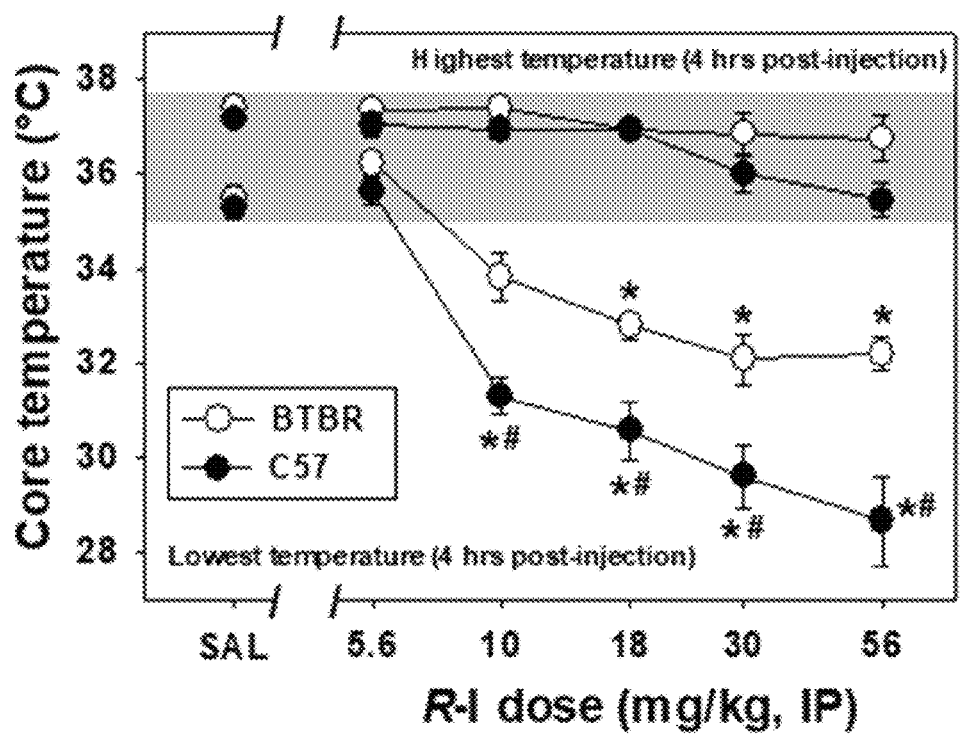
FIG. 12 is a graph showing the dose effect curves for highest and lowest temperatures observed within 4 hours of injection of (R)-I in C57 (filled circles) and BTBR mice (open circles). All injections were administered IP at a concentration of 0.1 cc/10 g. (*=significantly different from strain-appropriate saline value, #=significantly different between strains, within dose (by 1-way ANOVA and Tukey's HSD post hoc test.)

Together with the data presented in FIG. 12 and FIG. 13, it can be seen that (R)-I has a large safety margin, especially at doses up to 5.6 mg/kg in BTBR and C57 mice. At 10 mg/kg and above, hypothermic effects are noted in both strains.

Effect of (S)-I Injection on Core Temperature and (Locomotor Activity) LMA in C57 and BTBR Mice Intraperitoneal injection of (S)-I had a more acute response in C57 mice than BTBR mice.

However, (S)-I was more potent and resulted in a significant drop in temperature at lower doses (5.6 mg/kg) compared to the same dose tested at (R)-I in C57 mice (see FIGS. 15 to 18).

It was noted that neither strain exhibited locomotor stimulant effects, at any dose tested. However, the procedure used here may not have detected locomotor depressant effects because home cage activity is very low during the light phase when injections were administered. To determine whether S-PharmAla1 decreases motor activity, the mice may be placed into new cages with fresh bedding and nesting material immediately after injection (to stimulate exploratory and nest-building activity in saline controls) or open-field photobeam boxes with no habituation may be used. Example 9: Cardiotoxicity studies Cardiotoxicity of drugs is largely related to the capacity of the drug to inhibit the human ether-à-go-go-related gene (hERG) cardiac potassium channel. Inhibition of the cardiac hERG channel by drugs is known to be associated with potentially fatal arrhythmias. Therefore, a drug's interaction with hERG is routinely investigated to avoid the risk of cardiac side effects. Accordingly, a great number of in silico, in vitro and in vivo assays with hERG have been reported including in vitro model systems (hERG typically expressed in HEK or CHO cells) (Gintant G, Pharmacol Ther. 2011 February; 129(2):109-19; Garrido et al. Eur J Med Chem. 2020 Jun. 1; 195:112290.)

hERG inhibition studies are performed with the compound of Formula (R)-I and (S)-I and the exemplary and comparative compositions of the application.

Cardiotoxicity Studies in Rodent Models of Autism Spectrum Disorder

The 8 chamber CODA™ Non-invasive blood pressure system was set up to monitor the blood pressure of C57 and BTBR mice. Mice were habituated to restraint, saline injection (IP), and tail-cuff pressure monitoring for at least three days before drug administration. Across days, groups of habituated mice were injected IP with increasing doses of test drug, in this case (R)-I, (S)-I and (R/S)-I, then returned to the home cage for 30 min. Tail cuff pressure monitoring then determined effects on systolic, diastolic, and mean arterial pressure in restrained C57 and BTBR mice in sessions lasting ~30 min.

In the tail cuff pressure monitoring, an occlusion tail cuff was inflated to impede the blood flow to the tail. The cuff was deflated slowly, and a second tail cuff, incorporating the VPR sensor, measured the physiological characteristics of the returning blood flow. As the blood returned to the tail, the VPR sensor cuff measured the tail swelling resulting from arterial blood flow pulsations. Systolic blood pressure was automatically measured at the first appearance of tail swelling. Diastolic blood pressure was automatically measured when the increasing rate of swelling ceased in the tail.

Effect of (R)-I and (S)-I on Cardiovascular Effects in C57 and BTBR Mice

At 10 mg/kg in both C57 and BTBR mice, a hypothermic effect of both (R)-I and (S)-I was noted. Therefore, this study evaluated the effect of the drugs on systolic, diastolic, and mean arterial pressure at 10 mg/kg, and also 30 mg/kg.

Figure 14:
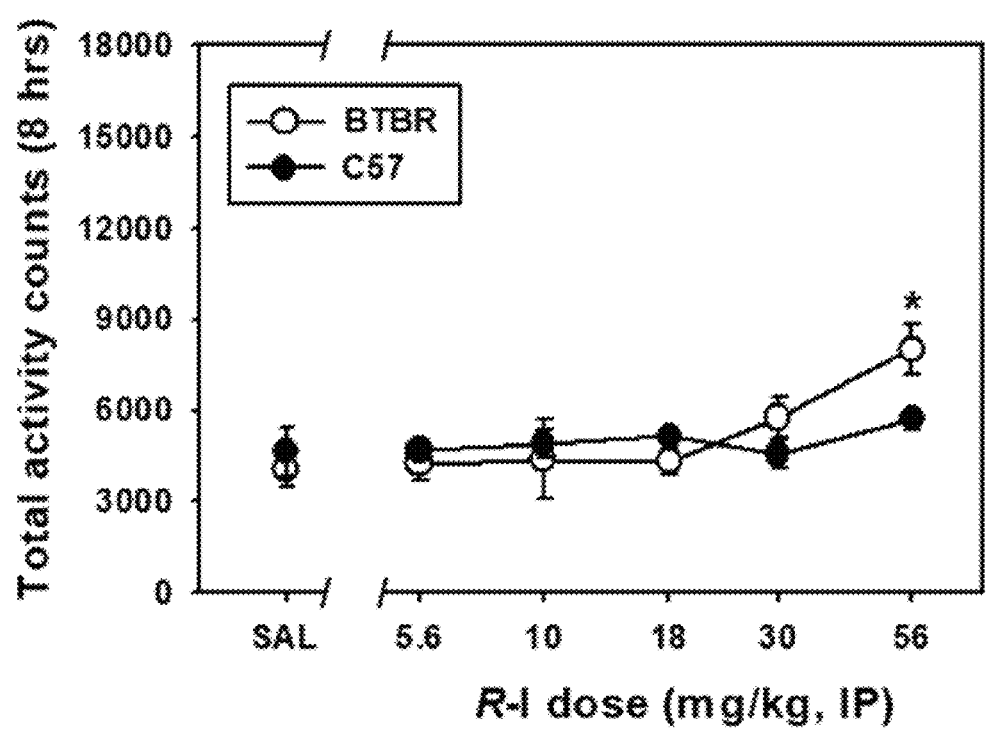
FIG. 14 is a graph showing the dose-effect curves for locomotor activity summed over 8 hours following injection of (R)-I in C57 (filled symbols) and BTBR mice (open symbols). All injections were administered IP at a concentration of 0.1 cc/10 g. (*=significantly different from strain-appropriate saline value (by 1-way ANOVA and Tukey's HSD post-hoc test.)
Figure 15:
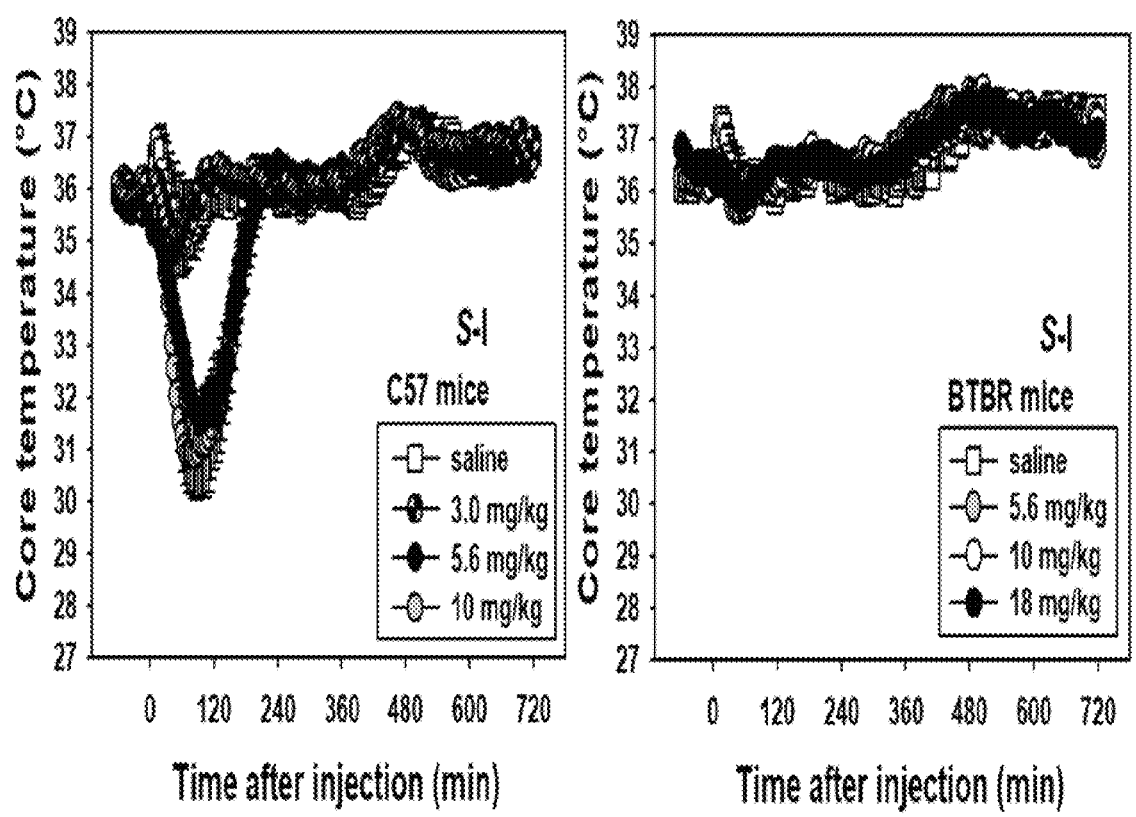
FIG. 15 are graphs showing time activity curve for (S)-I effects on core body temperature in C57 (left) and BTBR mice (right). All injections were administered IP at a concentration of 0.1 cc/10 g.
Figure 16:
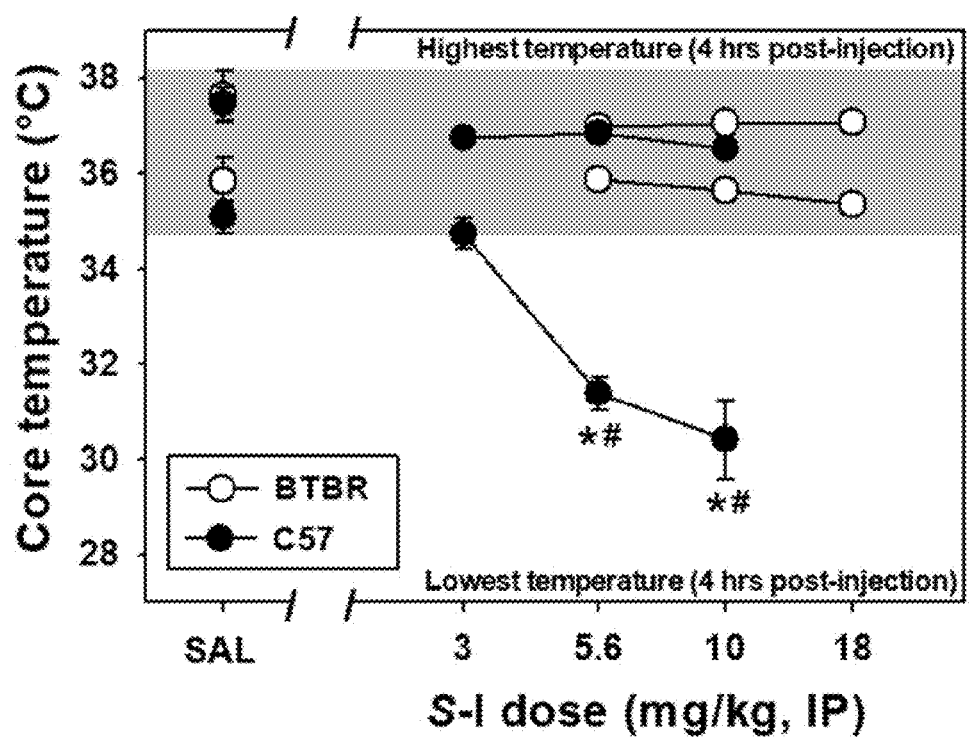
FIG. 16 is a graph showing dose-effect curves for highest and lowest temperatures observed within 4 hours of injection of (S)-I in C57 (filled symbols) and BTBR mice (open symbols). All injections were administered IP at a concentration of 0.1 cc/10 g. (*=significantly different from strain-appropriate saline value, #=significantly different between strains, within dose (by 1-way ANOVA and Tukey's HSD post-hoc test.)
Figure 17:
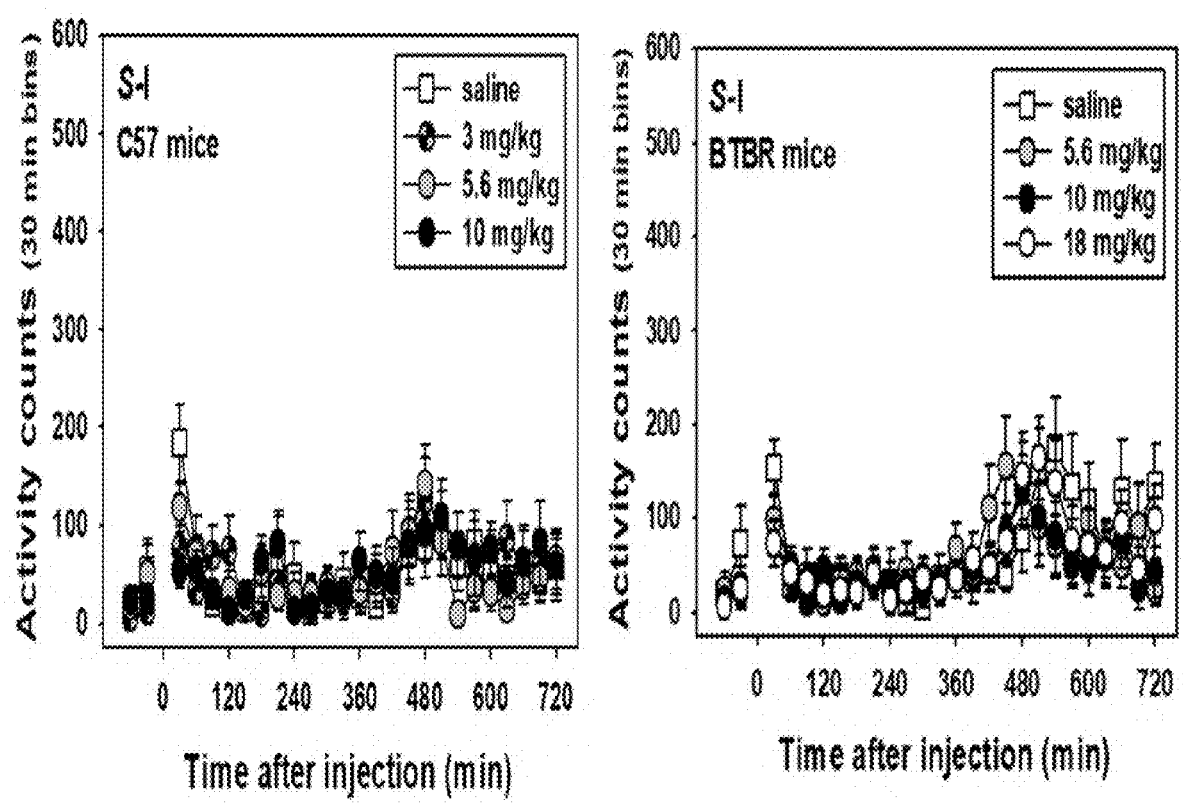
FIG. 17 are graphs showing time activity curves for (S)-I effects on locomotor activity in C57 (left) and BTBR (right). All injections were administered IP at concentration of 0.1 cc/10 g.
Figure 18:
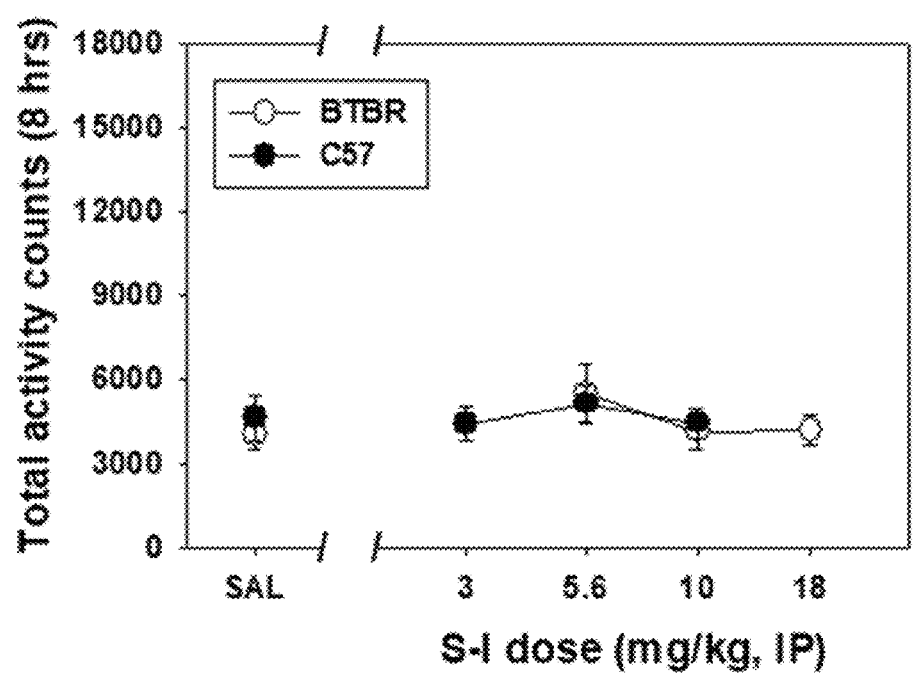
FIG. 18 is a graph showing Dose-effect curves for locomotor activity summed over 8 hours following injection of (S)-I in C57 (filled symbols) and BTBR mice (open symbols). All injections were administered IP at a concentration of 0.1 cc/10 g.
Figure 19:
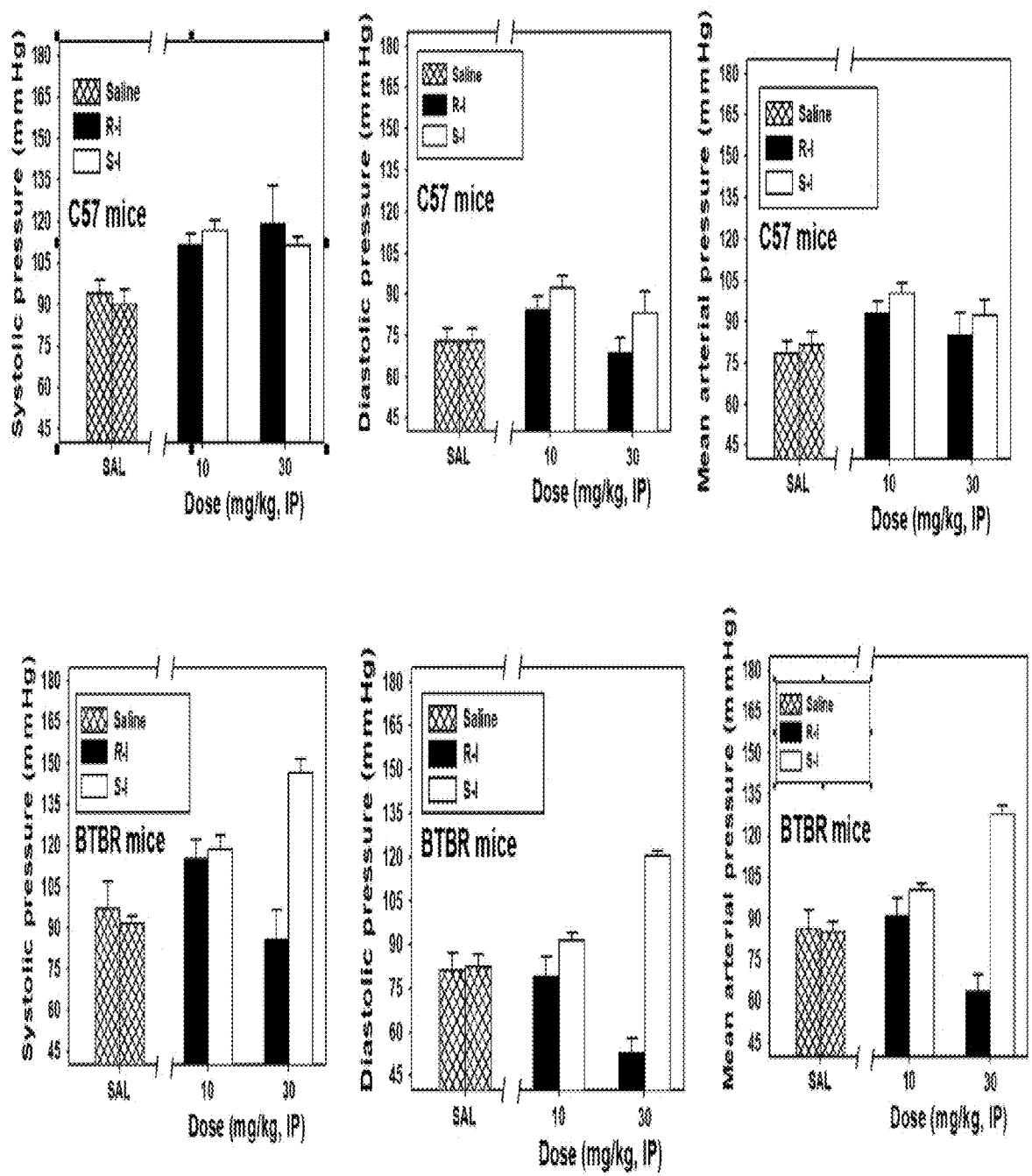
FIG. 19 are graphs showing the effects of saline (hatched bars), (E)-I (filled bars) and (S)-I (open bars) on systolic (top), diastolic (middle) and mean arterial blood pressure (bottom) in C57 (top panel) and BTBR (bottom panel) mice. All injections were administered IP at a concentration of 0.1 cc/10 g.
Figure 20:
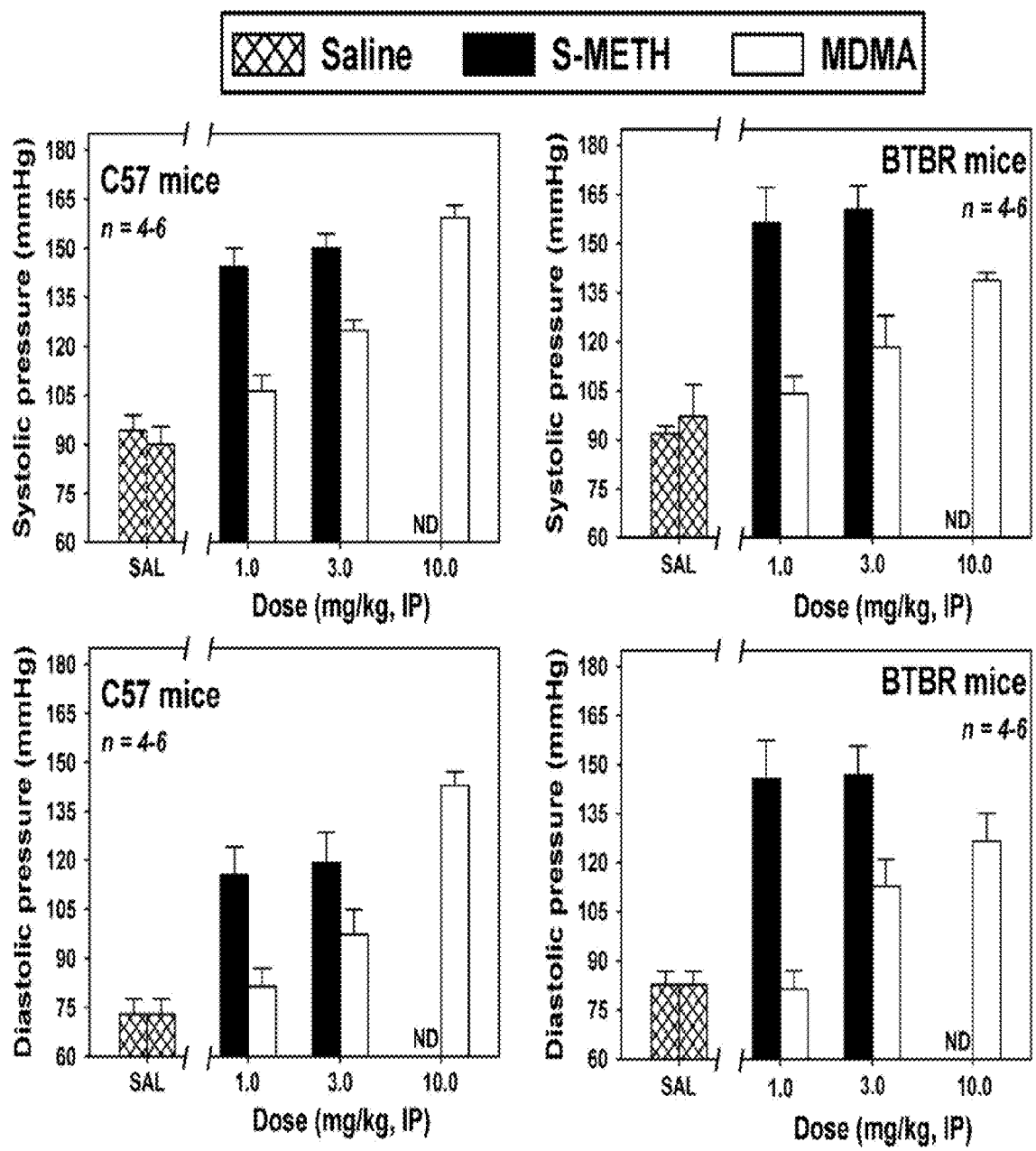
FIG. 20 are graphs showing the effects of saline (hatched bars), S-methamphetamine (filled bars) and racemic MDMA (open bars) on systolic (top) and diastolic (bottom) blood pressure in C57 (right) and BTBR (left) mice. All injections were administered IP at a concentration of 0.1 cc/10 g.

Based on data presented in FIG. 14 it was evident that (R)-I at 10 mg/kg and 30 mg/kg had a lower impact on cardiovascular effects than (S)-I. This is in line with the docking data described above, where (S)-I was predicted to bind more strongly to the 5HT2b receptor than (R)-I. Relative to racemic MDMA and S-methamphetamine (see Figure FIG. 20), both strains' blood pressure rise due to (R)-I (see FIG. 19) was significantly lower.

Summary: Docking studies predicted that the binding affinity of (S)-I to the 5HT2b receptor was stronger, which would result in a rise in blood pressure. At the dose tested (FIG. 19), 10 mg/kg i.p., it was seen that (S)-I does result in higher systolic and diastolic blood pressure than (R)-I. Relative to racemic MDMA (Figure), both enantiomers (R)-I and (S)-I are significantly less toxic.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

The invention claimed is:

1. An enantiomerically pure compound of Formula (R)-I or a salt and/or solvate thereof

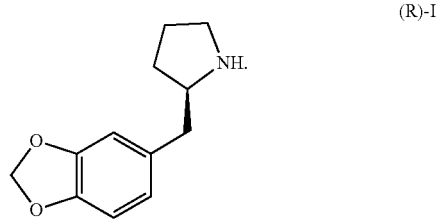 [SMILES: c1cc2c(cc1C[C@H]1CCCN1)OCO2]

(R)-I

2. The compound of claim 1, wherein the enantiomerically pure compound of Formula (R)-I or a salt and/or solvate thereof comprises 99% or greater by weight of the compound of Formula (R)-I or a salt and/or solvate thereof and 1% or less by weight of the compound of Formula (S)-I or a salt and/or solvate thereof

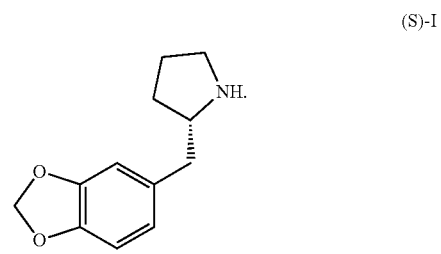 [SMILES: c1cc2c(cc1C[C@@H]1CCCN1)OCO2]

(S)-I

3. The compound of claim 1, wherein the enantiomerically pure compound of Formula (R)-I or a salt and/or solvate thereof comprises 99.1%, 99.2%, 99.3%, 99.4%, 99.5%, 99.6%, 99.7%, 99.8%, 99.9%, 99.91%, 99.92%, 99.93%, 99.94%, 99.95%, 99.96%, 99.97%, 99.98%, 99.9% or 100% by weight of the compound of Formula (R)-I and 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, or 0% respectively less by weight of the compound of Formula (S)-I or a salt and/or solvate thereof.

4. The compound of claim 1, wherein the enantiomerically pure compound of Formula (R)-I or a salt and/or solvate thereof comprises an enantiomeric excess (ee) of 98% or more.

5. The compound of claim 1, wherein the enantiomerically pure compound of Formula (R)-I or a salt and/or solvate thereof is in an acid salt form or solvate thereof.

6. A pharmaceutical composition comprising an enantiomerically pure compound of Formula (R)-I or a pharmaceutically salt and/or solvate thereof of claim 1 and a pharmaceutically acceptable carrier.

* * * * *